(12) United States Patent
Liu et al.

(10) Patent No.: US 9,066,959 B2
(45) Date of Patent: Jun. 30, 2015

(54) FICUS EXTRACTS HAVING ANGIOGENESIS INHIBITING ACTIVITY AND METHODS OF ISOLATING AND USING THE SAME

(75) Inventors: Zhijun Liu, Baton Rouge, LA (US); Eugene A. Woltering, Kenner, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 429 days.

(21) Appl. No.: 13/058,957

(22) PCT Filed: Aug. 14, 2009

(86) PCT No.: PCT/US2009/053860
§ 371 (c)(1),
(2), (4) Date: Mar. 17, 2011

(87) PCT Pub. No.: WO2010/019864
PCT Pub. Date: Feb. 18, 2010

(65) Prior Publication Data
US 2011/0165096 A1 Jul. 7, 2011

Related U.S. Application Data

(60) Provisional application No. 61/088,924, filed on Aug. 14, 2008.

(51) Int. Cl.

| | | |
|---|---|---|
| *A61P 35/00* | (2006.01) |
| *A61P 17/06* | (2006.01) |
| *A61P 19/02* | (2006.01) |
| *A61P 41/00* | (2006.01) |
| *C12Q 1/02* | (2006.01) |
| *A61K 9/12* | (2006.01) |
| *A61P 3/04* | (2006.01) |
| *A61P 1/00* | (2006.01) |
| *A61P 9/12* | (2006.01) |
| *A61P 37/00* | (2006.01) |
| *A61P 31/10* | (2006.01) |
| *A61P 27/02* | (2006.01) |
| *A61K 36/00* | (2006.01) |
| *A61K 36/60* | (2006.01) |

(52) U.S. Cl.
CPC ..................................... *A61K 36/60* (2013.01)

(58) Field of Classification Search
None
See application file for complete search history.

(56) References Cited

U.S. PATENT DOCUMENTS

2006/0228426 A1* 10/2006 Cyr .............................. 424/725

FOREIGN PATENT DOCUMENTS

| JP | 10298089 | 11/1998 |
| WO | 2006007676 | 1/2006 |

OTHER PUBLICATIONS

International Search Report of PCT/US2009/053860 dated Apr. 5, 2010 (3 pages).
Written Opinion of PCT/US2009/053860 (3 pages).

* cited by examiner

*Primary Examiner* — Peter J Reddig
*Assistant Examiner* — Sarah Chickos
(74) *Attorney, Agent, or Firm* — Miles & Stockbridge PC

(57) ABSTRACT

The present invention is directed to methods for extracting and isolating extracts having angiogenesis inhibiting activity from a latex-containing portion of a *Ficus* variant, pharmaceutical and nutraceutical compositions comprising the extracts, methods of administering the extracts to treat angiogenesis-dependent diseases and to reduce or inhibit neovessel growth in a subject in need thereof, and the use of the extracts in the manufacture of a composition for reducing or inhibiting neovessel growth.

53 Claims, 23 Drawing Sheets

Mean Angiogenic Index = 1+1+1+1 = 4

Mean Angiogenic Index = 4+4+4+4 = 16

US 9,066,959 B2

FICUS EXTRACTS HAVING ANGIOGENESIS INHIBITING ACTIVITY AND METHODS OF ISOLATING AND USING THE SAME

CROSS-REFERENCE TO RELATED APPLICATIONS

This Non-Provisional Patent Application claims the benefit of U.S. Provisional Patent Application No. 61/088,924, filed on Aug. 14, 2008, and which is hereby incorporated by reference in its entirety.

FIELD OF THE INVENTION

The present invention is directed to methods for extracting and isolating extracts having angiogenesis inhibiting activity from the latex-containing portion of the *Ficus* genus, pharmaceutical dosage forms and nutraceutical compositions comprising the *Ficus* extracts, and methods of administering the *Ficus* extracts to treat angiogenesis-dependent diseases and inhibit or reduce neovessel growth in subjects in need thereof.

DESCRIPTION OF RELATED ART

The search for effective and less toxic treatments for cancer and cancer cell proliferation is an ongoing area of intense research. One promising area of research is the development of anti-tumor agents that inhibit tumor angiogenesis, a necessary step for tumors and their metastases to grow beyond a microscopic size. Angiogenesis, the process of blood vessel growth, occurs not only in the development, reproduction and repair of new tissue, but also in tumor formation in cancers and a variety of other non-neoplastic diseases such as autoimmune disorders, age-related macular degeneration and atherosclerosis. Such "pathological" angiogenesis can persist for years, and therefore active agents that target angiogenesis inhibition provide the possibility for low-dose, local treatment that can both stop the growth of existing tumors and inhibit future tumor growth.

Mechanisms of angiogenesis inhibition typically focus on inhibition of vascular endothelial growth factor (VEGF) secretion and/or VEGF binding at its receptor (VEGFR2) and its binding to neuropilin on endothelial cells. Known angiogenesis inhibiting active agents include Bevacizumab (AVASTIN®; Genentech, Inc., South San Francisco, Calif.), Bortezomib (VELCADE®; Millennium Pharmaceuticals, Inc., Cambridge, Mass.), Erlotinib (TARCEVA®; OSI Pharmaceuticals, Inc., Melville, N.Y.), Pegaptanib (MACU-GEN®; OSI Pharmaceuticals, Inc.), Ranibizumab (LUCENTIS®; Genentech, Inc.), Sorafenib (NEXAVAR®; Bayer Aktiengesellschaft, Leverkusen-Bayerwerk, Germany), Lenalidomide (REVLIMID®; Celgene Corp., Summit, N.J.), and Sunitinib (SUTENT®; Pfizer, Inc., New York, N.Y.). However, for the most part these active agents are biological molecules (i.e., polypeptides) that must be prepared using costly biotechnology manufacturing and purification processes. The high cost and difficulty in manufacturing angiogenesis inhibiting agents could be greatly reduced by identifying natural products having angiogenesis inhibiting activity that can be readily isolated from a plant source.

In adults, two types of blood vessels can potentially be found. The normal blood vessel is a resting, quiescent, fully-developed vessel. A second form, a proliferating or developing blood vessel, occurs rarely during the normal human life cycle (occurring only in early development and during reproduction, e.g., menstrual cycle and pregnancy). In contrast, the process of angiogenesis, the proliferation and development of new blood vessels, often occurs in wound healing and in pathological processes, e.g., tumor growth. Angiogenesis is a complex process involving many stages, including extracellular matrix remodeling, endothelial cell migration and proliferation, capillary differentiation, and anastomosis. All detectable solid tumors (tumors over 2 mm in diameter, a size reflecting the limit of simple diffusion to supply cells with oxygen and nutrients or to remove wastes) exploit angiogenesis to supply the needed blood to proliferating tumor cells. Studies have demonstrated that the level of vascularization in a tumor is strongly associated with metastasis in melanoma, breast, and lung carcinomas. See R. Bicknell, "Vascular targeting and the inhibition of angiogenesis," Annals of Oncology, vol. 5, pp. 45-50 (1994).

Angiogenesis inhibitors have been suggested to intervene into neoplastic processes. See G. Gasparini, "The rationale and future potential of angiogenesis inhibitors in neoplasia," Drugs, vol. 58, pp. 17-38 (1999). The inhibitory agents block angiogenesis, thereby causing tumor regression in various types of neoplasia. Known therapeutic candidates include naturally occurring angiogenic inhibitors (e.g., angiostatin, endostatin, platelet factor-4), specific inhibitors of endothelial cell growth (e.g., TNP-470, thalidomide, interleukin-12), agents that neutralize angiogenic molecules (e.g., antibodies to fibroblast growth factor or vascular endothelial growth factor), suramin and its analogs, tecogalan, agents that neutralize receptors for angiogenic factors, agents that interfere with vascular basement membrane and extracellular matrix (e.g., metalloprotease inhibitors, angiostatic steroids), and anti-adhesion molecules (e.g., antibodies such as anti-integrin alpha V beta 3). See L. Rosen, "Antiangiogenic strategies and agents in clinical trials," Oncologist, vol. 5, supplement 1, pp. 20-27 (2000).

Pathogenic angiogenesis occurs when improper control of angiogenesis causes either excessive or insufficient blood vessel growth. Excessive blood vessel proliferation in cancer-related conditions favors tumor growth and development of distant metastases. In other diseases, it is the root cause of tissue injury, including blindness associated with proliferative retinopathies, skin disorders such as psoriasis, and rheumatoid arthritis. Diseases that have been associated with neovascularization include, for example, Crohn's disease, diabetic retinopathy, macular degeneration, obesity, corneal neovascularization, malignant tumor growth beyond 2 mm diameter, benign tumors, benign functional endocrine tumors, hemangioma, arterial/venous malformations, sickle cell anemia, sarcoidosis, syphilis, pseudoxanthoma elasticum, Paget's disease, vein occlusion in the eye, infections of the retina, primary hyperparathyroidism, secondary hyperparathyroidism, tertiary hyperparathyroidism, artery occlusion, carotid obstructive disease, chronic uveitis/vitritis, mycobacterial infections, Lyme disease, systemic lupus erythematosis, psoriasis, retinopathy of prematurity, Eales disease, Behcet's disease, infections causing retinitis or choroiditis, presumed ocular histoplasmosis, Best's disease, myopia, optic pits, Stargardt's disease, pars planitis, chronic retinal detachment, hyperviscosity syndrome, toxoplasmosis, trauma, rheumatoid arthritis, and post-laser laser complications. Other angiogenic-related diseases may include, for example, diseases associated with rubeosis (neovascularization of the angle), and diseases caused by abnormal proliferation of fibrovascular or fibrous tissue, including all forms of proliferative vitreoretinopathy. Any disease having a known angiogenic counterpart could potentially be treated with an anti-angiogenic factor, e.g., psoriasis. See D. Creamer et al., "Overexpression of the angiogenic factor platelet-derived endothelial cell growth factor/thymidine phosphorylase in psoriatic epidermis," *Br. J. Dermatol.*, vol. 137, pp. 851-855 (1997).

Angiogenesis is a prominent contributor to solid tumor growth and the formation of distant metastases. Several experimental studies have concluded that primary tumor growth, tumor invasiveness, and metastasis all require neovascularization. The process of tumor growth and metastasis is complex, involving interactions among transformed neoplastic cells, resident tissue cells (e.g., fibroblasts, macrophages, and endothelial cells), and recruited circulating cells (e.g., platelets, neutrophils, monocytes, and lymphocytes). A possible mechanism for the maintenance of tumor growth is an imbalance, or disregulation, of stimulatory and inhibitory growth factors in and around the tumor. Disregulation of multiple systems allows the perpetuation of tumor growth and eventual metastasis. Angiogenesis is one of many systems that is disregulated in tumor growth. In the past it has been difficult to distinguish between disregulation of angiogenesis and disregulation of other systems affecting a developing tumor. Another complicating factor is that aggressive human melanomas mimic vasculogenesis by producing channels of patterned networks of interconnected loops of extracellular matrix, in which red blood cells, but not endothelial cells, are detected. See A. J. Maniotis et al., "Vascular channel formation by human melanoma cells in vivo and in vitro: Vasculogenic mimicry," Am. J. Pathol., vol. 155, pp. 739-52 (1999). These channels may facilitate perfusion of tumors, independent of perfusion from angiogenesis.

A tumor cannot expand beyond approximately 2 mm in diameter without a blood supply to provide nutrients and remove cellular wastes. Tumors in which angiogenesis is important include solid tumors, and benign tumors including acoustic neuroma, neurofibroma, trachoma, and pyogenic granulomas. Inhibiting angiogenesis could halt the growth and potentially lead to regression of these tumors. Angiogenic factors have been reported as being associated with several solid tumors, including rhabdomyosarcoma, retinoblastoma, Ewing's sarcoma, neuroblastoma, and osteosarcoma.

Angiogenesis has also been associated with some non-solid tumors, including blood-born tumors such as leukemias, various acute or chronic neoplastic diseases of the bone marrow marked by unrestrained proliferation of white blood cells, usually accompanied by anemia, impaired blood clotting, and enlargement of the lymph nodes, liver, and spleen. It is believed that angiogenesis may play a role in the abnormalities in the bone marrow that give rise to leukemias and multiple myelomas.

Anti-angiogenic factors inhibit tumor growth beyond 2 mm in diameter by inhibiting the angiogenic response and thus inhibiting blood vessel growth to the tumor. Although angiogenesis in a tumor may begin at an early stage, a tumor requires a blood supply to grow much beyond about 2 mm in diameter. Up to 2 mm diameter, tumors can survive by obtaining nutrients and oxygen by simple diffusion. Most anti-angiogenic factors are not cytotoxic, i.e., capable of killing the tumor cells directly. Small tumors of a size about 1 $mm^3$ can be effectively inhibited and destroyed by factors, either endogenous or exogenous, that stimulate the immune system. It is generally accepted that once a tumor has reached a critical size, the immunological system is no longer able to effectively destroy the tumor; i.e., there is a negative correlation between tumor size and immune competence. See A. K. Eerola et al., "Tumour infiltrating lymphocytes in relation to tumour angiogenesis, apoptosis," Lung Cancer, vol. 26, pp. 73-83 (1999); and F. A. Wenger et al., "Tumor size and lymph-node status in pancreatic carcinoma—is there a correlation to the preoperative immune function?," Langenbecks Archives of Surgery, vol. 384, pp. 473-478 (1999). Early adjuvant use of an effective anti-angiogenic agent to preclude development of tumor metastases beyond 1 to 2 $mm^3$ may allow more effective tumor attack and control by the body's immunological mechanisms. In addition, prolonged adjuvant use of a non-toxic angiogenic inhibitor may prevent tumor dissemination by blocking the growth of vessels required for the transport of tumor cells that would form metastatic foci.

Angiogenesis has also been implicated in obesity. Several mice strains, both young and aged animals, used as obesity models treated with anti-angiogenic agents lost weight. See M. A. Rupnick et al., "Adipose tissue mass can be regulated through the vasculature," PNAS, vol. 99, pp. 10730-10735 (2002). This same study also found that adipose tissue mass was reduced by the anti-angiogenic compounds.

Angiogenesis has also been implicated in psoriasis. Psoriasis is a chronic inflammatory skin disease characterized by exaggerated keratinocyte proliferation. A current paradigm indicates that psoriasis is driven by T cell-mediated immune responses targeting keratinocytes. However, psoriasis cannot be explained solely on the basis of T-cell activation, and it is likely that intrinsic alterations in epidermal keratinocytes play a very relevant role in disease expression. In particular, keratinocytes may be important in initiating, sustaining, and amplifying the inflammatory responses by expressing molecules involved in T-cell recruitment, retention, and activation. Keratinocytes are also a relevant source of growth factors for angiogenesis. In fact, a hallmark of psoriatic skin is the substantial transformation of the local microvascular system, showing dilatation and tortuosity of capillaries, increased permeability, and high endothelial venule formation.

In psoriasis, an abundance of blood vessels is present in the papillary dermis, showing microvascular changes such as pronounced dilatation and tortuosity. Expansion of the microvascular dermal plexus is believed to be mediated by angiogenesis, which is an active vasoproliferative process. It has been suggested that VEGF, which has been shown to be dramatically elevated in human psoriatic skin, might play a causative role in the vascular changes seen in this disease and also in epidermal and inflammatory alterations. Recently, vascular endothelial growth factor receptors (VEGFRs, including VEGFR-1, VEGFR-2 and VEGFR-3) were found to be expressed in normal human epidermis and associated with proliferation and migration of keratinocytes. Overexpression of VEGFR-1, VEGFR-2 and VEGFR-3 in psoriatic epidermis was demonstrated both at mRNA and protein levels in vitro, suggesting that VEGFRs are overexpressed in lesional psoriatic epidermal keratinocytes.

New anti-angiogenic factors are needed, in particular, compounds that not only inhibit new angiogenic growth, but also that degrade existing capillary networks. Very few anti-angiogenic factors have been reported to diminish existing capillary networks.

The latex (i.e., milksap, resin, or sap) of many species of the genus *Ficus* exhibit strong pharmacological effects in man and animal models, including antitumor and/or cytotoxic activity. For example, alkaloid compounds exhibiting tumor necrotic effects in mice were isolated from *Ficus carica* latex by filtration followed by dialysis (see, e.g., S. B. Ullman et al., *Exp. Med. Sur.* 3:11 (1945)). The latex was shown to also contain a water-soluble non-dialyzable fraction that exhibited strong cytotoxic effects, which was hypothesized to contain a proteolytic enzyme. Enzymatic cytotoxic activity has been observed in extracts from both *Ficus carica* and *Ficus gla-*

*brata* (see, e.g., U.S. Pat. Nos. 2,163,643 and 2,995,493, and U.S. Pat. No. 1,616,291, respectively).

More recently, researchers have characterized a broad range of lipophilic extracts from the latex, seeds, roots, and bark of *Ficus* species using, for example, an organic solvent extraction method. For example, I3-sitosterols extracted from *Ficus carica* latex have been investigated for activity involving suppression of cancer cell proliferation (see, e.g., S. Rubnov et al., *J. Nat. Prod.* 64:993 (2001)), as well as mitigating oxidative damage in response to ferric nitrilotriacetate (see, e.g., N. Khan and S. Sultana, *Life Sciences* 77:1194 (2005)). Other lipophilic compounds present in *Ficus* latex that have been characterized by gas chromatography/mass spectrometry ("GC/MS") include campesterol, stigmasterol, fucosterol, and fatty acids such as myristic acid, palmitic acid, stearic acid, oleic acid, linoleic acid, and linolenic acid (see, e.g., W. S. Jeong and P. A. Lachance, *J. Food Sci.* 66:278 (2001)). Additionally, cytotoxic triterpenes have been extracted from the aerial roots of *Ficus microcaoa* (see, e.g., Y.-M. Chiang et al., *Phytochemistiy* 66:495 (2005)). Similar triterpenes such as betulinic acid have been investigated for regulating hair growth (see, e.g., U.S. Pat. Nos. 6,124,362 and 6,482,857 B1).

The observed activity of *Ficus* extracts is highly dependent on the extraction and purification procedures. For example, 2,5-dihydroxytetrahydro-2-furancarboxylic acids have been extracted from *Ficus elastica* and shown to have anticancer, apoptosis-inducing activity (see, e.g., U.S. Pat. No. 6,133, 238). Methanol extraction followed by silica gel chromatography has been demonstrated as useful for extracting agents from *Ficus benghalensis* bark having anti-tumor activity (see, e.g., U.S. Pat. No. 6,660,309 B2). Additionally, flavonoids and polyphenols extracted from *Ficus citrifblia*, administered to patients undergoing chemotherapy, have been demonstrated to exhibit improved modulation of cancer cell resistance to chemotherapeutic agents (see, e.g., P.-N. Simon et al., *Anticancer Res.* 21:1023 (2001)). Anti-cancer extracts from a broad spectrum of herbs and fruits including *Ficus racemosa* have also been extracted using freon gas (see, e.g., U.S. Pat. No. 6,780,441 B2).

Substituted aurone derivatives having antifungal activity have been extracted from the seeds of *Ficus religiosa* (see, e.g., U.S. Pat. No. 6,307,070 B1). Anthocyanin and other flavonoid derivatives extracted from fig fruit have also been shown to have anti-inflammatory COX-2 inhibiting activity (see, e.g., U.S. Pat. Nos. 6,818,234 B1 and 7,192,611 B2).

However, extracts from *Ficus* variants such as *Ficus carica*, or any other *Ficus* species, have not been previously shown to exhibit angiogenesis inhibiting activity.

BRIEF SUMMARY OF THE INVENTION

The present invention is directed to a process for isolating a *Ficus* extract having angiogenesis inhibiting activity, the process comprising: mixing a latex-containing portion of a *Ficus* variant with a polar solvent to provide a liquid extract; washing the liquid extract with an organic solvent to provide an aqueous extract; and fractionating the aqueous extract to provide a *Ficus* extract having angiogenesis inhibiting activity.

The present invention is also directed to a process for obtaining a *Ficus* extract having angiogenesis inhibiting activity in a human or animal, the process comprising: preparing an aqueous extract from a latex-containing portion of a *Ficus* variant; fractionating the aqueous extract; and selecting as the *Ficus* extract having angiogenesis inhibiting activity in a human or animal, a substantially protein-free fraction containing one or more compounds having a molecular weight of about 200 Da to about 2,000 Da wherein the *Ficus* extract exhibits angiogenesis inhibiting activity.

In some embodiments, angiogenesis inhibiting activity is exhibited as an inhibition or a reduction of neovessel growth in an in vitro model such as, but not limited to, a tumor fragment, a placental sample, and the like. In some embodiments, angiogenesis inhibiting activity is exhibited as an inhibition or a reduction of neovessel growth in a human or animal subject in need thereof.

In some embodiments, the process further comprises macerating the latex-containing portion of the *Ficus* variant.

In some embodiments, fractionating comprises applying the aqueous extract to an adsorbent, and eluting a *Ficus* extract having angiogenesis inhibiting activity from the adsorbent with an eluting solvent. In some embodiments, an eluting solvent comprises an organic solvent. In some embodiments, an eluting solvent comprises about 95% ethanol and about 5% water. In some embodiments, an adsorbent is porous and has an average pore size of about 20 nm or less.

In some embodiments, a process further comprises adding a *Ficus* extract having angiogenesis inhibiting activity to an alcoholic solution to provide a precipitate having angiogenesis inhibiting activity. In some embodiments, a *Ficus* extract is added to an alcoholic solution in a dropwise manner.

In some embodiments, a process further comprises treating a *Ficus* extract having angiogenesis inhibiting activity with activated carbon.

In some embodiments, a process further comprises removing at least a portion of a polar solvent from a liquid extract. In some embodiments, a polar solvent is a $C_1$-$C_{10}$ compound comprising a heteroatom selected from: N, O, P, S, and combinations thereof. In some embodiments, a polar solvent is a solvent selected from: a $C_1$-$C_{10}$ alcohol, a $C_4$-$C_{10}$ ether, a $C_3$-$C_{10}$ aldehyde, a $C_3$-$C_{10}$ ketone, a $C_2$-$C_{10}$ carboxylic acid, a $C_2$-$C_{10}$ ester, a $C_3$-$C_{10}$ amine, a $C_1$-$C_5$ amide, and combinations thereof. In some embodiments, a polar solvent has a boiling point of about 200° C. or less.

In some embodiments, a process further comprises filtering a liquid extract. In some embodiments, washing further comprises dissolving a liquid extract in water. In some embodiments, a process further comprises freeze-drying one or more of the extracts.

The present invention is also directed to a *Ficus* extract prepared by the above processes.

In some embodiments, a latex-containing portion of a *Ficus* variant comprises at least a portion of a fruit of a *Ficus* variant. In some embodiments, a latex-containing portion of a *Ficus* variant comprises a *Ficus carica* fruit.

In some embodiments, a *Ficus* extract has angiogenesis inhibiting activity in the micromolar range. In some embodiments, a *Ficus* extract is substantially lacking cytotoxic activity. In some embodiments, a *Ficus* extract is substantially free from one or more of: shikimic acid, fumaric acid, syringin, chlorogenic acid, catechin, coumaric acid, psoralen, and bergapten.

In some embodiments, a *Ficus* extract of the present invention has a chromatograph having peaks at about 4.9 minutes, about 6.0 minutes, about 21.3 minutes, about 22.5 minutes, about 35.0 minutes, and about 49.7 minutes, when subjected to HPLC using a $C_{18}$ reverse phase column having an internal diameter of about 4.6 mm and a length of about 250 mm; wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

In some embodiments, a *Ficus* extract of the present invention further comprises rutin, wherein the rutin appears as a peak in the chromatograph having a retention time of about 51 minutes.

In some embodiments, the *Ficus* extract of the present invention has a HPLC chromatograph that further comprises a chromatograph peak of at least one of: about 3.0 minutes, about 3.2 minutes, about 4.9 minutes, about 6.0 minutes, about 8.6 minutes, about 15.3 minutes, about 19.6 minutes, about 27.7 minutes, about 28.7 minutes, about 29.3 minutes, about 30.4 minutes, about 33.1 minutes, about 34.0 minutes, about 37.0 minutes, about 44.1 minutes, about 45.7 minutes, about 46.3 minutes, about 48.2 minutes, about 53.0 minutes, about 57.3 minutes, and combinations thereof.

In some embodiments, a *Ficus* extract of the present invention has a chromatograph substantially in accordance with FIG. 16 when subjected to HPLC using a $C_{18}$ reverse phase column having an internal diameter of about 4.6 mm and a length of about 250 mm; wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10° A to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

In some embodiments, a $C_{18}$ reverse phase column suitable for use with the present invention comprises a packing material having a particle size of about 3 µm to about 5 µm, a pore size of about 100 Å, and a carbon loading of about 19%.

The present invention is also directed to a method of inhibiting or reducing neovessel growth in a human or animal, the method comprising administering a composition comprising a *Ficus* extract. Preferably, the *Ficus* extract comprises rutin and exhibits angiogenesis inhibiting activity to a human or animal in need thereof.

The present invention is also directed to a method of inhibiting or reducing neovessel growth associated with an angiogenesis-dependent disease in a human or animal in need thereof, the method comprising: administering to the subject a composition comprising a *Ficus* extract having angiogenesis inhibiting activity. Preferably, the *Ficus* extract is isolated by a process of the present invention. The present invention is also directed to a method of treating an angiogenesis-dependent disease in a subject in need thereof, the method comprising: administering to the subject a composition comprising a *Ficus* extract having angiogenesis inhibiting activity, wherein the *Ficus* extract is isolated by a process of the present invention.

The present invention is also directed to the use of a *Ficus* extract comprising rutin, wherein the *Ficus* extract has angiogenesis inhibiting activity, in the manufacture of a composition for reducing or inhibiting neovessel growth. Preferably, the *Ficus* extract is isolated by a process of the present invention. The neovessel growth may be associated with an angiogenesis-dependent disease.

Angiogenesis-dependent diseases suitable for treatment by a method of a present invention or inhibiting or reducing neovessel growth associated with the diseases include, but are not limited to: cancer; infectious diseases, including mycobacterial infections, infections of the retina, presumed ocular histoplasmosis, and infections causing retinitis or choroiditis; autoimmune disorders; benign tumors, e.g., haemangiomas (including infantile haemangiomas, capillary haemangiomas, and cavernous haemangiomas), functional endocrine tumors, acoustic neuromas, neurofibromas, trachomas, and pyogenic granulomas; atherosclerosis and atherosclerotic plaques; ocular angiogenic diseases, e.g., diabetic retinopathy, retinopathy of prematurity, macular degeneration, corneal graft rejection, neovascular glaucoma, retrolental fibroplasia, rubeosis, retinoblastoma, persistent hyperplastic vitreous syndrome, choroidal or corneal neovascularization, venous occlusion, uveitis, vitritis, Eales disease, Behcet's disease, proliferative vitreoretinopathy, ocular ischemic syndrome, and pterygium; myopia; optic pits; Best disease; Stargardt's macular dystrophy; pars planitis; chronic retinal detachment; hyperviscosity syndrome; rheumatoid arthritis; psoriasis; warts; allergic dermatitis; blistering disease; Karposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; transplant arteriopathy; restenosis; obesity; myocardial angiogenesis; coronary collaterals; cerebral collaterals; arteriovenous malformations; ischemic limb angiogenesis; primary pulmonary hypertension; pulmonary edema; asthma; nasal polyps; inflammatory bowel disease; periodontal disease; ascites; peritoneal adhesions; Osler-Weber-Rendu syndrome (hereditary hemorrhagic telangiectasia); plaque neovascularization; telangiectasia; hemophiliac joints; synovitis; osteomyelitis; osteophyte formation; angiofibroma; fibromuscular dysplasia; wound granulation; Crohn's disease; peptic ulcer; malignant tumor growth beyond 2 mm in diameter; sickle cell anemia; sarcoidosis; syphilis; pseudoxanthoma elasticum; Paget's disease; primary hyperparathyroidism; secondary hyperparathyroidism; tertiary hyperparathyroidism; arterial occlusion; carotid obstructive disease; Lyme disease; systemic lupus erythematosis; toxoplasmosis; trauma; Wegner's granulomatosis; post-laser complications; and combinations thereof.

The present invention is also directed to a method of analytically determining and characterizing a *Ficus* extract having angiogenesis inhibiting activity, the method comprising providing a *Ficus* extract by a process of the present invention, and analyzing the *Ficus* extract having angiogenesis inhibiting activity by applying the *Ficus* extract to a HPLC column, eluting a component of the *Ficus* extract from the HPLC column, and detecting the component of the *Ficus* extract as the component elutes from the HPLC column.

In some embodiments, the analyzing provides that the *Ficus* extract comprises rutin, having a retention time of about 51.0 minutes. In some embodiments, the analyzing provides that the *Ficus* extract is substantially free from one or more of: shikimic acid, fumaric acid, syringin, chlorogenic acid, catechin, coumaric acid, psoralen, and bergapten.

In some embodiments, the process further comprises macerating the latex-containing portion of a *Ficus* variant, wherein the latex-containing portion of the *Ficus* variant includes a fruit of a *Ficus* variant.

In some embodiments, the fractionating comprises applying the aqueous extract to an adsorbent and eluting the extract having angiogenesis inhibiting activity from the adsorbent with an eluting solvent.

In some embodiments, the analyzing comprises eluting with a first eluent of acetonitrile and a second eluent of water containing about 0.3% phosphoric acid and about 2.5% acetonitrile, wherein the concentration of the first eluent and second eluent is 100% by volume, and wherein from 0 minutes to about 20 minutes of the eluting the first eluent increases linearly from 0% to about 10% by volume, from about 20 minutes to about 50 minutes of the eluting the first eluent increases linearly from about 10% to about 20% by volume, from about 50 minutes to about 65 minutes of the eluting the first eluent increases linearly from about 20% to about 40% by volume, and from about 65 minutes to about 80 minutes of the eluting the first eluent increases linearly from about 40% to about 60% by volume; and wherein the column temperature is about 25° C.; the injection volume is about 10 µL; the flow rate is about 1 mL/minute; and from 0 minutes to about 80 minutes the pressure increases linearly from about 1,000 psi to about 3,000 psi.

The present invention is also directed to a method of screening a *Ficus* extract having angiogenesis inhibiting activity, the method comprising isolating a *Ficus* extract having angiogenesis inhibiting activity by a process of the present invention, applying the *Ficus* extract having angiogenesis inhibiting activity to a tumor, and measuring neovessel growth from the tumor.

The present invention is also directed to a pharmaceutical composition or a nutraceutical composition comprising a *Ficus* extract comprising rutin, wherein the *Ficus* extract exhibits angiogenesis inhibiting activity, and the *Ficus* extract is isolated by a process of the present invention.

In some embodiments, a composition of the present invention further comprises a pharmaceutically or nutraceutically acceptable carrier.

In some embodiments, a *Ficus* extract of the present invention is formulated into a pharmaceutical dosage form. Suitable pharmaceutical dosage forms include, but are not limited to, a tablet, a caplet, a pellet, a capsule, a gelcap, a troche, a lozenge, a syrup, a gel, an ointment, an emulsion, a patch, a solution, a dispersion, a mist, an aerosol, and combinations thereof.

In some embodiments, a *Ficus* extract of the present invention is formulated into a nutraceutical composition. In some embodiments, the nutraceutical composition is formulated into a food preparation. Suitable food preparations include, but are not limited to, a food bar, a beverage, a liquid, a solution, a suspension, a food gel, a food supplement, a powder, and a syrup. Additional suitable nutraceutical compositions include, but are not limited to a tablet, a capsule, a softgel, a gelcap, a liquid, a powder, a solution, a suspension, and a syrup.

In some embodiments, the *Ficus* extract of the present invention comprises rutin and the *Ficus* extract is substantially free from one or more of: shikimic acid, fumaric acid, syringin, chlorogenic acid, catechin, coumaric acid, psoralen, and bergapten.

Further embodiments, features, and advantages of the present inventions, as well as the structure and operation of the various embodiments of the present invention, are described in detail below with reference to the accompanying drawings.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements.

DETAILED DESCRIPTION OF THE INVENTION

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The present invention is directed to a process for isolating a natural product having angiogenesis inhibiting activity from a latex-containing portion of a *Ficus* variant. As used herein, a "*Ficus* variant" refers to a species of *Ficus* and varieties thereof, including both wild and engineered *Ficus* species and varieties thereof. In some embodiments, a *Ficus* variant is from a variety of *Ficus carica* L.). However, there are hundreds of species of *Ficus* and hundreds of varieties of *Ficus carica* that are suitable for use with the present invention. See, e.g., I. J. Condit, "Fig Varieties: A Monograph," *J. Agr. Sci.* 23:323 (1955) and A. Salhi-Hannachi et al., *Hereditas* 143:15 (2006), which disclose many *Ficus* variants, and which are incorporated herein by reference in their entirety. In some embodiments, a *Ficus* fruit is from a *Ficus carica* L. variety such as, but not limited to, gold, magnolia, louisiana, kadota, and combinations thereof.

Latex or resin is present in the fruit of the *Ficus* in small quantities. Even smaller quantities of latex can be present in the cellulosic matter of a *Ficus* variant. The present invention provides a straightforward process for isolating an extract from a *Ficus* variant that eliminates the painstaking collection of fig latex from individual fruits. Latex (i.e., resin or sap) concentration in the *Ficus* fruit is typically highest when the fruit is premature. Thus, in some embodiments, the present invention is directed to isolating an extract from a latex-containing portion of a *Ficus* variant comprising a premature *Ficus* fruit, and in particular premature fruits of *Ficus carica*. Depending on the variety and the growing region, premature fruit from *Ficus* species in the Northern hemisphere can typically be harvested between February and July.

Figure 1:
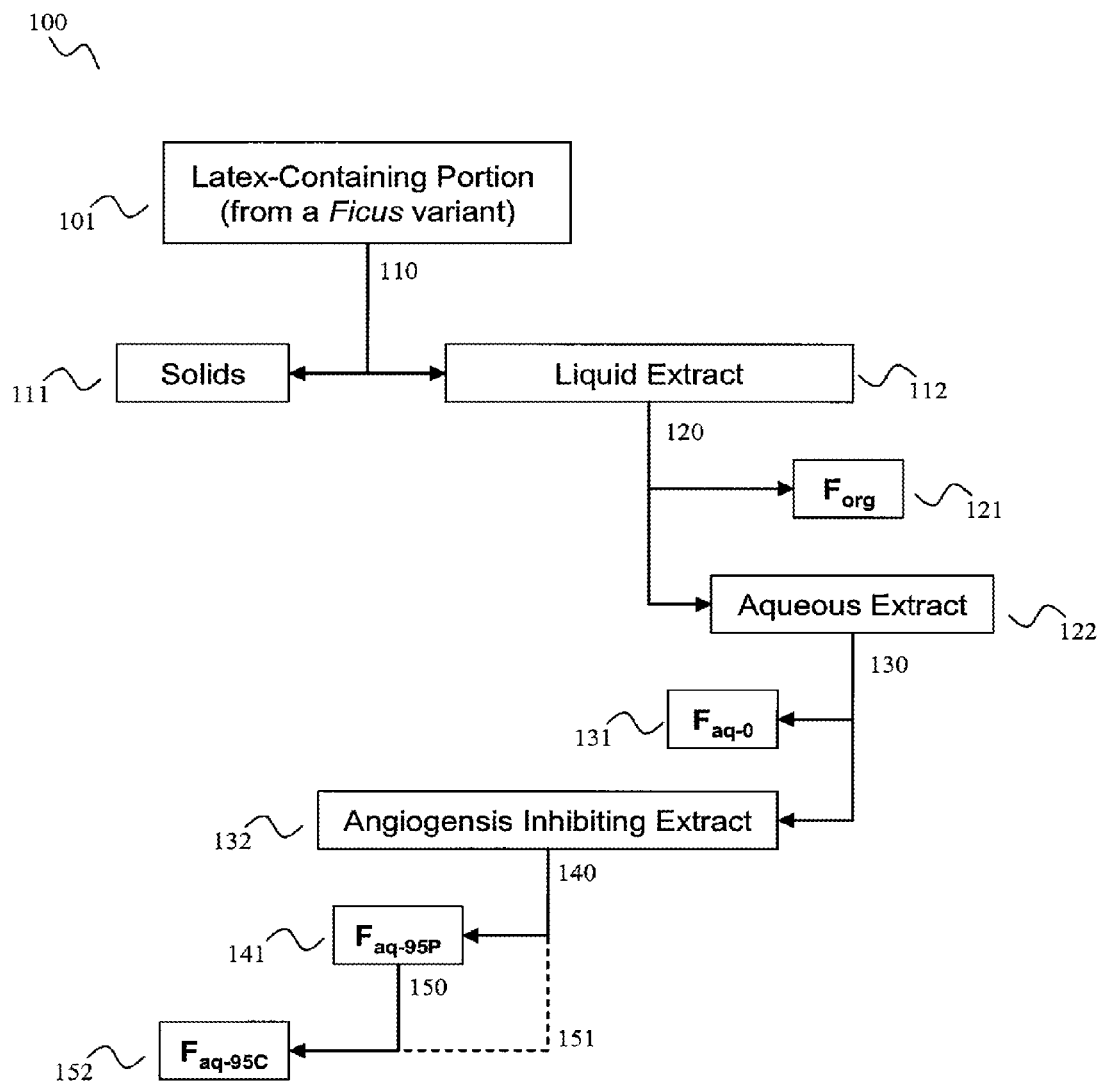
FIGS. 1 and 2 provide schematic representations of processes of the present invention for extracting and isolating an angiogenesis inhibiting extract from a *Ficus* fruit.

FIG. 1 provides a generalized schematic representation, 100, of an extraction process of the present invention. The latex-containing portion of the *Ficus* variant, 101, is placed in a polar organic solvent, and then separated, 110, into a solid fraction, 111, and a liquid fraction, 112. The liquid fraction, 112, is further separated into four major fractions. An organic fraction ($F_{org}$), 121, is isolated by washing the liquid fraction with an organic solvent, 120. The remaining aqueous fraction ($F_{aq}$), 122, is then separated into two or more fractions via column chromatography, 130, utilizing, for example, an adsorbent capable of separating species based upon relative molecular size. An aqueous eluate fraction ($F_{aq-0}$), 131, is eluted from the adsorbent using deionized water. The adsorbent is then washed with a solvent that includes an organic (e.g., a species comprising at least one carbon atom, such as an alcohol) to provide an organic eluate fraction ($F_{aq-95}$), 132. The *Ficus* extract of the present invention is present in the organic eluate fraction ($F_{aq-95}$), 132.

In some embodiments, the organic eluate fraction ($F_{aq-95}$), 132, is further purified. Referring to FIG. 1, the organic eluate fraction ($F_{aq-95}$), 132, is precipitated, 140, from alcohol to form a solid precipitate ($F_{aq-95P}$), 141. In some embodiments, precipitation, 140, can increase the purity and the potency of the angiogenesis inhibiting activity of the extract by about 20%, about 30%, about 40%, or about 50%.

Referring to FIG. 1, either of the organic eluate fraction ($F_{aq-95}$), 132, or the solid precipitate ($F_{aq-95P}$), 141, can also be optionally further purified by treating, 150 or 151, with activated carbon to provide a fraction retaining angiogenesis inhibiting activity ($F_{aq-95C}$), 152. In some embodiments, the resulting fraction ($F_{aq-95C}$), 152, can be light green, beige, light yellow, white, and/or clear in color. Thus, in some embodiments, the treating with activated carbon removes intensely colored compounds (i.e., compounds having an electronic absorption in the visible region of the spectrum) from the extract. In some embodiments, an extract of the present invention is treated with activated carbon in a weight ratio of about 100:1, about 10:1, about 5:1, about 2:1, about 1:1, about 1:2, about 1:5 or about 1:10 (extract:activated carbon, by weight). In some embodiments, the treating with activated carbon improves the purity and/or potency of the *Ficus* extract by about 20%, about 50%, about 75%, about 100%, about 150%, or about 200%.

The process of the present invention comprises mixing a latex-containing portion of a *Ficus* variant (e.g., a fruit) with a polar solvent to form a mixture comprising a liquid extract and solids. In some embodiments, the latex-containing portion can be macerated, mashed, chopped, diced, or otherwise prepared to form a pulp or slurry prior to mixing with a polar solvent. The mixing is not particularly limited by the polar solvent that is used or by the duration of the mixing.

Polar solvents suitable for use with the present invention include, but are not limited to, a $C_1$-$C_{10}$ compound having at least one heteroatom selected from: N, O, P, S, and combinations thereof. In some embodiments, the polar solvent includes at least one of: water, a $C_1$-$C_{10}$ alcohol, a $C_4$-$C_{10}$ ether, $C_3$-$C_{10}$ aldehyde, a $C_3$-$C_{10}$ ketone, a $C_2$-$C_{10}$ carboxylic acid, a $C_2$-$C_{10}$ ester, a $C_3$-$C_{10}$ amine, a $C_1$-$C_5$ amide, and combinations thereof. In some embodiments, the polar solvent comprises a polar, protic solvent (e.g., methanol). In some embodiments, the polar solvent comprises a polar, aprotic solvent (e.g., acetone). Polar solvents suitable for use with the present invention include, but are not limited to, methanol, ethanol, n-propanol, iso-propanol, a butanol, a pentanol, acetone, methyethylketone, ethylacetate, acetonitrile, tetrahydrofuran, dimethylformamide, dimethylsulfoxide, water, and combinations thereof.

In some embodiments, the polar solvent has a dielectric constant of about 5 or greater, about 10 or greater, about 15 or greater, about 20 or greater, about 25 or greater, about 30 or greater, or about 40 or greater.

In some embodiments, the polar solvent has a boiling point of about 200° C. or less, about 175° C. or less, about 150° C. or less, about 125° C. or less, or about 100° C. or less.

The concentration or amount of a polar solvent used to extract materials from a latex-containing portion of a *Ficus* variant can be varied. Generally, the ratio of a polar solvent to a latex-containing portion of a *Ficus* variant (weight to weight) is the amount of a polar solvent sufficient to extract about 75% or more, about 85% or more, about 90% or more, about 95% or more, about 97% or more, or about 99% or more of a material having angiogenesis inhibiting activity. For example, further processing of a latex-containing portion of a *Ficus* variant with an additional polar solvent after an initial extraction would provide about 25% or less, about 15% or less, about 10% or less, about 5% or less, about 3% or less, or about 1% or less of a *Ficus* extract having angiogenesis inhibiting activity in addition to that extracted by an initial extraction with a polar solvent. In some embodiments, the ratio of polar solvent to fruit is about 100:1 to about 1:100, or about 10:1 to about 1:10 by weight.

In some embodiments, a latex-containing portion of a *Ficus* variant is contacted with a polar solvent for about 15 minutes or more, about 30 minutes or more, about 1 hour or more, about 4 hours or more, about 8 hours or more, about 16 hours or more, about 24 hours or more, about 48 hours or more, or about 72 hours or more. In some embodiments, the efficiency of an initial extraction with a polar solvent can be limited by contacting for too short a time interval. The resulting liquid extract, or a solid resulting therefrom, is stable under ambient conditions for an extended period of time, for example, for at least about 1 month, at least about 6 months, at least about 1 year, or at least about 2 years.

Temperature can also be controlled during the contacting. In some embodiments, a latex-containing portion of a *Ficus* variant is contacted with a polar solvent at a temperature of about −25° C. to about 200° C., about 0° C. to about 150° C., or about 25° C. to about 100° C.

In some embodiments, the process of the present invention comprises isolating a liquid extract from the mixture comprising the liquid extract and solids. Suitable means for isolating the liquid extract include those known in the art of organic synthesis and include, but are not limited to, gravity filtration, suction and/or vacuum filtration, centrifuging, settling and decanting, and the like. In some embodiments, the isolating comprises filtering a liquid extract through a porous membrane, sponge, zeolite, paper, or the like having a pore size of about 100 µm or less, about 50 µm or less, about 20 µm or less, about 10 µm or less, about 5 µm or less, or about 1 µm or less.

A liquid extract comprises an aqueous solution that includes water present in the latex-containing portion of a *Ficus* variant (e.g., water present in a fruit, stem, or leaf) in addition to a polar solvent used for the extracting. In some embodiments the process comprises removing at least a portion of the polar solvent from the liquid extract. It is not crucial that the polar solvent be removed or completely removed from the liquid extract so long as the amount of the polar solvent remaining in the liquid extract does not negatively affect the partition of components during the washing with an organic solvent.

The method for removing the polar solvent is not particularly limited, and can include solvent evaporation at a reduced pressure (e.g., subatmospheric pressure) and/or an elevated temperature (e.g., above about 25° C.). A *Ficus* extract of the present invention is generally stable at elevated temperatures for short periods of time (e.g., at a temperature of about 100° C. or greater for a duration of about 30 minutes or less, or about 15 minutes or less). However, the present invention also includes the removal of the polar solvent (and other process steps) being conducted under controlled temperature conditions such as, but not limited to, about 120° C. or less, about 100° C. or less, about 80° C. or less, about 60° C. or less, or about 40° C. or less.

In some embodiments, it can be difficult to completely remove a polar solvent from a liquid extract by standard solvent removal procedures such as evaporation. In some embodiments, processes such as co-evaporation, lyophilization, and the like can be used to completely remove the polar solvent from a liquid fraction to form a dry powder, dry pellet, dry granulate, paste, and the like.

A liquid extract is then washed with an organic solvent. In some embodiments, washing comprises suspending a solid form of a liquid extract (e.g., a powder, pellet, granulate, etc.) in an organic solvent for a period of time followed by filtering the suspension, or alternatively, placing a solid form of a liquid extract in a filter system and rinsing with an organic solvent. In some embodiments, the liquid extract or a solid form of the liquid extract is taken up or dissolved in water (e.g., deionized water) and then washed with an organic solvent. In some embodiments, the washing includes at least one washing with an organic solvent. More than one washing step can be performed, for example, two or more washings, three or more washings, or four or more washings.

The washing is not particularly limited by the organic solvent. In some embodiments, an organic solvent suitable for washing a liquid extract is at least partially immiscible with water. As used herein, an organic solvent at least partially immiscible with water refers to an organic solvent that forms at least a partial bilayer with deionized water at about 20° C. In some embodiments, an organic solvent suitable for washing a liquid extract has a solubility in deionized water at about 20° C. of about 100 g/L or less, about 80 g/L or less, about 50 g/L or less, about 25 g/L or less, about 15 g/L or less, about 10 g/L or less, about 5 g/L or less, about 2 g/L or less, about 1 g/L or less, or about 0.5 g/L or less. Organic solvents suitable for washing the liquid extract include, but are not limited to, ethyl acetate, chloroform, methylene chloride, hexane, benzene, toluene, petroleum ether, diethyl ether, and the like, and combinations thereof.

Washing the liquid extract with an organic solvent provides an organic fraction ($F_{org}$) and an aqueous extract ($F_{aq}$). Not being bound by any particular theory, washing the liquid extract with an organic solvent is effective in extracting from the liquid extract compounds present in a liquid extract such as, but not limited to, waxes, lipids, chloroplasts and other light harvesting chromophores, sitosterol, campsterol, stigmasterol, fucosterol, fatty acids (e.g., myristic acid, palmitic acid, stearic acid, oleic acid, linoleic acid, and linolenic acid), triterpene compounds, lupeol, quercetin, and other lipophilic compounds as disclosed by W. S. Jeong and P. A. Lachance, *J. Food Chem.* 66:278 (2001), and by S. Rubnov et al., *J. Nat. Prod.* 64:993 (2001), which is incorporated by herein in its entirety.

The process of the present invention comprises fractionating the aqueous extract. Fractionating can be performed by processes such as, but not limited to: column chromatography, preparative high performance liquid chromatography ("HPLC"), reduced pressure distillation, and combinations thereof.

In some embodiments, the fractionating comprises applying the aqueous extract to an adsorbent and isolating a *Ficus* extract having angiogenesis inhibiting activity by column chromatography. In some embodiments, the aqueous extract can be purified using a chromatographic separation system comprising an adsorbent. In some embodiments, a chromatographic separation system further comprises a material in addition to an adsorbent, such as, but not limited to, a porous membrane, an ion exchange resin, a silica gel, a reverse phase silica gel, or any resin, polymer, colloid, and the like suitable for performing a separation based upon a molecular property such as, but not limited to, polarity, size, functional group, and combinations thereof.

In some embodiments, the aqueous extract is further diluted with water prior to application to an adsorbent.

In some embodiments, an adsorbent is porous. In some embodiments, a porous adsorbent has a pore size of about 20 nm or less, about 15 nm or less, about 10 nm or less, about 8 nm or less, about 6 nm or less, about 5 nm or less, about 4 nm or less, about 3 nm or less, about 2 nm or less, or about 1 nm or less. In some embodiments, a porous adsorbent has a pore size of about 0.6 nm to about 20 nm, about 0.8 nm to about 15 nm, about 1 nm to about 10 nm, about 1.5 nm to about 8 nm, about 2 nm, about 4 nm, about 6 nm, or about 8 nm.

Adsorbents suitable for use with the present invention include, but are not limited to, cross-linked styrene-divinylbenzene resins (e.g., DOWEX® OPTIPORE® Resins, The Dow Chemical Co., Midland, Mich. and AMBERLITE® XAD4, XAD16, XAD1180, and XAD1600, Rohm and Haas Co., Philadelphia, Pa.); highly cross-linked, aliphatic, or phenol-formaldehyde condensate polymers (e.g., AMBER- LITE® XAD7HP and XAD761, Rohm and Haas Co.); carbonaceous resins (e.g., AMBERSORB® 563 and 572, Rohm and Haas Co.); granular activated carbon (e.g., FILTRASORB® 300 and 400, Calgon Carbon Corp., Pittsburgh, Pa.); and combinations thereof.

An eluting solvent is applied to an adsorbent loaded with the aqueous extract to elute fractions from the adsorbent. In some embodiments, an eluting solvent is an aqueous eluent comprising water. In some embodiments, an eluting solvent is deionized (e.g., deionized water). Alternatively, the tonicity of an eluting solvent can be increased by including one or more ions, salts, and the like to an eluting solvent.

In some embodiments, an eluting solvent comprises an "organic," which as used herein refers to a liquid, solid, or gas that includes at least one carbon atom in its molecular structure. Organics suitable for use as eluting solvents include, but are not limited to, methanol, ethanol, propanol, acetone, carbon dioxide, methylethyl ketone, acetonitrile, butyronitrile, carbon dioxide, ethyl acetate, tetrahydrofuran, di-iso-propylether, ammonia, triethylamine, N,N-dimethylformamide, N,N-dimethylacetamide, and the like, and combinations thereof. In some embodiments, an eluting solvent comprises an organic and water, e.g., about 95% ethanol and about 5% water.

In some embodiments, an organic is present in an eluting solvent in a concentration of about 1% to about 99%, about 2% to about 98%, about 5% to about 95%, about 10% to about 90%, about 25% to about 75%, about 40% to about 60%, about 10% to about 99%, about 25% to about 99%, about 40% to about 99%, about 60% to about 99%, about 75% to about 99%, about 85% to about 99%, about 10% to about 95%, about 25% to about 95%, about 40% to about 95%, about 60% to about 95%, about 75% to about 95%, or about 85% to about 95%, by volume of the eluting solvent.

In some embodiments, a first eluting solvent is water, and a second eluting solvent comprises water and an organic.

In some embodiments, the aqueous extract is applied to an adsorbent and an eluting solvent of water is applied to elute from the adsorbent an aqueous eluate fraction ($F_{aq-0}$). Not being bound by any particular theory, an aqueous eluate fraction eluted from the adsorbent having an aqueous extract applied thereto can comprise protcolytic enzymes and/or active moieties having cytotoxic activity, and the like (e.g., water soluble compounds having a molecular weight of about 1,000 to about 10,000 Daltons or greater).

In some embodiments, the aqueous extract is applied to an adsorbent and an eluting solvent comprising an organic is applied to elute from the adsorbent an organic eluate fraction ($F_{aq-95}$). Not being bound by any particular theory, an eluting solvent comprising an organic is effective for eluting from an adsorbent having an aqueous extract applied thereto an organic eluate fraction (i.e., $F_{aq-95}$) comprising an extract having angiogenesis inhibiting activity.

In some embodiments, after fractionating the *Ficus* extract having angiogenesis inhibiting activity can be further purified by a process comprising at least one of filtering through activated carbon, precipitation into a solution, and combinations thereof.

The present invention is also directed to a product prepared by the process of the present invention. In some embodiments, the *Ficus* extract of the present invention is substantially free of cyclotoxic compounds. In some embodiments, the *Ficus* extract of the present invention substantially lacks cytotoxic activity. As used herein, "substantially lacks cytotoxic activity" refers to extracts that are not appreciably cytotoxic under in vitro or in vivo testing and/or administering conditions. In some embodiments, "substantially lacks cytotoxic activity" refers to extracts lacking cytotoxic activity as described in S. B. Ullman et ed., *Exp. Med. Sur.* 3:11 (1945) and S. B. Ullman et ed., *Exp. Med. Sur./0*:287 (1952), both of which are incorporated herein by reference in their entirety.

In some embodiments, the *Ficus* extract of the present invention is substantially free of anti-inflammatory compounds, and does not exhibit substantial anti-inflammatory activity. In some embodiments, an extract of the present invention is substantially free of terpenoid compounds.

In some embodiments, a *Ficus* extract of the present invention is substantially free from one or more of: shikimic acid, fumaric acid, syringin, chlorogenic acid, catechin, coumaric acid, psoralen, and bergapten. As used herein, "substantially free from" refers to a *Ficus* extract that does not contain an appreciable quantity of a compound. In some embodiments, substantially free from refers to a *Ficus* extract comprising about 5% or less, about 2% or less, about 1% or less, about 0.5% or less, about 0.2% or less, about 0.1% or less, about 0.05% or less, or about 0.01% or less of a specified compound.

A *Ficus* extract of the present invention can be characterized by analytical methods such as, but not limited to, spectroscopic methods such as, but not limited to, ultraviolet-visible spectroscopy ("UV-Vis"), infrared spectroscopy ("IR"), and the like; mass-spectrometry ("MS") methods such as, but not limited to, time-of-flight MS; quadrupole MS; electrospray MS, Fourier-transform MS, Matrix-Assisted Laser Desorption/Ionization ("MALDI"), and the like; chromatographic methods such as, but not limited to, gas-chromatography ("GC"), liquid chromatograph ("LC"), high-performance liquid chromatography ("HPLC"), and the like; and combinations thereof (e.g., GC/MS, LC/MS, HPLC/UV-Vis, and the like), and other analytical methods known to persons of ordinary skill in the art.

Not being bound by any particular theory, a *Ficus* extract of the present invention comprises one or more compounds (i.e., active moieties) having a molecular weight of about 2,000 Daltons ("Da") or less, about 1,500 Da or less, about 1,200 Da or less, about 1,000 Da or less, about 900 Da or less, about 800 Da or less, about 700 Da or less, about 600 Da or less, or about 500 Da or less. In some embodiments, a *Ficus* extract of the present invention comprises one or more compounds having a molecular weight of about 200 Da to about 2,000 Da, about 250 Da to about 1,500 Da, about 300 Da to about 1,000 Da, about 400 Da to about 2,000 Da, about 600 Da to about 2,000 Da, about 800 Da to about 2,000 Da, about 1,200 Da to about 2,000 Da, about 500 Da to about 1,500 Da, about 200 Da to about 900 Da, about 300 Da to about 900 Da, about 400 Da to about 900 Da, about 200 Da to about 800 Da, about 300 Da to about 800 Da, about 400 Da to about 800 Da, about 300 Da, about 350 Da, about 400 Da, about 450 Da, about 500 Da, about 600 Da, about 650 Da, about 750 Da, or about 950 Da.

In some embodiments, a *Ficus* extract of the present invention can be characterized by HPLC, and has a chromatograph that exhibits peaks characteristic of the *Ficus* extract. For example, in some embodiments a *Ficus* extract having angiogenesis inhibiting activity has a chromatograph having peaks at about 4.9 minutes, about 6.0 minutes, about 21.3 minutes, about 22.5 minutes, about 35.0 minutes, and about 49.7 minutes, when subjected to analytical HPLC when subjected to HPLC using a $C_{18}$ reverse phase column having an internal diameter of about 4.6 mm and a length of about 250 mm; wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

A non-limiting example of a $C_{18}$ reverse phase column suitable for use with the present invention comprises a packing material having a particle size of about 3 µm to about 5 µm, a pore size of about 100 Å, and a carbon loading of about 19%. Additional column packing materials suitable for use with the present invention include are known to persons of ordinary skill in the art, and have, e.g., a particle size of about 2 µm, to about 10 µm, about 3.5 µm, about 5 and about 7 µm; a pore size of about 50 Å to about 500 Å, about 100 Å, about 200 Å, and about 300 Å; and a carbon load of about 2% to about 20%, about 2.8%, about 8.5%, about 12%, about 15%, and about 17%.

In some embodiments, a *Ficus* extract of the present invention has a HPLC chromatograph, obtained under the conditions described herein, that comprises at least one peak of: about 3.4 minutes, about 4.8 minutes, about 18.3 minutes, about 18.6 minutes, about 19.6 minutes, about 21.7 minutes, about 22.4 minutes, about 23.2 minutes, about 24.2 minutes, about 25.5 minutes, about 26.3 minutes, about 27.1 minutes, about 27.4 minutes, about 28.3 minutes, about 29.0 minutes, about 31.0 minutes, about 32.2 minutes, about 34.0 minutes, about 35.7 minutes, about 39.6 minutes, about 41.5 minutes, about 42.2 minutes, about 47.1 minutes, about 50.2 minutes, about 50.8 minutes, and combinations thereof.

Figure 16:
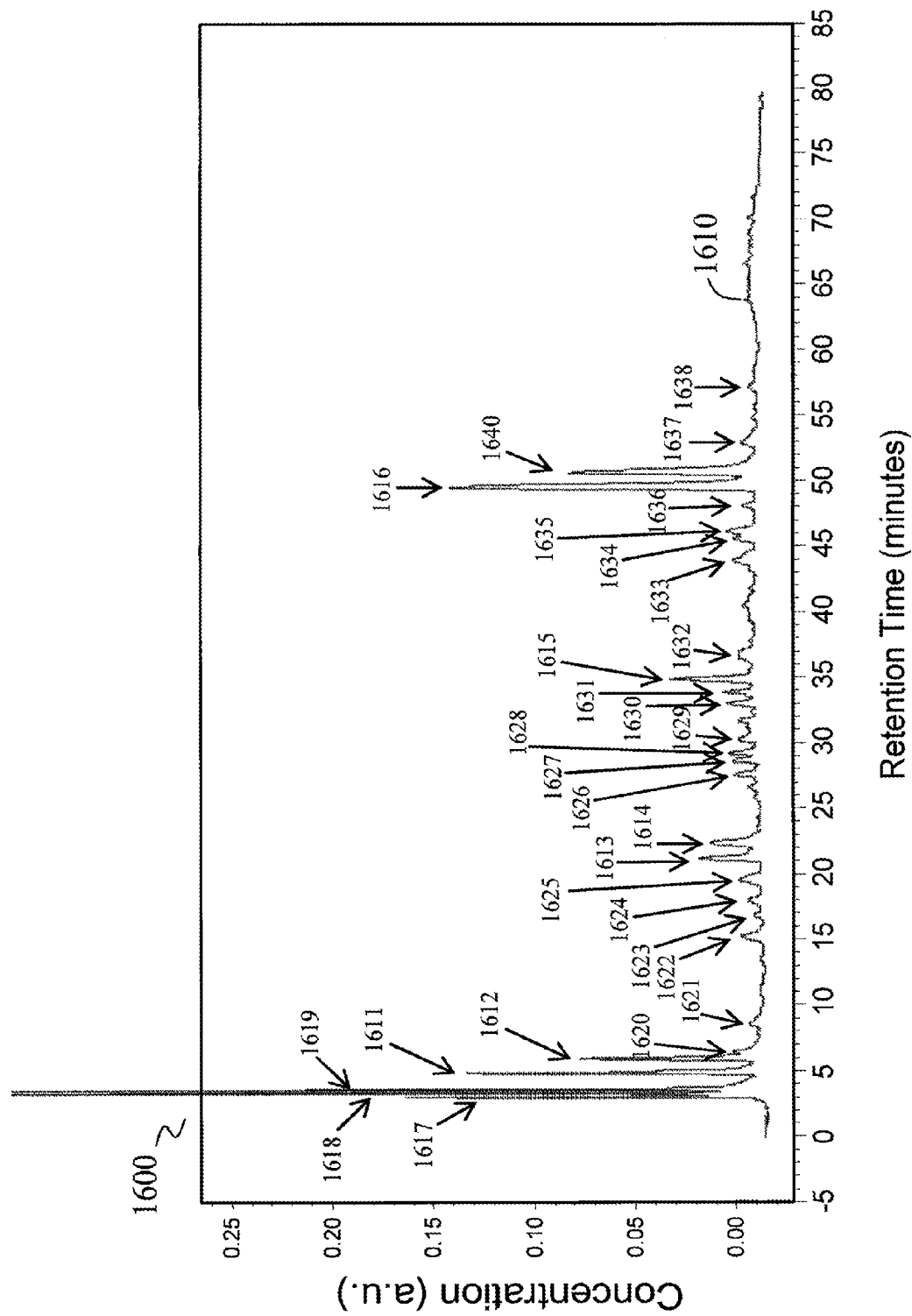
FIG. 16 provides a graphical representation of a high-performance liquid chromatograph of a *Ficus* extract having angiogenesis inhibiting activity that was isolated from a *Ficus* variant according to the present invention.

In some embodiments, a *Ficus* extract of the present invention has a chromatograph substantially in accordance with FIG. 16 (as described herein in Example 9) when subjected to HPLC using a $C_{18}$ reverse phase column having an internal diameter of about 4.6 mm and a length of about 250 mm under the conditions provided above.

In some embodiments, "substantially free from" can further be related to a HPLC chromatograph of a *Ficus* extract in which the chromatograph lacks peaks corresponding to a specified compound. For example, a *Ficus* extract of the present invention has a HPLC chromatograph, obtained under the conditions described herein, that is substantially free from one or more peaks corresponding to shikimic acid (having a retention time of about 3.6 minutes), fumaric acid (having a retention time of about 7.7 minutes), syringin (having a retention time of about 31.6 minutes) chlorogenic acid (having a retention time of about 33.3 minutes), catechin (having a retention time of about 33.3 minutes), coumaric acid (having a retention time of about 46.2 minutes), psoralen (having a retention time of about 74.1 minutes), and bergapten (having a retention time of about 79.0 minutes).

Methods of Inhibiting or Reducing Neovessel Growth and Methods of Treating

In some embodiments, the present invention is directed to a method of treating an angiogenesis dependent disease in a subject in need thereof, the method comprising: administering to a subject suffering from an angiogenesis dependent disease a pharmaceutical composition comprising a *Ficus* extract having angiogenesis inhibiting activity, wherein the *Ficus* extract is isolated from a latex-containing portion of a *Ficus* variant by a process of the present invention.

Non-limiting examples of angiogenesis dependent diseases and disorders suitable for treatment with an extract of the present invention include, but are not limited to: a cancer, an age-related macular degenerative disorder, atherosclerosis, a psoriasis, a haemangioma (e.g., an infantile haemangioma, a capillary haemangioma, or a cavernous haemangioma), a peptic ulcer, an ocular neovascularization, a rheumatoid arthritis, and combinations thereof.

As used herein, the terms "treat," "treating," and "treatment" refer to both therapeutic treatment and prophylactic or preventative measures, wherein the object is to prevent, inhibit, reverse or slow down (lessen) an undesired physiological condition, disorder or disease, or obtain a beneficial or desired clinical result. For purposes of this invention, beneficial or desired clinical results include, but are not limited to, alleviation of symptoms; diminishing the extent of a condition, disorder or disease; stabilization (i.e., not worsening) of a state of a condition, disorder or disease; delay of the onset or progression of a condition, disorder or disease; amelioration of a condition, disorder or disease state; and remission (whether partial or total) or enhancement or improvement of a condition, disorder or disease, whether detectable or undetectable. Treatment also includes, but is not limited to, eliciting a clinically significant response (e.g., a cellular response) without excessive levels of side effects. For example, treating can include decreasing the time required for a patient to recover from an angiogenesis dependent disease, decreasing, eliminating, reducing, or disabling an angiogenesis dependent disease, or alleviating or decreasing the severity of symptoms associated with a an angiogenesis dependent disease. Treatment also includes prolonging survival as compared to expected survival if not receiving treatment.

The term "subject," as used herein, refers to any mammal, including humans and non-humans, such as, but not limited to, domestic and farm animals, zoo animals, sports animals, and pets.

As used herein, "angiogenesis inhibiting activity" refers to the ability to delay, retard, slow, decrease, diminish, or otherwise inhibit neovessel growth. Any assay or testing protocol known to a person of ordinary skill in the art that is suitable for quantifying an inhibition of neovessel growth can be utilized. In some embodiments, an inhibition of neovessel growth (i.e., an angiogenesis inhibiting activity) can be determined by an in vitro test protocol, an in vivo test protocol, an animal model, an animal clinical trial, a human clinical trial, or a combination thereof. In some embodiments, the angiogenesis inhibiting activity of a *Ficus* extract of the present invention can be quantified using the in vitro testing protocols and procedures described in the Examples herein.

The term "therapeutically effective amount" as used herein refers to an amount of a *Ficus* extract sufficient to either inhibit angiogenesis or to degrade existing capillary networks. The term therefore includes, for example, an amount of a *Ficus* extract sufficient to prevent the growth of angiogenic vessels found in diseases of tumor growth, diabetic retinopathy, psoriasis, retinopathy of prematurity, and preferably to reduce by at least 50%, and more preferably to reduce by at least 90%, the amount of angiogenesis. The dosage ranges for the administration of a *Ficus* extract are those that produce the desired effect. The precise therapeutic dosage of a *Ficus* extract of the present invention that is therapeutically effective can vary between subjects (e.g., due to age, body weight, sex, condition of the subject, the nature and severity of the disorder or disease to be treated, and the like). Thus, in some embodiments a therapeutically effective amount of a *Ficus* extract of the present invention is not specified in advance of administering the *Ficus* extract to a subject in need thereof. In some embodiments, a therapeutically effective amount of a *Ficus* extract of the present invention and can be determined by a caregiver, for example, by a physician using, for example, dose titration. The dosage can be adjusted by the individual physician in the event that any complications or adverse reactions occur. Appropriate therapeutically effective amounts can also be determined readily by routine experimentation using, for example, animal models. In any event, the effectiveness of treatment can be determined by monitoring the extent of angiogenic inhibition or remission by methods well known to those in the field. In some embodiments, a therapeutically effective amount of a *Ficus* extract of the present invention comprises about 0.01 micrograms per kilogram (μg/kg) to about 20 mg/kg of body weight of a subject per day. In some embodiments, an extract is administered to a subject in a dosage of about 0.02 μg/kg to about 10 mg/kg, about 0.05 μg/kg to about 5 mg/kg, about 0.08 μg/kg to about 1 mg/kg, about 0.1 μg/kg to about 500 μg/kg, about 0.5 μg/kg to about 200 μg/kg, about 1 μg/kg to about 100 μg/kg, about 2 μg/kg to about 50 μg/kg, or about 5 μg/kg to about 30 μg/kg of body weight of a subject per day.

In some embodiments, a *Ficus* extract of the present invention has angiogenesis inhibiting activity in the micromolar range. As used herein, "the micromolar range" refers to an extract of the present invention that exhibits angiogenesis inhibiting activity when administered to a subject in need thereof in an amount of about 1 μmol to about 999 μmol daily dosage.

In some embodiments, a therapeutically effective amount of an angiogenesis inhibiting active agent, or of an extract comprising an angiogenesis inhibiting active agent, can be about 10 μg to about 100 mg per day. In some embodiments, a minimum therapeutically effective amount of an angiogenesis inhibiting active agent, or of an extract comprising an angiogenesis inhibiting active agent, is about 10 μg, about 20 μg, about 50 μg, about 100 μg, about 200 μg, about 500 μg, about 1 mg, about 2 mg, about 5 mg, about 10 mg, about 15 mg, about 20 mg, or about 25 mg per day. In some embodiments, a maximum therapeutically effective amount of an angiogenesis inhibiting active agent, or of an extract comprising an angiogenesis inhibiting active agent, is about 100 mg, about 90 mg, about 80 mg, about 70 mg, about 60 mg, about 50 mg, about 40 mg, about 35 mg, about 30 mg, or about 25 mg per day.

A *Ficus* extract of the present invention can be administered to a subject in need thereof systemically (e.g., intravenously or orally) or locally, (e.g., injected, applied topically, and the like). Conditions affecting specific organs such as macular degeneration and the like can be more amenable to local administration of a therapeutic agent because a high local concentration of the therapeutic agent can be achieved, which can also, for example, avoid possible side effects that can arise due to systemic administration of a therapeutic agent.

In some embodiments, a method of treating an angiogenesis dependent condition further comprises administering a *Ficus* extract of the present invention with an another active agent either in the same dosage form or in separate and/or divided dosage forms.

The present invention is also directed to methods of reducing or inhibiting neovessel growth in a human or mammal, the method comprising administering a composition comprising an angiogenesis inhibiting *Ficus* extract from a latex-containing portion of a *Ficus* variant to a human or animal in need thereof.

In some embodiments, the neovessel growth that is inhibited and/or reduced can be associated with an angiogenesis-dependent disease, such as those listed herein. Thus, in some embodiments the present invention is directed to a method of inhibiting or reducing neovessel growth associated with an angiogenesis-dependent disease in a human or animal in need thereof, the method comprising: administering to the subject a composition comprising a *Ficus* extract having angiogenesis inhibiting activity, wherein the extract is isolated from a latex-containing portion of a *Ficus* variant by a process of the present invention.

Inhibition and/or reduction of neovessel growth can be quantified using statistical methods known to persons of ordinary skill in the art, and as described herein. In some embodiments, an inhibition or reduction of neovessel growth comprises the inhibition of new blood vessel growth in a anatomical region of interest, such as, but not limited to, the eye (e.g., a subconjunctival region of an eye, and the like), the mouth, the tongue, the esophagus, the stomach, the intestine, the colon, the rectum, the skin (e.g., the cutaneous, subcutaneous, and/or endometrial regions of the skin), the liver, the pancreas, the kidney(s), the bladder, the prostate gland, the thyroid gland, the lungs, the breast, the ovary(ies), the testicles, the brain, or a tumor associated therewith, and combinations thereof.

In some embodiments, angiogenesis inhibiting activity is exhibited as an inhibition or a reduction of neovessel growth in an in vitro model such as, but not limited to, a tumor fragment, a placental sample, and the like. In some embodiments, angiogenesis inhibiting activity is exhibited as an inhibition or a reduction of neovessel growth in a human or animal subject in need thereof.

In some embodiments, administering a *Ficus* extract of the present invention to a subject inhibits neovessel growth in a tissue of a human or animal body, or a tumor associated therewith, by about 10% or more, about 20% or more, about 30% or more, about 50% or more, about 75% or more, about 80% or more, about 85% or more, about 90% or more, or about 95% or more compared to a subject having a similar condition that is not treated with the *Ficus* extract.

In some embodiments, a *Ficus* extract of the present invention inhibits neovessel growth in a tissue of a human or animal body, a tumor associated therewith, or an in vitro tissue sample taken therefrom, by about 10% or more, about 20% or more, about 30% or more, about 50% or more, about 75% or more, about 80% or more, about 85% or more, about 90% or more, or about 95% or more compared to a tissue or tumor that is not treated with the *Ficus* extract.

Compositions Comprising the *Ficus* Extracts

A *Ficus* extract of the present invention can be administered to a subject (e.g., a human or animal) in need thereof in a variety of forms such as, but not limited to, a nutraceutical composition and a pharmaceutical composition (i.e., a pharmaceutically acceptable dosage form).

As used herein, a "nutraceutical composition" refers to any substance that may be considered a food or part of a food and provides medical or health benefits, including the prevention and treatment of disease. In some embodiments, a nutraceutical composition is intended to supplement the diet and contains at least one or more of the following ingredients: a vitamin; a mineral; an herb; a botanical; a fruit; a vegetable; an amino acid; or a concentrate, metabolite, constituent, or extract of any of the previously mentioned ingredients; and combinations thereof.

In some embodiments, a nutraceutical composition of the present invention can be administered as a "dietary supplement," as defined by the U.S. Food and Drug Administration, which is a product taken by mouth that contains a "dietary ingredient" such as, but not limited to, a vitamin, a mineral, an herb or other botanical, an amino acid, and substances such as an enzyme, an organ tissue, a glandular, a metabolite, or an extract or concentrate thereof.

Non-limiting forms of nutraceutical compositions of the present invention include: a tablet, a capsule, a softgel, a gelcap, a liquid, a powder, a solution, a tincture, a suspension, a syrup, or other forms known to persons of skill in the art. A nutraceutical composition can also be in the form of a food, such as, but not limited to, a food bar, a beverage, a food gel, a food supplement, a powder, a syrup, and combinations thereof.

In some embodiments, a *Ficus* extract of the present invention is administered as a pharmaceutical composition to a subject (e.g., a human or animal) in need thereof. As used herein, a "pharmaceutical composition" refers to a pharmaceutically acceptable composition comprising a *Ficus* extract of the present invention. As used herein, "pharmaceutically acceptable" refers to those compounds, materials, compositions, and/or dosage forms which arc, within the scope of sound medical judgment, suitable for contact with the tissues of human beings and animals without excessive toxicity, irritation, allergic response, or other problem complications commensurate with a reasonable benefit/risk ratio. In some embodiments, the term "pharmaceutically acceptable" refers to excipients that have been approved by a regulatory agency of the Federal or a state government or listed in the U.S. Pharmacopeia or other generally recognized international pharmacopeia for use in animals, and more particularly in humans. One of skill in the art will recognize that pharmaceutically acceptable excipients can be used in the present invention including those listed in *The Handbook of Pharmaceutical Excipients,* 5th Ed., The Pharmaceutical Press and American Pharmacists Association, London, UK and Washington, D.C. (2006) and *Remington: The Science and Practice of Pharmacy*, Lippincott Williams & Wilkins, 21st Ed. (2005), which are incorporated herein by reference in their entirety.

When a *Ficus* extract of the present invention is employed as an angiogenesis inhibiting agent in a human or animal, the *Ficus* extract can be administered alone or in combination with pharmacologically acceptable carriers, the proportion of which is determined by the solubility and chemical nature of the extract or the composition, chosen route of administration and standard pharmacological or nutraceutical practice.

In some embodiments, a *Ficus* extract of the present invention is present in a nutraceutical or pharmaceutical composition in a concentration of about 0.5% to about 99%, about 1% to about 98%, about 5% to about 95%, about 10% to about 90%, about 20% to about 85%, about 50% to about 80%, or about 60% by weight of the nutraceutical or pharmaceutical composition.

In some embodiments, a nutraceutical composition or pharmaceutical composition provides a unit dosage to a subject (e.g., a human or animal) in need thereof. As used herein, a "unit dosage" refers to an amount of a *Ficus* extract of the present invention that is sufficient for once-daily, twice-daily, thrice daily, four-times daily dosing, each dose of which is administered as a single unit. Representative unit dosage forms of the present invention include, but are not limited to, a tablet, a capsule, a packet, a lozenge, and the like.

Pharmaceutically acceptable dosage forms of the present invention include, but are not limited to, oral, parenteral, transmucosal, transdermal, sublingual, intraocular, and pulmonary dosage forms comprising an extract from a *Ficus* variant, in particular varieties of *Ficus carica* L. For example, suitable pharmaceutically acceptable dosage forms include, but are not limited to, tablets, caplets, pellets, capsules, shear-form matrices, gelcaps, troches, lozenges, syrups, gels, ointments, emulsions, patches, solutions, dispersions, mists, aerosols, and the like that contain a therapeutically effective amount of a *Ficus* extract of the present invention. Parenteral infusions include intramuscular, intravenous, intraarterial, or intraperitoneal administration.

For example, a *Ficus* extract of the present invention can be orally administered in the form of a tablet, a capsule, a lozenge, a syrup, a mist, an aerosol, a troche, a strip, a suspension, a solution, and the like containing excipients such as, but not limited to, starch, milk, sugar, certain types of clay, coloring and flavoring agents, as well as optional dispersants, solubilizers, and the like. A *Ficus* extract can be injected parenterally in the form of a sterile solution containing other solutes; for example, saline or glucose sufficient to make a solution isotonic.

As used herein, an "excipient" refers to a pharmaceutically acceptable substance, or mixture of substances, that can be used to give desirable physical characteristics to a pharmaceutical dosage form comprising a *Ficus* extract of the present invention. Pharmaceutically acceptable excipients for use with the dosage forms include, but are not limited to, diluents, binders, disintegrants, solubilizers, extended release polymers, lubricants, preservatives, inorganic excipients, glidants, taste-masking excipients, flavorants, flavor enhancers, and sweeteners.

Dosages comprising the therapeutic *Ficus* extracts of the present invention can vary with the form of administration and the particular compound chosen. Furthermore, the dosage forms comprising the *Ficus* extracts can vary with the particular subject under treatment. For example, treatment can be initiated with small dosages substantially less than the optimum dose of a *Ficus* extract. Thereafter, the dosage is increased by small increments until an optimum effect under the circumstances is reached. In general, a *Ficus* extract of the present invention is administered at a concentration level that will generally afford effective results without causing any harmful or deleterious side effects.

Oral dosage forms containing a *Ficus* extract of the present invention can be designed to undergo efficient dissolution either immediately upon administration of the dosage form, as a function of time after administration, or as a function of location within the gastrointestinal tract. As used herein, "dissolution" refers to the process by which a *Ficus* extract dissolves into solution from a dosage form of the present invention. The dissolution rate of an angiogenesis inhibiting active agent can be measured using, for example, a USP Type I or Type II dissolution apparatus. In some embodiments, dissolution of a *Ficus* extract from a dosage form can be measured using, for example, a USP Type I or Type II Apparatus containing 0.1 N HCl with a paddle speed of 25 rpm. In some embodiments, dissolution of a *Ficus* extract from an immediate release dosage form is at least about 75% complete within about 30 minutes, at least about 80% complete within about 30 minutes, or at least about 90% complete within about 30 minutes. In some embodiments, dissolution of a *Ficus* extract from an extended release dosage form is not greater than about 15% after about 1 hour and at least about 50% complete within about 12 hours; not greater than about 25% complete after about 1 hour and at least about 50% complete within about 8 hours, or not greater than about 35% complete after about 1 hour and at least about 50% complete within about 4 hours.

In some embodiments, dissolution of a *Ficus* extract from a dosage form of the present invention can be related to pharmacokinetic parameters and/or the in vivo concentration of an angiogenesis inhibiting active agent and/or its metabolite present in the Ficus extract. The in vivo concentration of an active agent and its metabolites, as well as pharmacokinetic parameters can be determined by sampling the blood plasma of a subject after administration of the pharmaceutical dosage forms of the present invention. Pharmacokinetic parameters that can be measured include, but are not limited to $T_{MAX}$, $C_{MAX}$, $\ln(C_{MAX})$, $AUC_t$, $AUC_{INF}$, $\ln(AUC_{LAST})$ and IntraCV.

Therapeutic Packages

The present invention is also directed to a therapeutic package comprising a Ficus extract enclosed within a container. The container is suitable for maintaining the stability of the Ficus extract for an extended period of time during storage, shipping, and administration of the Ficus extract.

As used herein, a "package" refers to a container, vessel, and the like suitable for stably containing, e.g., a pharmaceutical or nutraceutical composition comprising a Ficus extract of the present invention. A package can comprise a wrapper, a box, a bottle (i.e., a child safety bottle, a punctureable bottle, and the like), a syringe, a peelable plastic container, and the like, and combinations thereof.

The therapeutic packages of the present invention can also include a second container for storing the components (i.e., the container of unit dosages, printed matter, etc.) of the therapeutic packages. The second container can be, for example, a bag, box, envelope or any other container that would be suitable for use with the present invention. In some cases, it can be desirable to have a small second container which can be placed in a subject's luggage, pocketbook, briefcase or pocket.

Packages comprising a nutraceutical composition of the present invention further include information such as a label that clearly identifies the nutraceutical composition as not being a conventional food or a suitable sole item of a meal or diet. Information accompanying the package further comprises language representing a nutraceutical compositions as a "food" (i.e., not a "drug" or pharmaceutical), as well as identifying any additional supplement, extract, and the like present in a nutraceutical composition.

In some embodiments, a therapeutic package of the present invention further comprises a label directing administering a dosage form comprising a Ficus extract to a human or animal subject (e.g., a human or animal) in need thereof.

In some embodiments, a label can comprise printed matter. "Printed matter" can be, for example, one of a book, booklet, brochure or leaflet. Possible formats include, but are not limited to, a bullet point list, a list of frequently asked questions (FAQ) or a chart. Additionally, the information to be imparted can be illustrated in non-textual terms using pictures, graphics or other symbols. For example, printed matter can be in a form prescribed by a governmental agency regulating the manufacture, use or sale of pharmaceuticals or biological products, which notice reflects approval by the agency of the manufacture, sale, or use for human administration in treating a subject (e.g., a human or animal) in need thereof with a dosage form of the present invention. The printed matter can also contain information on the dangers associated with taking an angiogenesis inhibiting active agents and/or extracts in excessive amounts, for excessive durations, or in any manner other than that which is recommended or approved. In some embodiments, printed matter can be accompanied by a pre-recorded media device and/or a planner.

A "pre-recorded media device" can be, for example, a visual media device, such as a videotape cassette, a DVD (digital video disk), filmstrip, 35 mm movie or any other visual media device. Alternately, a pre-recorded media device can be an interactive software application, such as a CD-ROM (compact disk-read only memory) or floppy disk. Alternately, a pre-recorded media device can be an audio media device, such as a record, audiocassette or audio compact disk. The information contained on a pre-recorded media device can describe the use of a pharmaceutical dosage form of the present invention for treating a condition in a subject (e.g., a human or animal) in need thereof. A pre-recorded media device can also contain information on the dangers associated with taking an angiogenesis inhibiting active agent in excessive amounts, for excessive durations, or in any manner other than recommended or approved.

A "planner" can be, for example, a weekly, a monthly, a multi-monthly, a yearly, or a multi-yearly planner. The planner can be used as a diary to monitor dosage amounts, to keep track of dosages administered, or to prepare for future events wherein taking a regularly administered pharmaceutical dosage form of the present invention can be difficult. Alternately, the planner can be a calendar which will provide a means to monitor when a dosage has been taken and when it has not been taken. This type of planner will be particularly useful for subjects or care providers (e.g., physicians, nurses, veterinarians, and the like) having unusual schedules for administering medication to themselves (e.g., non-daily self-administration regimens) or their subjects. Additionally, the planner can be useful for the elderly, children, or other subject group who can administer medication to themselves and may become forgetful, or when multiple doses must be administered in a single 24 hour period. One skilled in the art will appreciate the variety of planning tools that would be appropriate for use with the present invention.

The following examples of extraction, isolation and screening conditions and parameters arc given for the purpose of illustrating the present invention and shall not be construed as being limitations on the scope or spirit of the invention.

EXAMPLE 1

Figure 2:
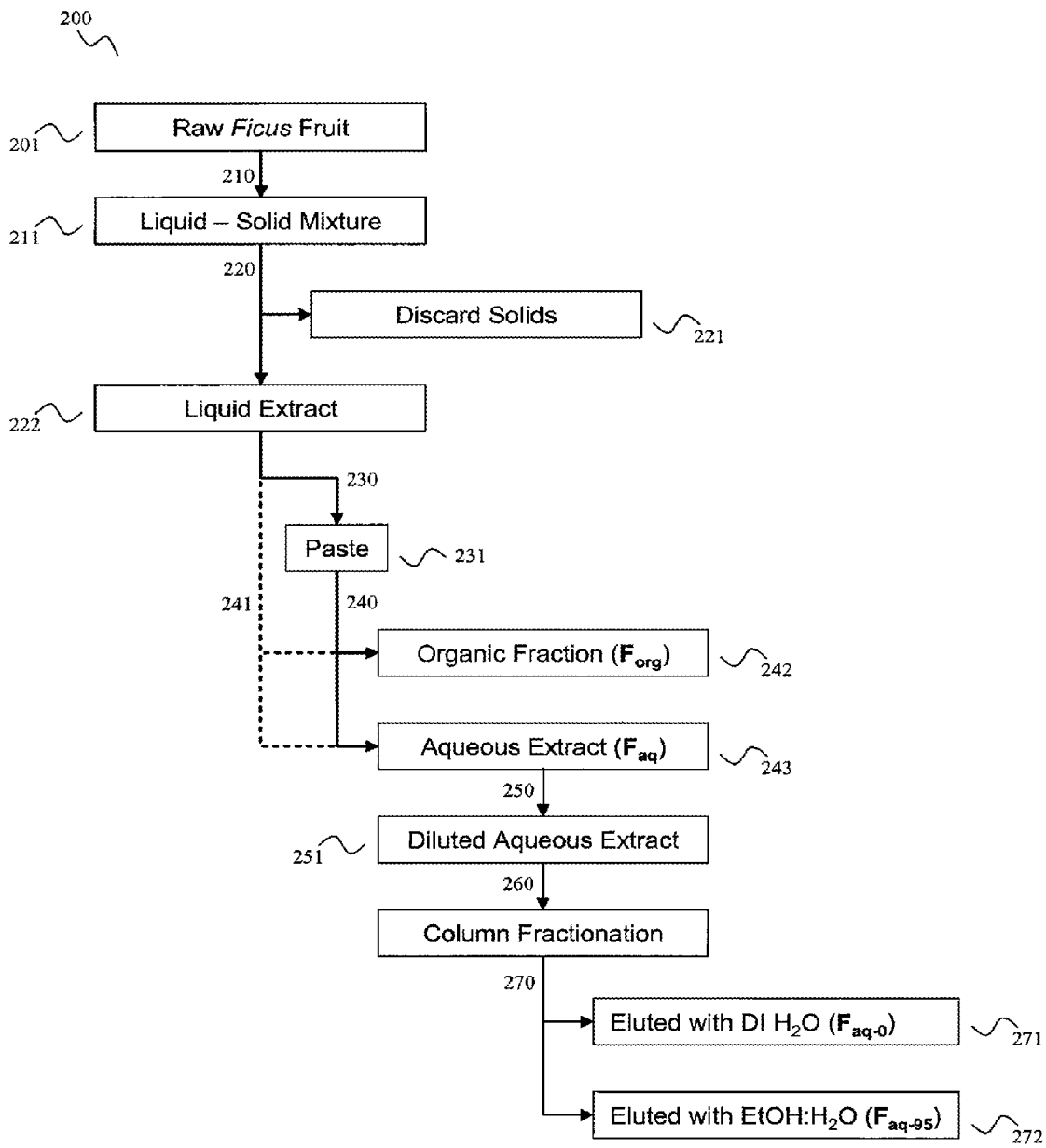

An extract exhibiting angiogenesis inhibiting activity was isolated from Ficus carica L., variety kadota. FIG. 2 provides a schematic outline of the isolation and purification process, 200. Raw fruit (fresh), 201, of Ficus carica L., variety kadota fruit (53 kg), containing approximately 82% of water and 18% solids (or approximately 9.5 kg dry weight) was macerated, 210, using a fruit chopper and mixed with a polar solvent (methanol, 130 L) for 72 hours at room temperature, to form a liquid-solid mixture, 211, having liquid and solid portions. The mixture was filtered, 220, using Whatman #4 filter paper and the solid portion, 221, was discarded. The liquid extract (approximately 230 L), 222, was then concentrated and lyophilized, 230, by first removing the polar solvent at reduced pressure using a rotary evaporator to yield a concentrated liquid extract (approximately 25 L), which was then lyophilized using a freeze drier to yield a paste (approximately 1.84 kg), 231. The ratio of dry fruit, 201, to paste, 231, was about 5:1 by weight. The paste, 231, was then suspended in deionized water (25 L), and washed with an organic solvent (ethyl acetate:deionized water, 1:1 v/v), 240. The washing was conducted three times, and after each washing the organic solvent layer was removed, and the organic solvent was evaporated at reduced pressure to yield an organic fraction, ($F_{org}$, approximately 90 g in powder form), 242. The aqueous layer (containing a small amount of ethyl acetate due to overlapping layers) was concentrated in a rotary evaporator to completely remove the water and any organic solvent, and then optionally lyophilized to yield an aqueous extract ($F_{aq}$, 1.75 kg in paste form), 243. Alternatively, the liquid extract can be washed directly with an organic solvent, 241, so long as the organic solvent used for the washing is at least partially immiscible with the liquid extract. The concentrated aqueous extract, 243, was further purified by diluting with deionized water, 250, to provide a diluted aqueous extract (having a volume of about 20 L), 251, which was then applied, 260, to a column (8" diameter×48" length) packed with an adsorbent cross-linked styrene-divinylbenzene resin (15 kg of DOWEX®OPTIPORE® 493, The Dow Chemical Co., Midland, Mich.). The diluted aqueous extract was passed through the column, 270, to yield an eluate (approximately 20 L) and the column was then washed with additional deionized water (5 L). The deionized water eluates were combined to yield a purified aqueous fraction ($F_{aq-0}$). The purified aqueous fraction was concentrated using a rotary evaporator and lyophilized to yield a paste product (1.4 kg), 271. An eluting solvent comprising an organic (ethanol:water, 95:5 v/v, 20 L) was then applied to the adsorbent, and eluted from the column to yield an extract that exhibited angiogenesis inhibiting activity ($F_{aq-95}$), 272. The extract was concentrated under reduced pressure and then lyophilized to yield a dry powder (350 g). The ratio of the *Ficus* extract having angiogenesis inhibiting activity ($F_{aq-95}$), 272, to the dry portion of the fresh *Ficus* fruit, 201, was approximately 1:27, and the ratio of the *Ficus* extract having angiogenesis inhibiting activity ($F_{aq-95}$), 272, to the total weight of the fresh fruit, 201, was approximately 1:151.

EXAMPLE 2

An extract exhibiting angiogenesis inhibiting activity was isolated from *Ficus carica* L., variety gold, by the procedure outlined in Example 1.

EXAMPLE 3

An extract exhibiting angiogenesis inhibiting activity was isolated from *Ficus carica* L., variety magnolia, by the procedure outlined in Example 1.

EXAMPLE 4

An extract exhibiting angiogenesis inhibiting activity was isolated from *Ficus carica* L., variety louisiana, by the procedure outlined in Example 1.

EXAMPLE 5

The *Ficus* extracts isolated by the procedure outlined in Examples 1-3 were screened for angiogenesis inhibiting activity by the following protocols.

Discarded portions of fresh human placenta were obtained anonymously with the approval of the Louisiana State University Health Sciences Center's Institutional Review Board (New Orleans, La.). Tissues were obtained and transported to the laboratory in a saline-soaked gauze pad. Dissected placental veins were trimmed of placental tissue and adventitia, and then opened longitudinally to produce a flat film having a full thickness of venous tissue.

Figures 3A, 3B:
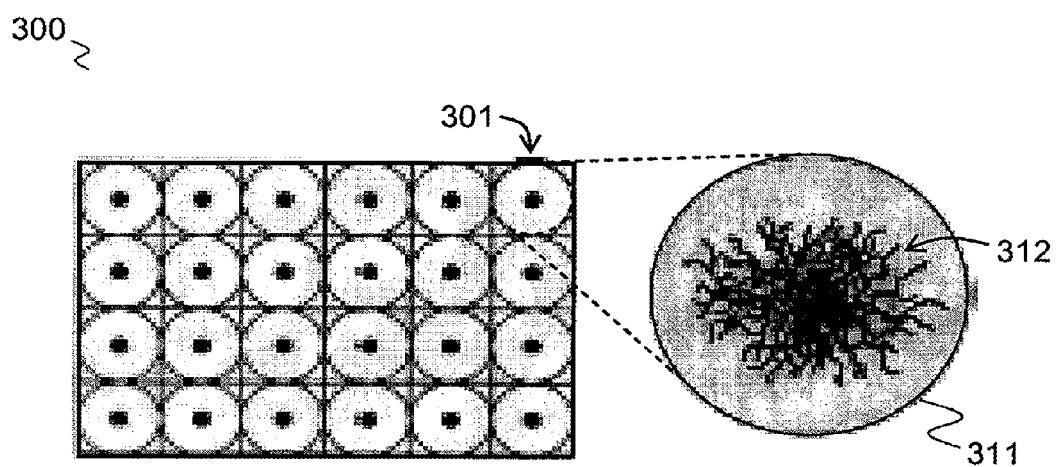
FIGS. 3A-3B and 4A-4B provide schematic representations of an angiogenesis inhibition screening process of the present invention.

A schematic representation of the angiogenesis assay is depicted in FIGS. 3A and 3B. Discs were prepared from the placental veins using a sterile 0.2 mm diameter skin punch. Referring to FIG. 3A, the placental discs were allocated to wells in a 96-well plate (Corning Inc., Corning, N.Y.), 300, in a pattern designed to minimize inclusion of one section of the placenta into a specific treatment group. All wells, 301, were preloaded with thrombin solution (0.05 IU in 1.0 μL/well) (Sigma Chemical Co., St. Louis, Mo.). Wells were allowed to evaporate to dryness.

A fibrin-thrombin clot was created in each well by covering the discs with 100 μL of a clot-forming medium comprising human fibrinogen (3 mg/mL) and ∈-aminocaproic acid (5.0%) (M-199, Sigma) in HPVAM medium. The HPVAM medium comprised Medium 199 and an antibiotic/antimycotic solution comprising 100 U penicillin, 100 U streptomycin sulfate, and 0.25 μg amphotericin/mL (Gibco BRL, Gaithersburg, Md.). This mixture was placed in a humidified incubator and allowed to clot at 37° C. in a 5% $CO_2$, 95% air environment. A nutrient medium (100 μL) containing the HPVAM supplemented with 20% bovine serum (Gibco BRL) was added to the tissue-containing clot. Drug-treated wells contained the nutrient medium supplemented with a *Ficus* extract of the present invention or a control compound. Each well's total volume was 200 μL. An enlargement of an individual well is schematically represented in FIG. 3B. At the center of the well, 311, the placental discs, 312, is shown with its surrounding neovessel structure.

Placental discs (30 for each dosage regimen) were treated with a nutrient medium or a *Ficus* extract-containing medium starting on the first day in culture, followed by observation of the development of an angiogenic response for 14 days. Representative in vitro concentrations of the *Ficus* extracts present in medium were about 0.001 mg/mL, 0.003 mg/mL, 0.01 mg/mL, 0.03 mg/mL, 0.1 mg/mL and 0.3 mg/mL. An additional tissue sample was incubated with gallic acid (1 mM or 3 mM) as a standard.

Figure 4A:
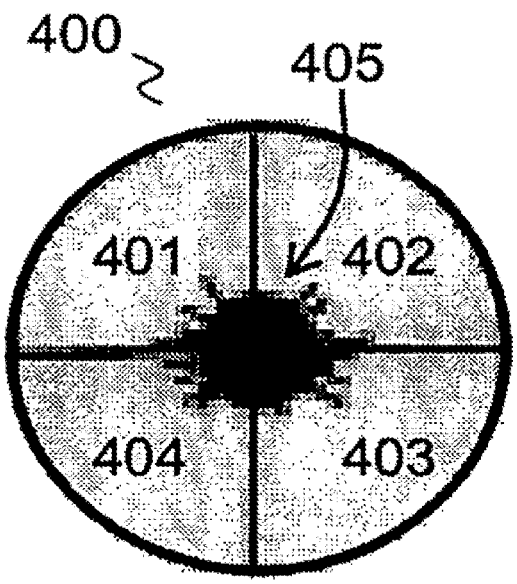
Figure 4B:
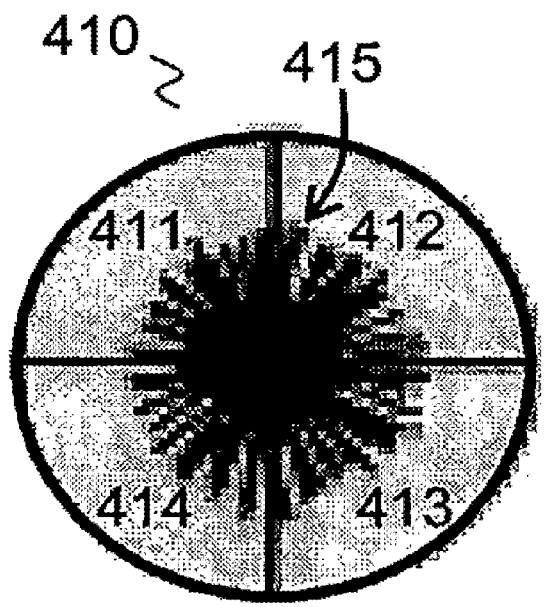
Figure 5A:
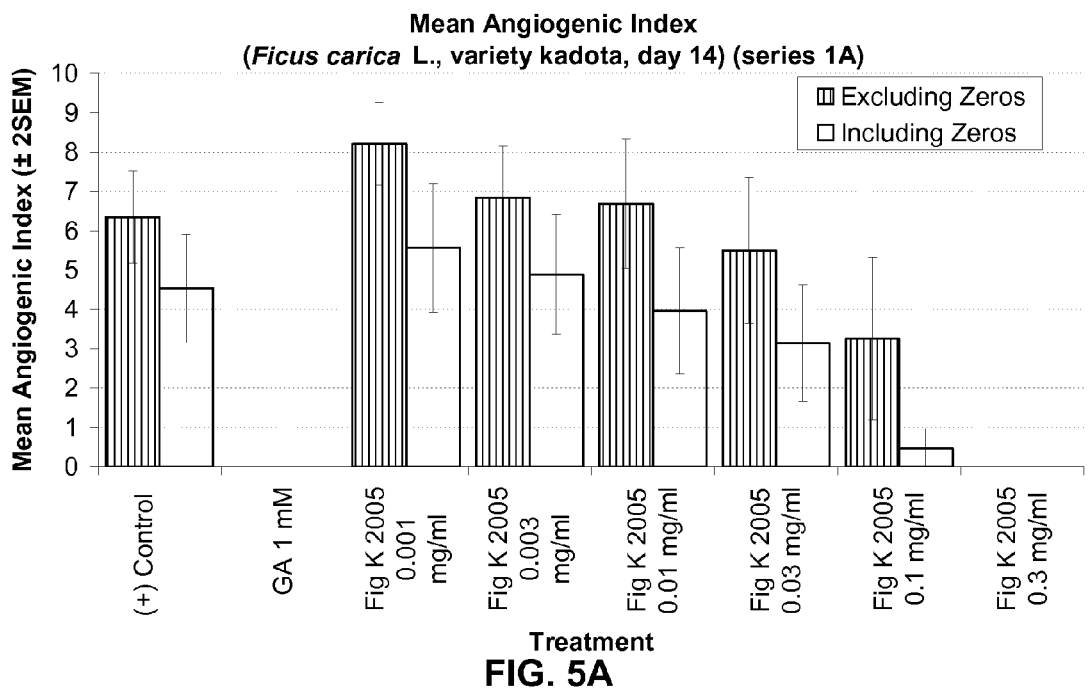
FIGS. 5A-5B; 6A-6B; 7A-7B; 8A-8B; and 9A-9B provide graphic representations of the in vitro angiogenesis inhibiting activity of extracts from *Ficus carica* L., variety kadota, at concentrations of 0.001 mg/mL, 0.003 mg/mL, 0.01 mg/mL, 0.03 mg/mL, 0.1 mg/mL and 0.3 mg/mL, as tested by a screening method of the present invention.
Figure 5B:
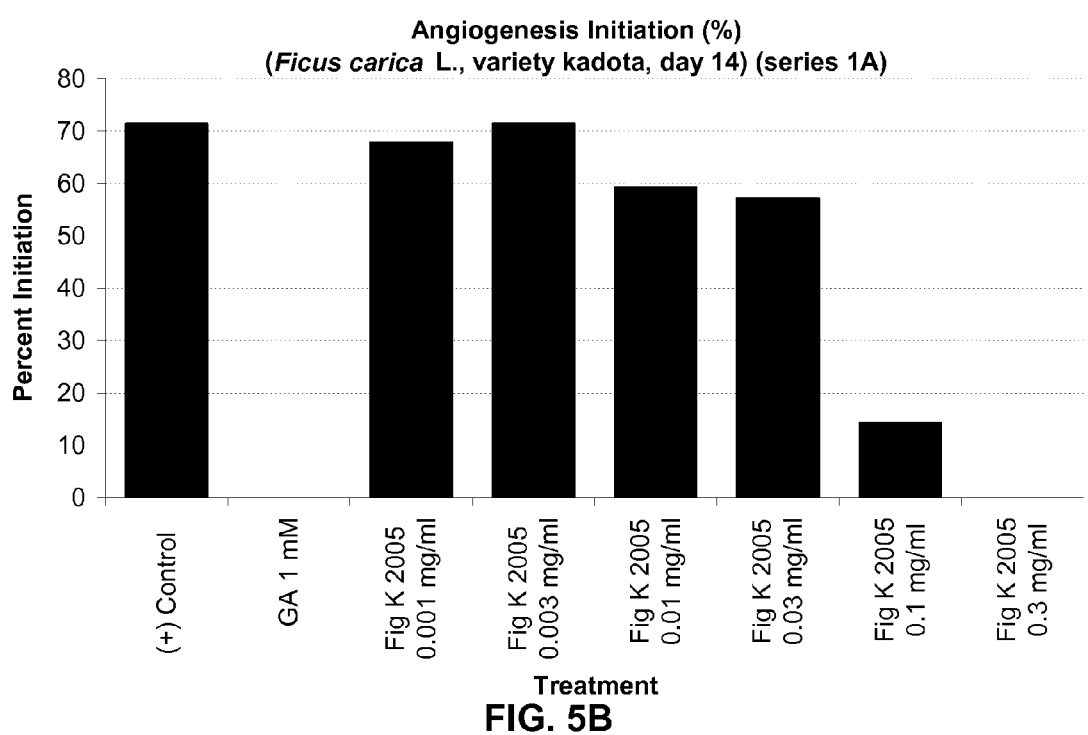
Figure 6A:
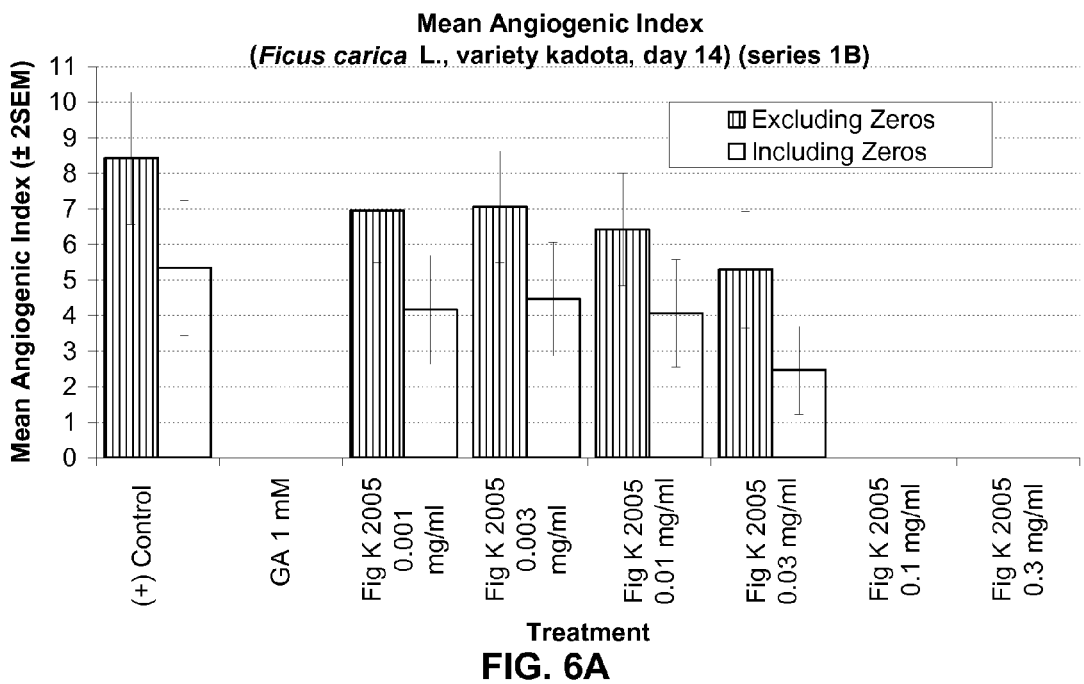
Figure 6B:
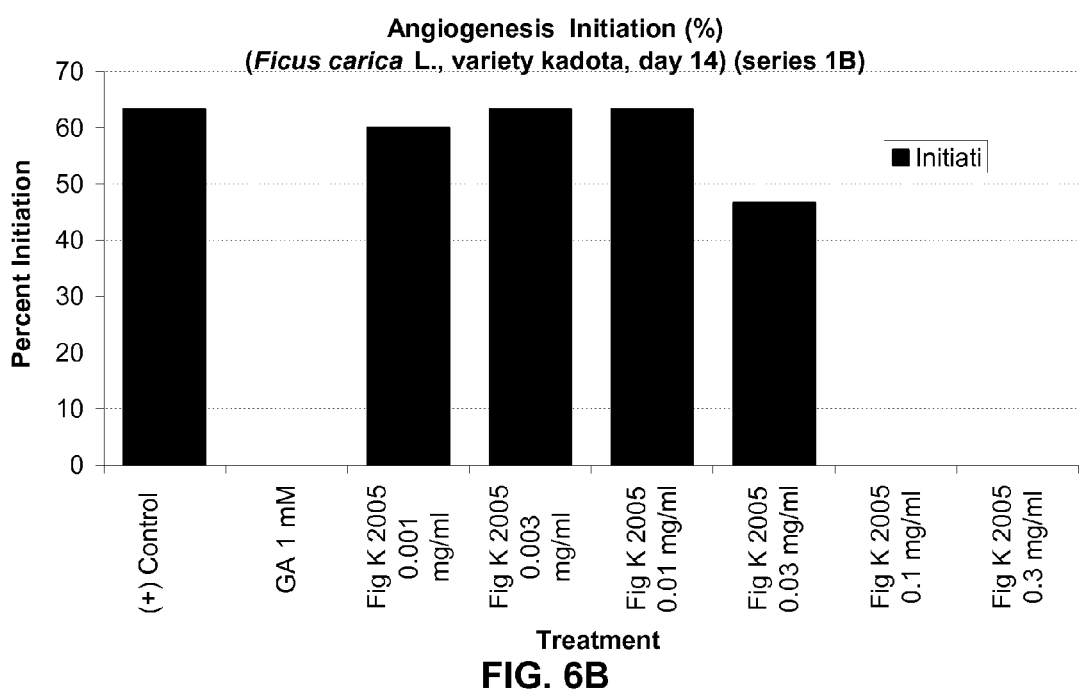
Figure 7A:
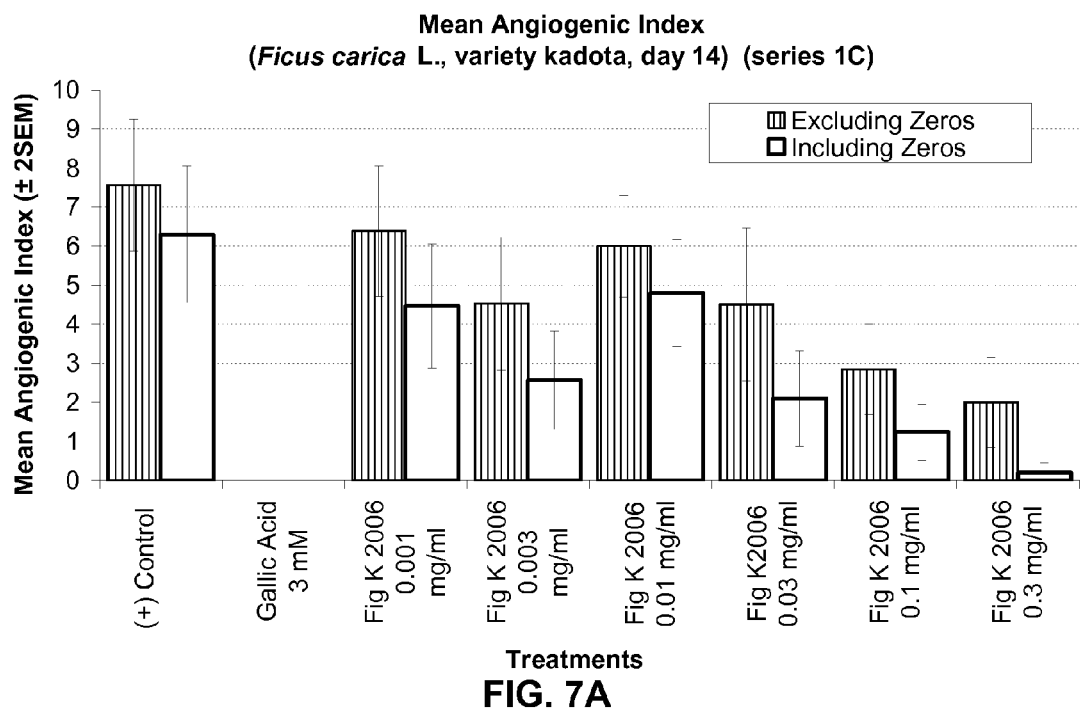
Figure 7B:
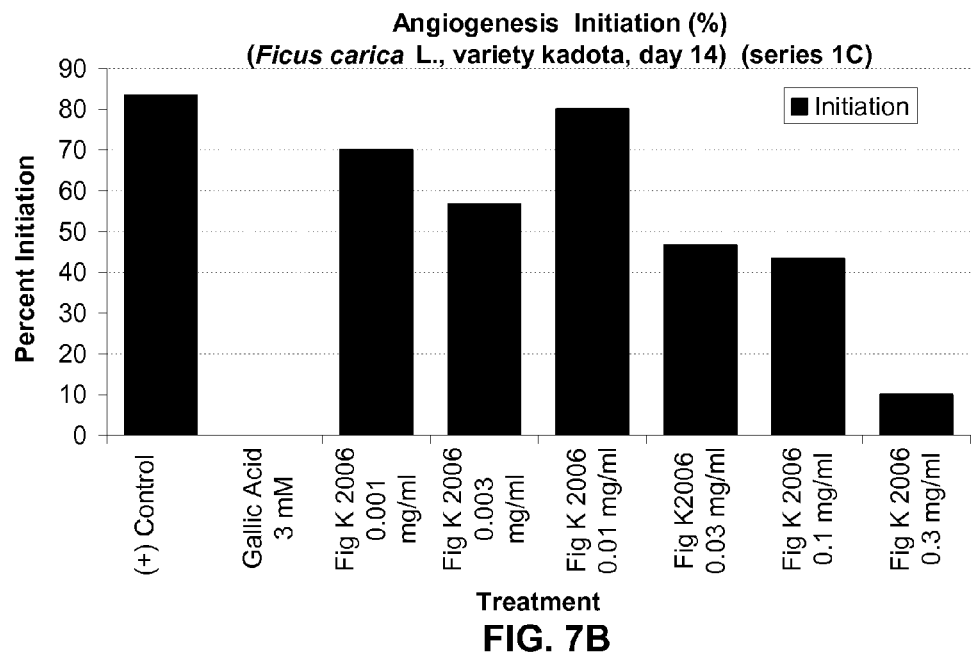
Figure 8A:
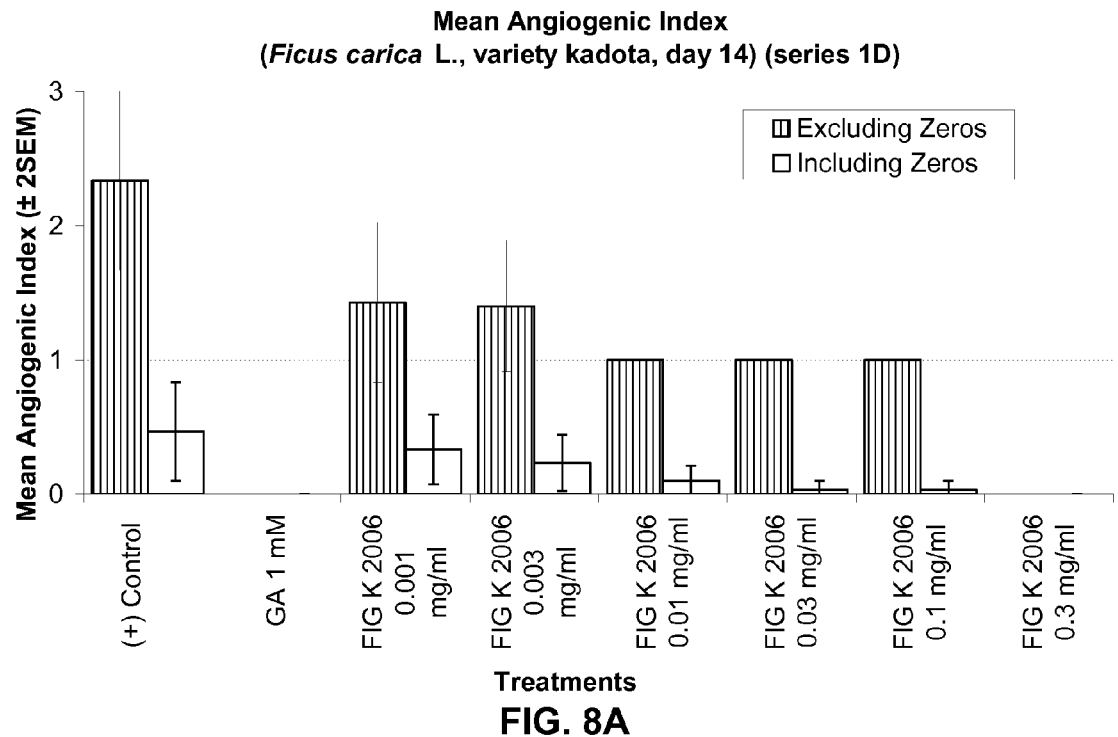
Figure 8B:
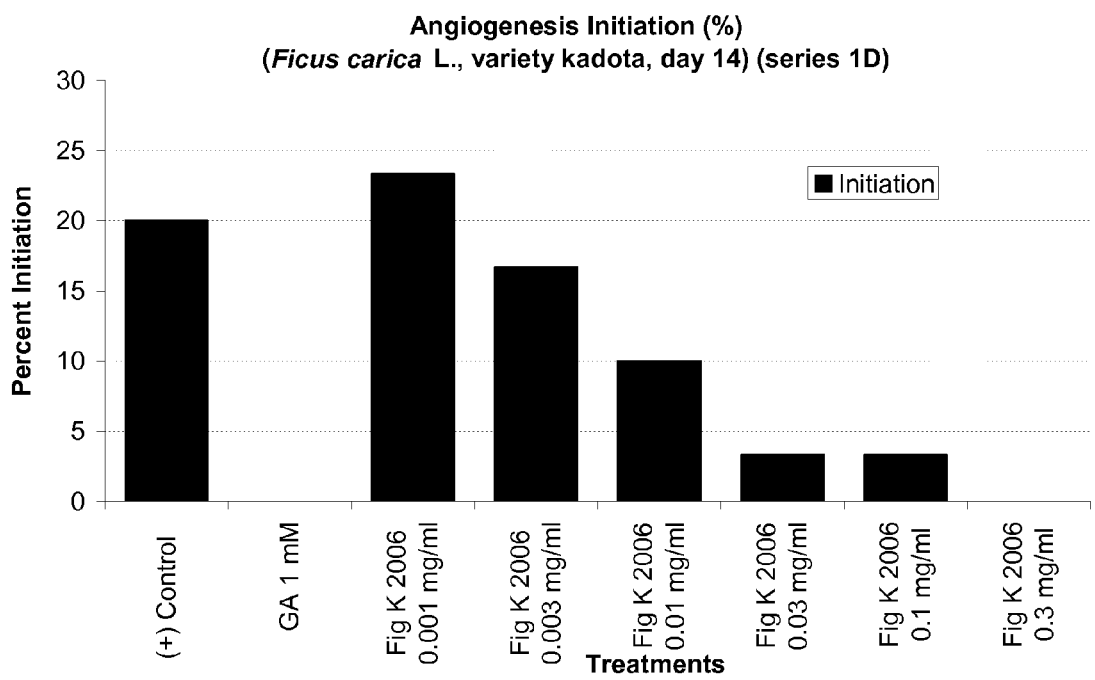
Figure 9A:
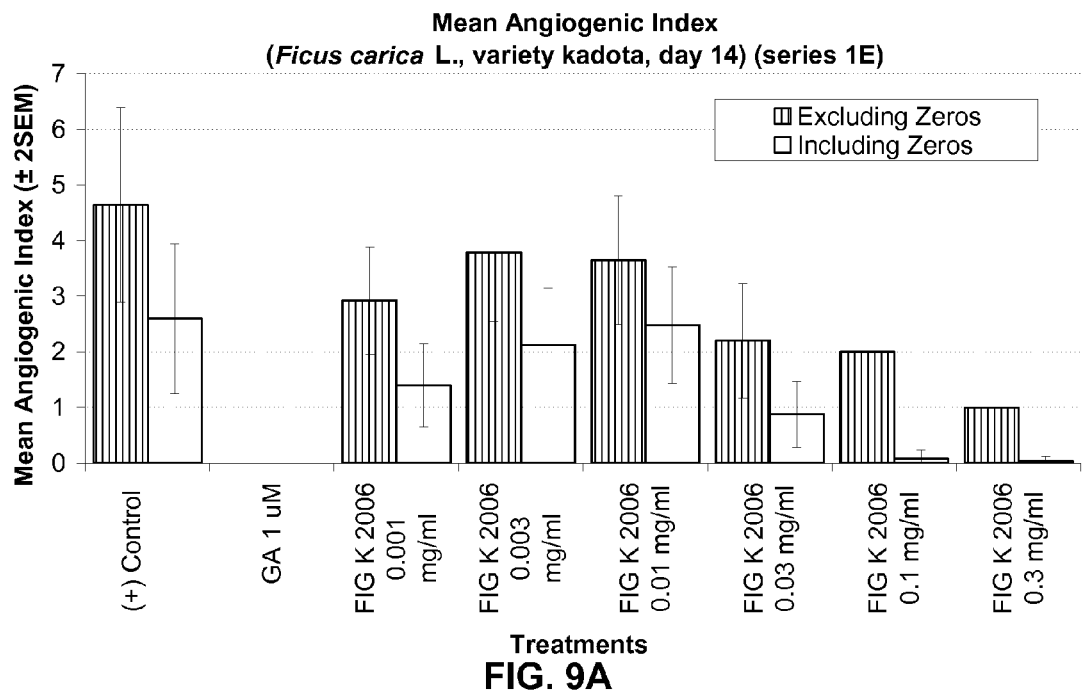
Figure 9B:
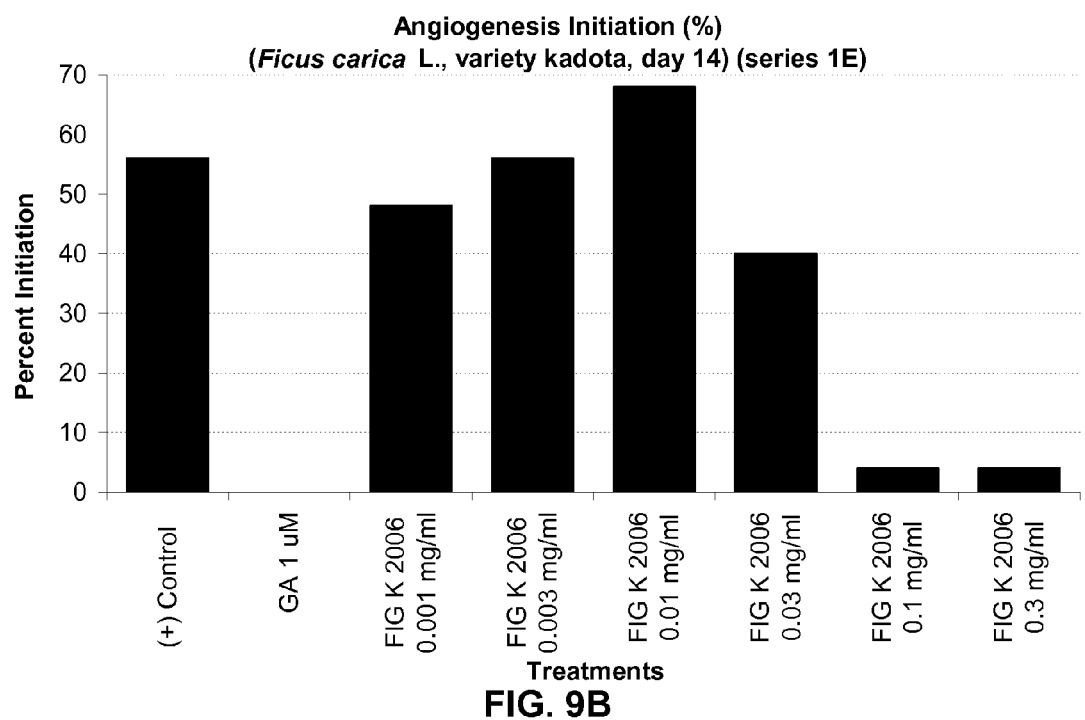
Figure 10A:
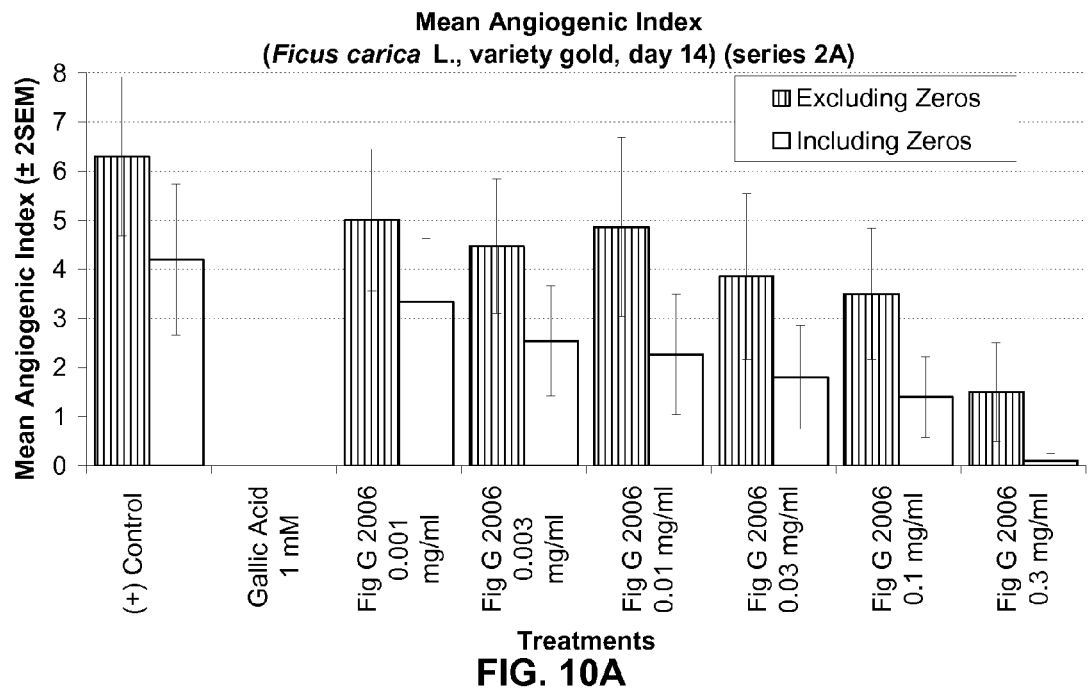
FIGS. 10A-10B; 11A-11B; and 12A-12B provide graphic representations of the in vitro angiogenesis inhibiting activity of extracts from *Ficus carica* L., variety gold, at concentrations of 0.001 mg/mL, 0.003 mg/mL, 0.01 mg/mL, 0.03 mg/mL, 0.1 mg/mL and 0.3 mg/mL, as tested by a screening method of the present invention.
Figure 10B:
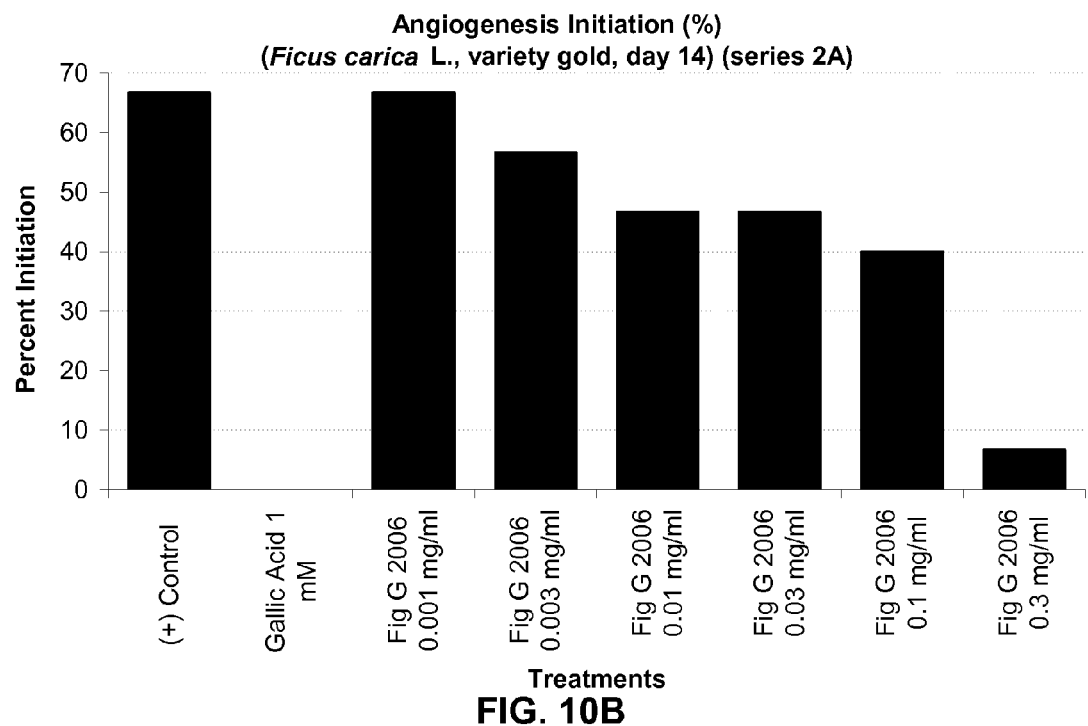
Figure 11A:
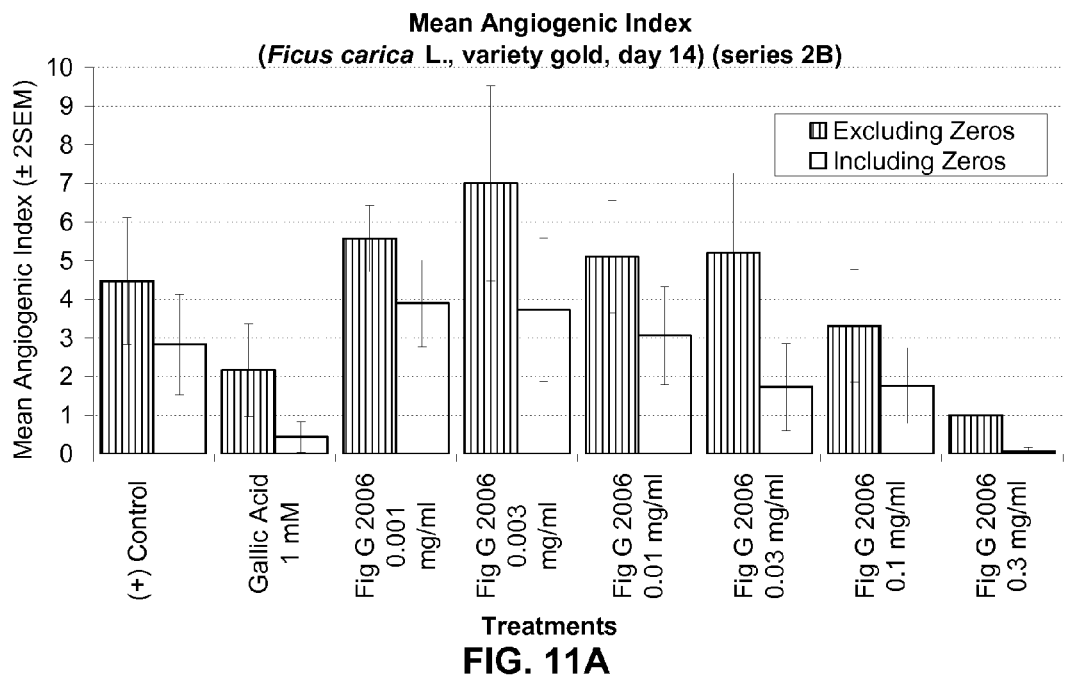
Figure 11B:
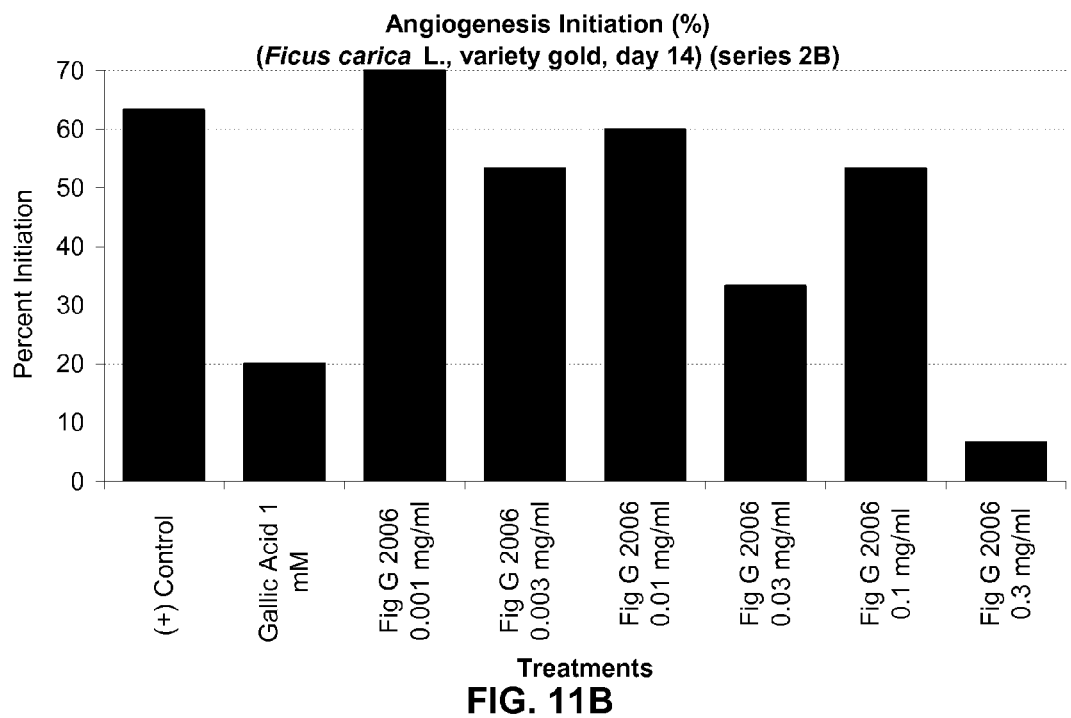
Figure 12A:
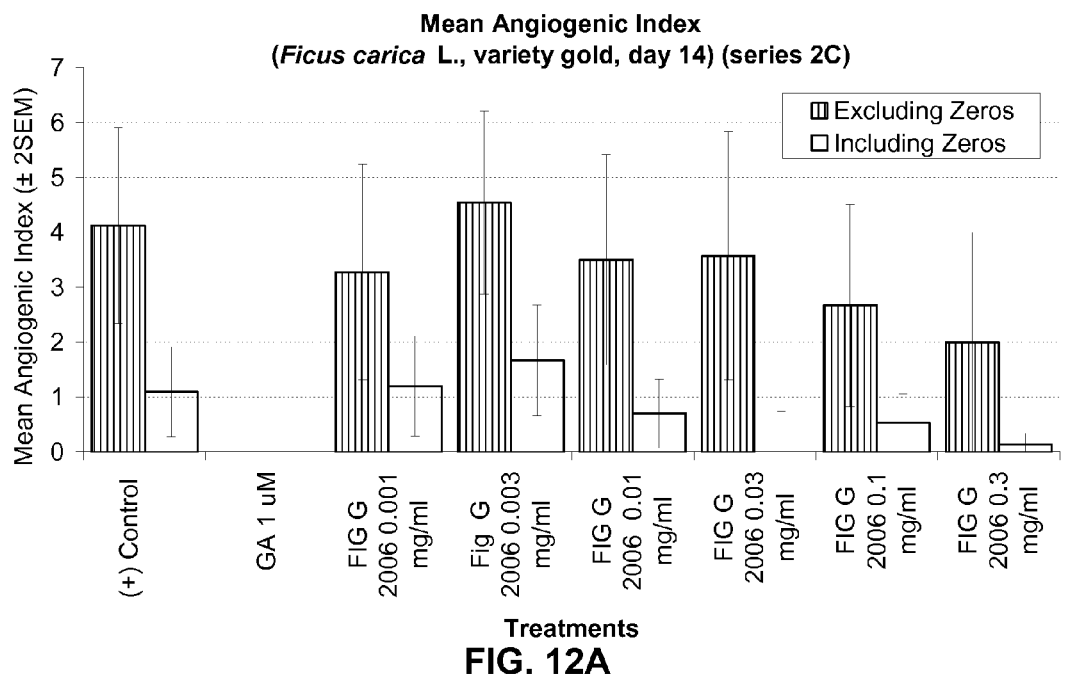
Figure 12B:
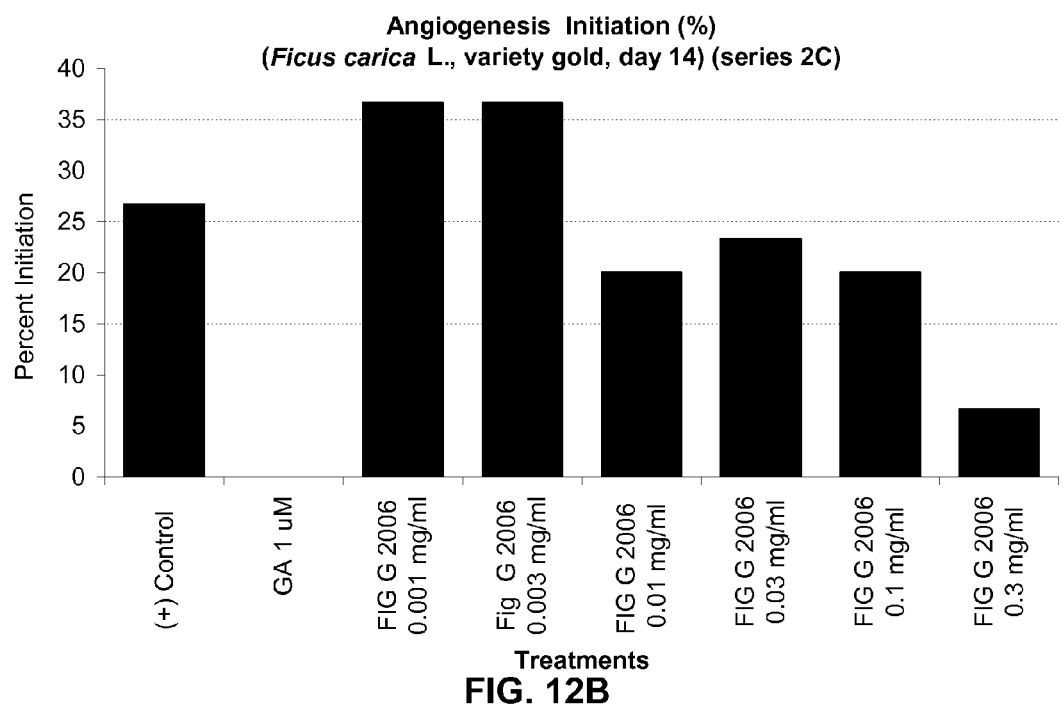
Figure 13A:
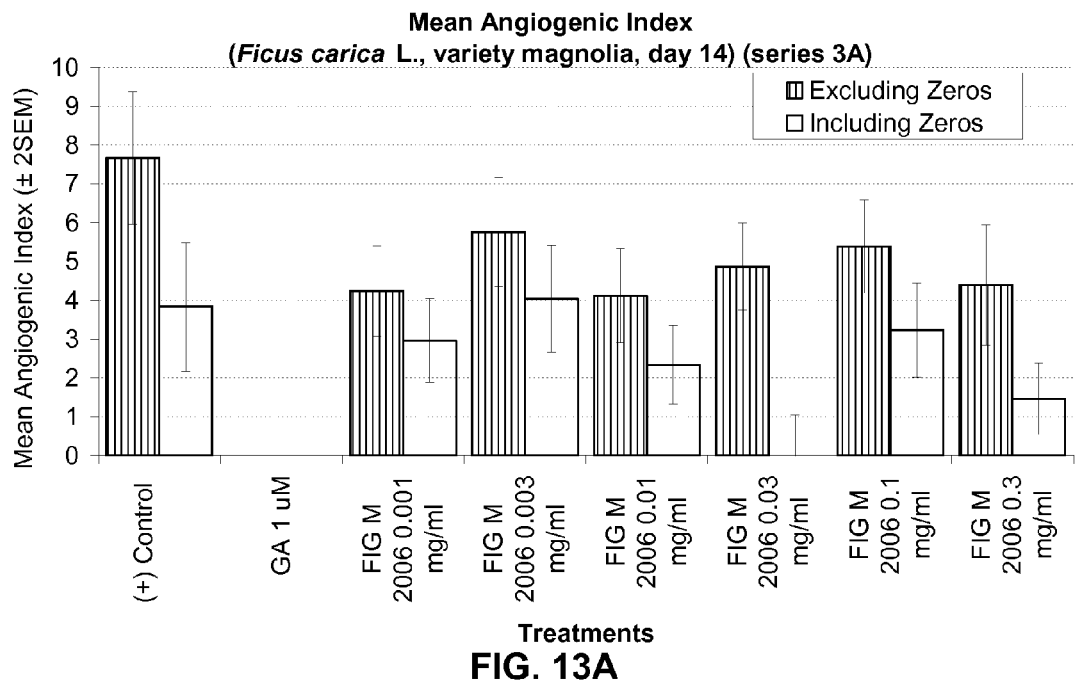
FIGS. 13A-13B; 14A-14B; and 15A-15B provide graphic representations of the in vitro angiogenesis inhibiting activity of extracts from *Ficus carica* L., variety magnolia, at concentrations of 0.001 mg/mL, 0.003 mg/mL, 0.01 mg/mL, 0.03 mg/mL, 0.1 mg/mL and 0.3 mg/mL, as tested by a screening method of the present invention.
Figure 13B:
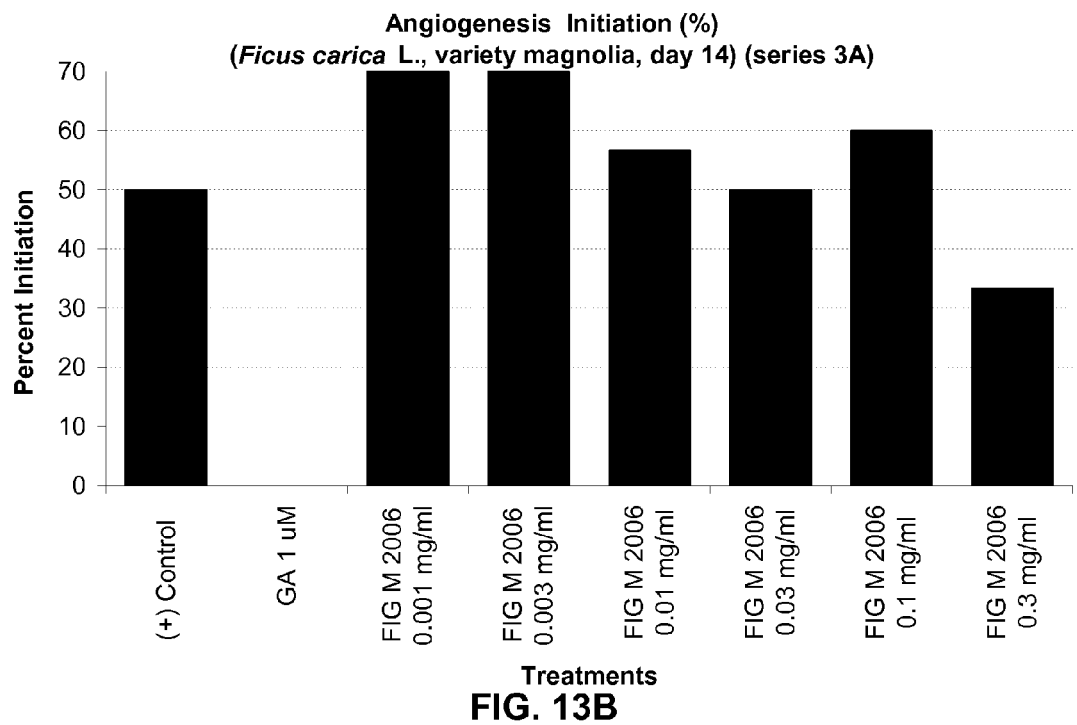
Figure 14A:
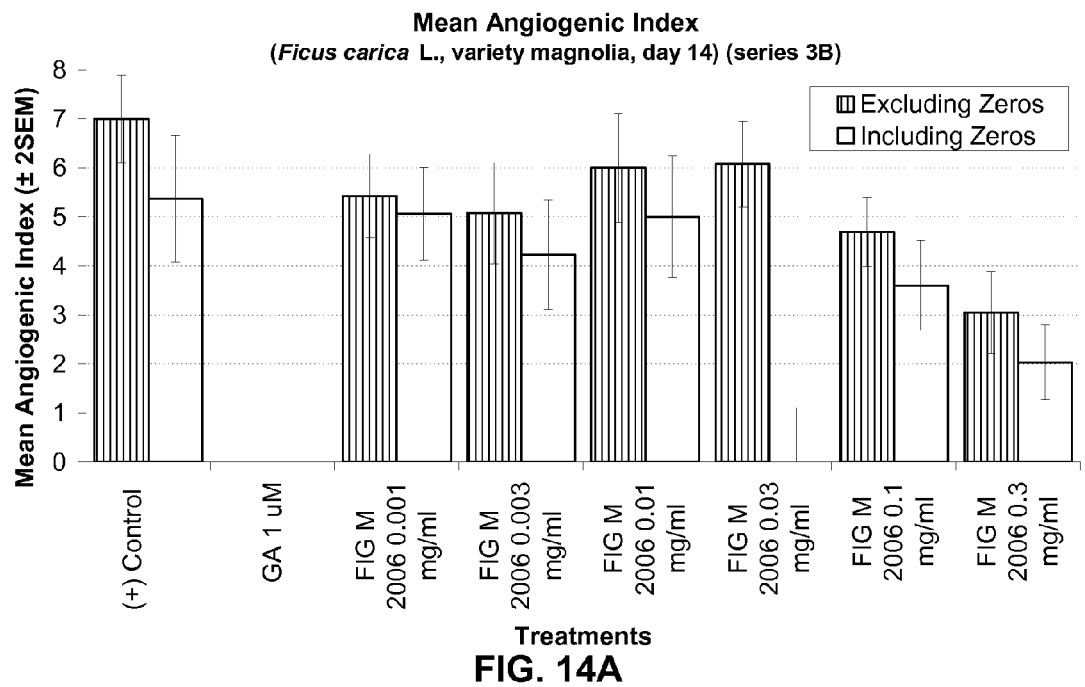
Figure 14B:
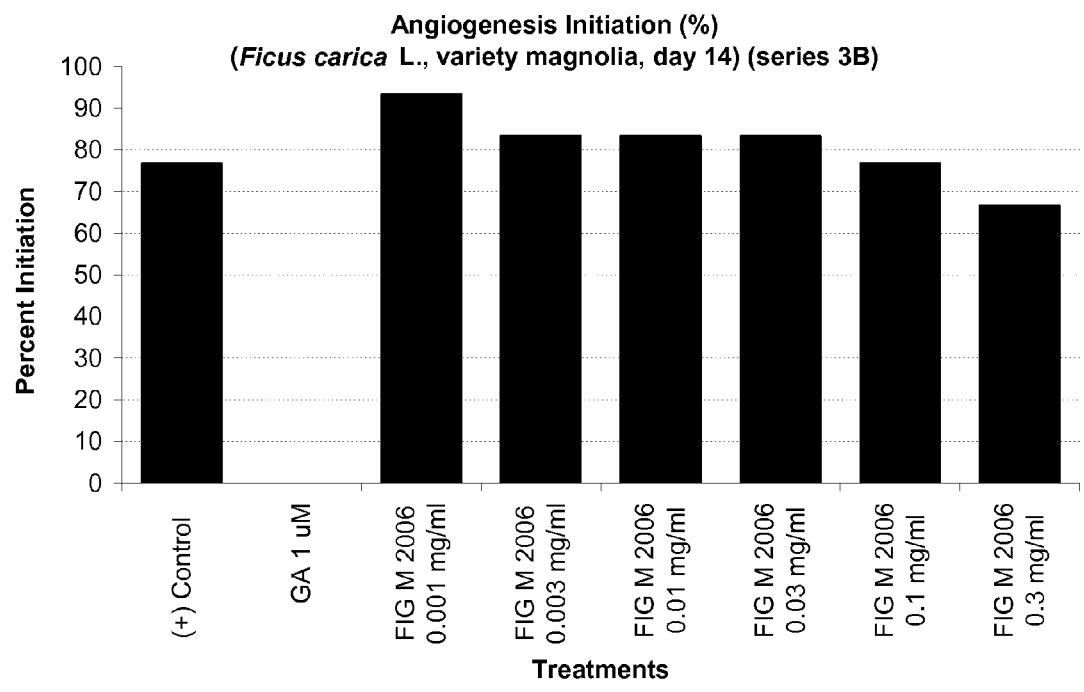
Figure 15A:
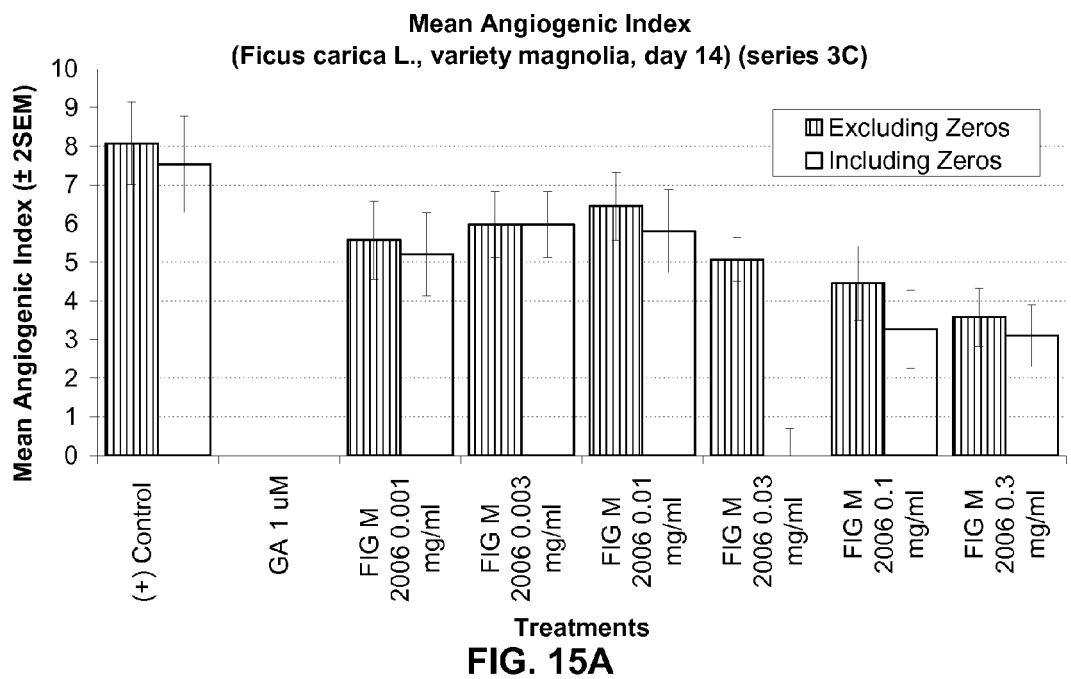
Figure 15B:
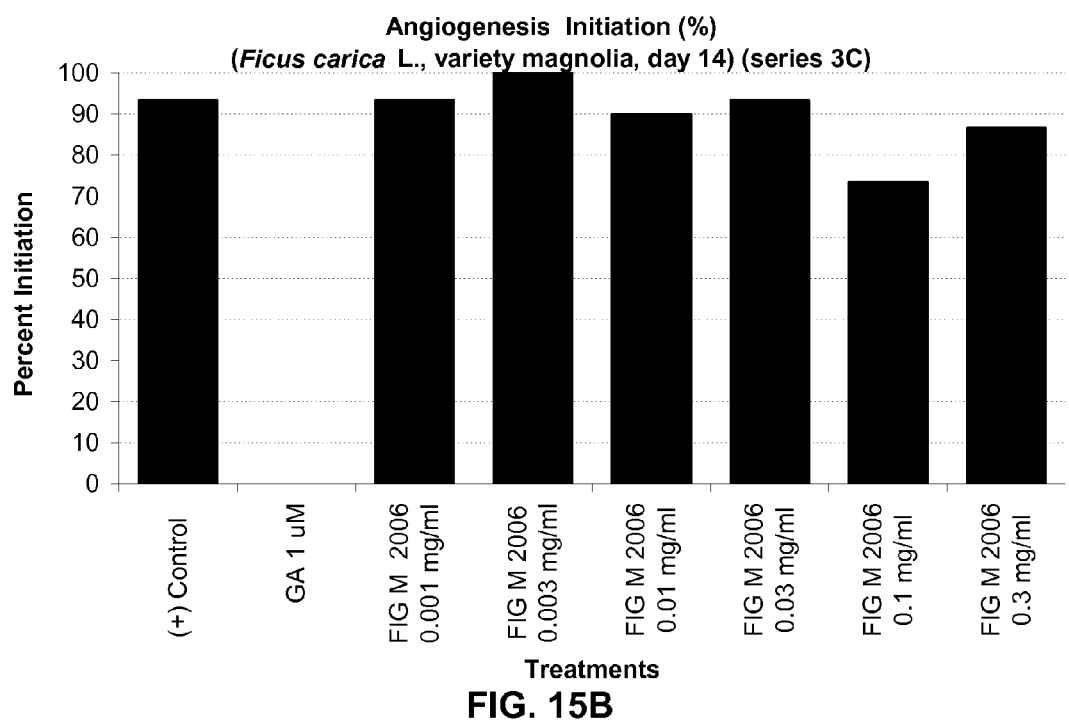

Wells were assessed for microcapillary growth on day 14 using an inverted phase microscope. Two different assay criteria were evaluated. First, the degree of angiogenic response was assessed using a semi-quantitative visual rating scale, a schematic representation of which is provided in FIGS. 4A and 4B. Referring to FIG. 4A, tissue discs, 400, were visually divided into four quadrants, 401, 402, 403 and 404. At the center of each quadrant was the placental disc with its neovascular structure, 405, penetrating into the domains of each quadrant. Each quadrant was given a numeric score from 0 to 4 based on neovessel length, density, and percentage of the quadrants' circumference involved with the angiogenic response. Numeric results from the four quadrants were summed and expressed as an Angiogenic Index ("AI", 0-16). In FIG. 4A, the quantitative score of each of the four quadrants, 401, 402, 403 and 404, is 1, giving a total mean AI of 4 (1+1+1+1=4). Referring to FIG. 4B, after treatment, the tissue disc, 410, was again measured to determine the growth of the neovessel structure, 415. In FIG. 4B, the quantitative score of each of the four quadrants, 411, 412, 413 and 414, is 4, giving a total mean AI of 16 (4+4+4+4=16). Thus, the neovessel structure in FIG. 4A resulted in an AI four times less than the neovessel structure in FIG. 4B. These AI data correlate well with more objective measures of vessel growth, such as vessel length or vessel surface area as determined by digital image analysis. At the completion of the experiment, selected wells were fixed in 10% neutral buffered formalin for hematoxylin and eosin staining or for immunohistochemical evaluation for factor VIII.

Referring to FIGS. 5A, 6A, 7A, 8A, 9A, 10A, 11A, 12A, 13A, 14A and 15A, the mean AI was calculated twice for each set of experiments. In the first calculation, "excluding zeros," quadrants exhibiting no neovessel growth (AI=0) were excluded from mean AI score. Thus, the "excluding zeros" data includes the Angiogenic Index scores from only those quadrants that exhibited neovessel growth. In the second calculation, "including zeros," neovessel growth in all quadrants is included in the mean AI score. The AI "including zeros" is a parameter that evaluates both initiation and growth, while the AI "excluding zeros" evaluates pure angiogenic growth.

Second, the ability of the preformed blood vessels to invade into the fibrin-thrombin clot was assessed over time, and the percentage of placental discs that developed invasion (% I) was calculated using the formula:

$$\frac{\text{\# of wells exhibiting invasion}}{\text{\# of wells placed}} \times 100 = \% \ I$$

The data for % I is provided in FIGS. 5B, 6B, 7B, 8B, 9B, 10B, 11B, 12B, 13B, 14B and 15B, respectively.

EXAMPLE 6

The effect on the angiogenic response of an extract from *Ficus carica* L., variety kadota, as prepared in Example 1, was evaluated by the procedure of Example 5. The protocol described in Example 5 was repeated five times using the extracts from five different batches of fruit. The angiogenesis inhibiting data for each of the five batches of fruit from *Ficus carica* L., variety kadota, is provided in FIGS. 5A-5B, 6A-6B, 7A-7B, 8A-8B and 9A-9B, respectively.

EXAMPLE 7

The effect on the angiogenic response of an extract from *Ficus carica* L., variety gold, as prepared in Example 1, was evaluated by the procedure of Example 5. The protocol described in Example 5 was repeated five times using the extracts from five different batches of fruit. The angiogenesis inhibiting data for each of the three batches of fruit from *Ficus carica* L., variety gold, is provided in FIGS. 10A-10B, 11A-11B and 12A-12B, respectively.

EXAMPLE 8

The effect on the angiogenic response of an extract from *Ficus carica* L., variety magnolia, as prepared in Example 1, was evaluated by the procedure of Example 5. The protocol described in Example 5 was repeated five times using the extracts from five different batches of fruit. The angiogenesis inhibiting data for each of the three batches of fruit from *Ficus carica* L., variety magnolia, is provided in FIGS. 13A-13B, 14A-14B and 15A-15B, respectively.

EXAMPLE 9

The extract obtained from *Ficus carica* L., variety kadota (isolated by the process described in Example 1), that exhibited angiogenesis inhibiting activity was characterized by High-Performance Liquid Chromatography ("HPLC") using a WATERS 600E HPLC system (Waters Corp., Milford, Mass.), equipped with a 717 auto sampler and a 2996 UV-Vis photodiode array detector (having a detector range of 200 nm-400 nm) and using a $C_{18}$ reverse phase column (250 mm length× 4.6 mm internal diameter WATERS Waters SYMMETRY® $C_{18}$ column) in combination with a YMC $C_{18}$ guard column (7.5 mm length×4.6 mm internal diameter). The reverse phase column contained a spherical packing material having a particle size of 3.5 µm and about 5 µm, having a pore size of about 100 Å, and having a carbon load of about 19%. The reverse phase column was also end-capped. The eluent was a first eluent, which consisted of HPLC-grade acetonitrile, and a second eluent, which consisted of HPLC-grade water containing 2.5% by volume HPLC-grade acetonitrile and 0.3% by volume phosphoric acid. The concentration of the first eluent and second eluent was provided a total eluent concentration of 100% by volume. From 0 minutes to 20 minutes and 59 seconds the first eluent increased linearly from 0% to 10% by volume of the total eluent, from 21 minutes to 50 minutes and 59 seconds the first eluent increased linearly from 10% to 20% by volume of the total eluent, from 51 minutes to 65 minutes and 59 seconds the first eluent increased linearly from 20% to 40% by volume of the total eluent, and from 66 minutes to 80 minutes and 59 seconds the first eluent increased linearly from 41% to 60% by volume of the total eluent. The column temperature was maintained at 25° C. The injection volume was 10 µL. The flow rate was 1 mL/minute. The pressure of the column increased linearly from 0 minutes to about 80 minutes, from a starting pressure of 1,000 psi to a final pressure of 3,000 psi. The photodiode array detected peak intensity at 254 nm, and run-to-run variability for peak retention times was about ±0.2 minutes.

Referring to FIG. 16, plot 1610 is a chromatograph of the angiogenesis inhibiting extract. Plot 1610 displayed a series of peaks in the chromatograph having retention times of about 4.9 minutes (1611), about 6.0 minutes (1612), about 21.3 minutes (1613), about 22.5 minutes (1614), about 35.0 minutes (1615), and about 49.7 minutes (1616). Also observed were peaks having retention times of about 3.0 minutes (1617), about 3.2 minutes (1618), about 4.9 minutes (1619), about 6.0 minutes (1620), about 8.6 minutes (1621), about 15.3 minutes (1622), about 17.0 minutes (1623), about 18.0 minutes (1624), about 19.6 minutes (1625), about 27.7 minutes (1626), about 28.7 minutes (1627), about 29.3 minutes (1628), about 30.4 minutes (1629), about 33.1 minutes (1630), about 34.0 minutes (1631), about 37.0 minutes (1632), about 44.1 minutes (1633), about 45.7 minutes (1634), about 46.3 minutes (1635), about 48.2 minutes (1636), about 53.0 minutes (1637), and about 57.3 minutes (1638). Also observed in the chromatograph was a peak, 1640, having a retention time of about 51.0 minutes and corresponding to rutin. While rutin does not exhibit angiogenesis inhibiting activity, rutin can serve as a chemical marker for the angiogenesis inhibiting *Ficus* extract of the present invention.

EXAMPLE 10

Compounds present in various extracts and samples isolated by the process of the present invention were characterized using HPLC. A reference solution (10 mL) was prepared by mixing ten compounds that were previously characterized as present in the latex-containing portion (e.g., fruit) of *Ficus carica* L. variants: psoralen (32 mg/mL), catechin (39 mg/mL), rutin (68 mg/mL), syringin (38 mg/mL), bergapten (16 mg/mL), chlorogenic acid (39 mg/mL), fumaric acid (90 mg/mL), shikimic acid (61 mg/mL), quinic acid (90 mg/mL) and coumaric acid (56 mg/mL) in methanol. The resulting solution was filtered through a membrane (pore size=0.2 mm) and characterized by HPLC by the method described in Example 9.

Figure 17:
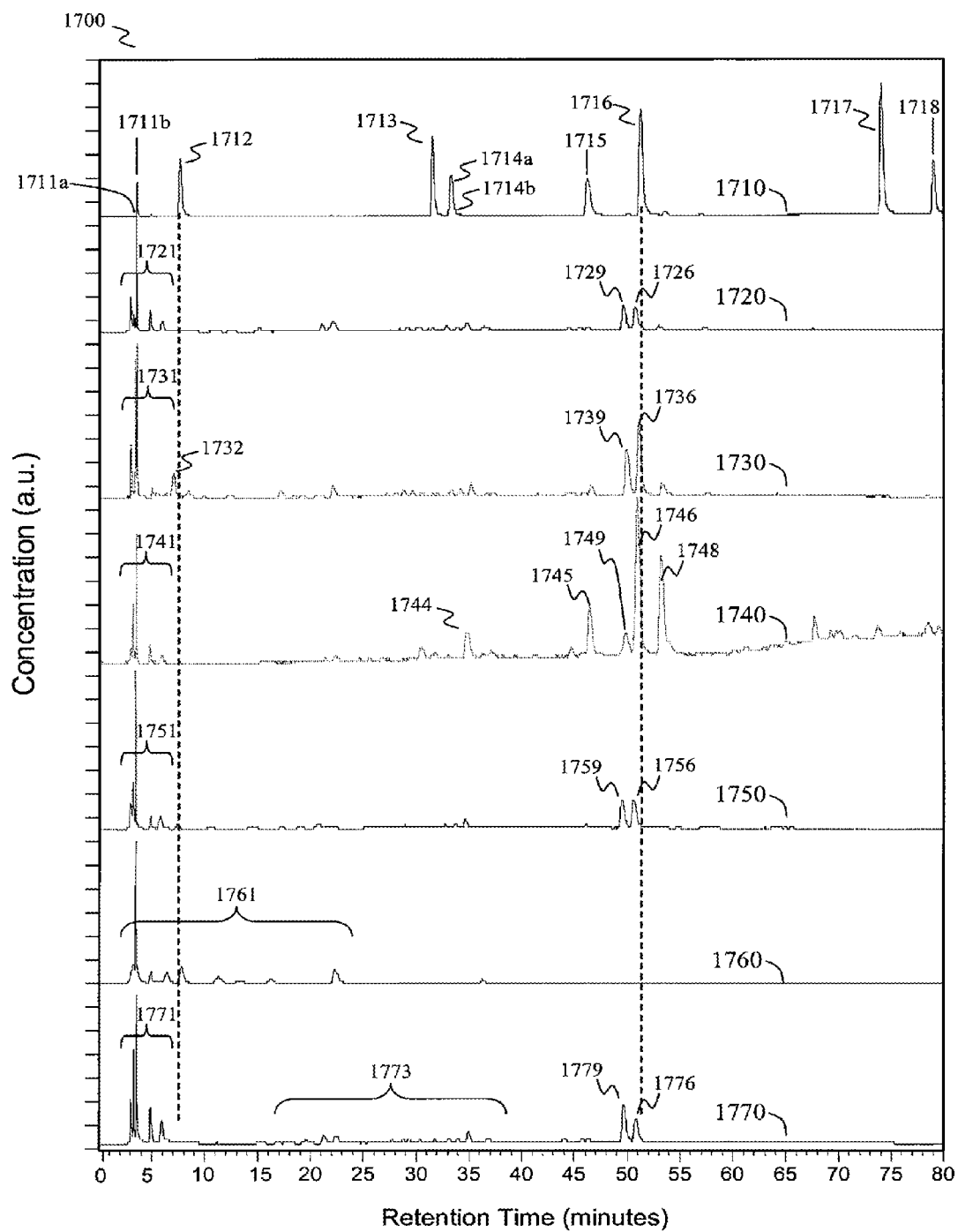
FIGS. 17, 18 and 19 provide graphical representations of high-performance liquid chromatographs of various *Ficus carica* L. raw materials, extracts and other process products of the present invention.

FIG. 17 provides a graphical representation of the chromatograph, 1710, obtained from the reference solution. Referring to FIG. 17, a chart, 1700, shows the HPLC chromatograph, 1710, (absorbance at 254 nm vs. retention time) of the reference solution. Peaks in the chromatograph corresponding to substances having an absorption at 254 nm were observed for quinic acid (1711a, having retention time of about 3.0 minutes); shikimic acid (1711b, having a retention time of about 3.6 minutes); fumaric acid (1712, having a retention time of about 7.7 minutes); syringin (1713, having a retention time of about 31.6 minutes); chlorogenic acid (1714*a*, having a retention time of about 33.3 minutes); catechin (1714*b*, having a retention time of about 33.3 minutes); coumaric acid (1715, having a retention time of about 46.2 minutes); rutin (1716, having a retention time of about 51.3 minutes); psoralen (1717, having a retention time of about 74.1 minutes); and bergapten (1718, having a retention time of about 79.0 minutes); respectively.

EXAMPLE 11

The HPLC chromatograph for the reference solution was compared with several other process products of the present invention. Dried fruit of *Ficus carica* L., variety kadota was taken up in absolute methanol and sonicated for 60 minutes to provide a sonicated fraction, $F_{son}$. The sonicated fraction, $F_{son}$, was characterized by HPLC as described in Example 9, the results of which are depicted in FIG. 17 as chromatograph 1620.

Referring to FIG. 17, chromatograph 1720 displays multiple peaks having a retention time of about 2-8 minutes, 1721, as well as two closely spaced peaks having a retention time of about 50 minutes, 1726 and 1729. Peak 1726 corresponds to rutin, present in the chromatograph of the reference solution, 1710, a peak 1716, whereas peak 1729 lacks a corresponding peak in the reference chromatograph, 1710.

EXAMPLE 12

Whole fresh figs, *Ficus carica* L., variety kadota, were placed in methanol (1:10 w/v fresh fruit:methanol) and allowed to incubate for 72 hours at room temperature. The resulting supernatant was decanted from the solid portion and then filtered (filter pore size=20 μm). The filtered solution was then concentrated using a rotary evaporator. The resulting crude solid fraction, $F_s$, was dissolved in water and characterized by HPLC using the procedure described Example 9. The chromatograph of the dissolved solid is displayed in FIG. 17.

Referring to FIG. 17, the chromatograph, 1730, of the dissolved solid, displays a series of peaks having retention times of about 2-8 minutes, 1731, including peak 1732, which corresponds to fumaric acid. Chromatograph 1730 also displays a pair of peaks having a retention time of about 50 minutes, 1736 and 1739, the former, 1736, which corresponds to rutin, the latter, 1739, lacking a corresponding peak in the reference chromatograph, 1710.

EXAMPLE 13

Fractions resulting from isolation of extracts from the latex-containing portion of *Ficus carica* L., variety kadota, as described in Example 1 were further characterized by HPLC according to the procedure of Example 9, the chromatographs of which are displayed in FIG. 17. Referring to FIG. 17, the following chromatographs are displayed: plot 1740 is a chromatograph of the organic fraction, 241 ($F_{org}$) in FIG. 1; plot 1750 is a chromatograph of the aqueous fraction, 242 ($F_{aq}$) in FIG. 1; plot 1760 is a chromatograph of the water eluate fraction, 271 ($F_{aq\text{-}0}$) in FIG. 1; and plot 1770 is a chromatograph of the organic eluate fraction, 272 ($F_{aq\text{-}95}$) in FIG. 1.

Referring to FIG. 17, plot 1740 is a chromatograph of the organic fraction ($F_{org}$), and displays a series of peaks, 1741, having retention times of about 2-8 minutes, as well as a peak 1744, corresponding to chlorogenic acid or catechin; a peak 1745, corresponding to coumaric acid; and a peak 1746, corresponding to rutin. The chromatograph, 1740, also displays peaks 1748 and 1749 that lack corresponding peaks in the reference solution chromatograph, 1710.

Referring to FIG. 17, plot 1750 is a chromatograph of the aqueous fraction ($F_{aq}$), and displays a series of peaks similar to the chromatograph, 1720, of the sonicated fraction, ($F_{son}$), isolated by the procedure of Example 10.

Referring to FIG. 17, plot 1760 is a chromatograph of the water eluate fraction ($F_{aq\text{-}0}$), and displayed peaks 1761, having retention times of about 2-25 minutes.

Referring to FIG. 17, plot 1760 is a chromatograph of the organic eluate fraction ($F_{aq\text{-}95}$) displayed peaks 1771, having retention times of about 2-8 minutes, a series of peaks, 1773, having retention times of about 15-40 minutes, as well a peak 1776, corresponding to rutin, and a peak 1779, corresponding to an unidentified compound. The latter peak, 1779, is also present in chromatographs 1720, 1730, 1740, 1750 and 1760.

EXAMPLE 14

Figure 18:
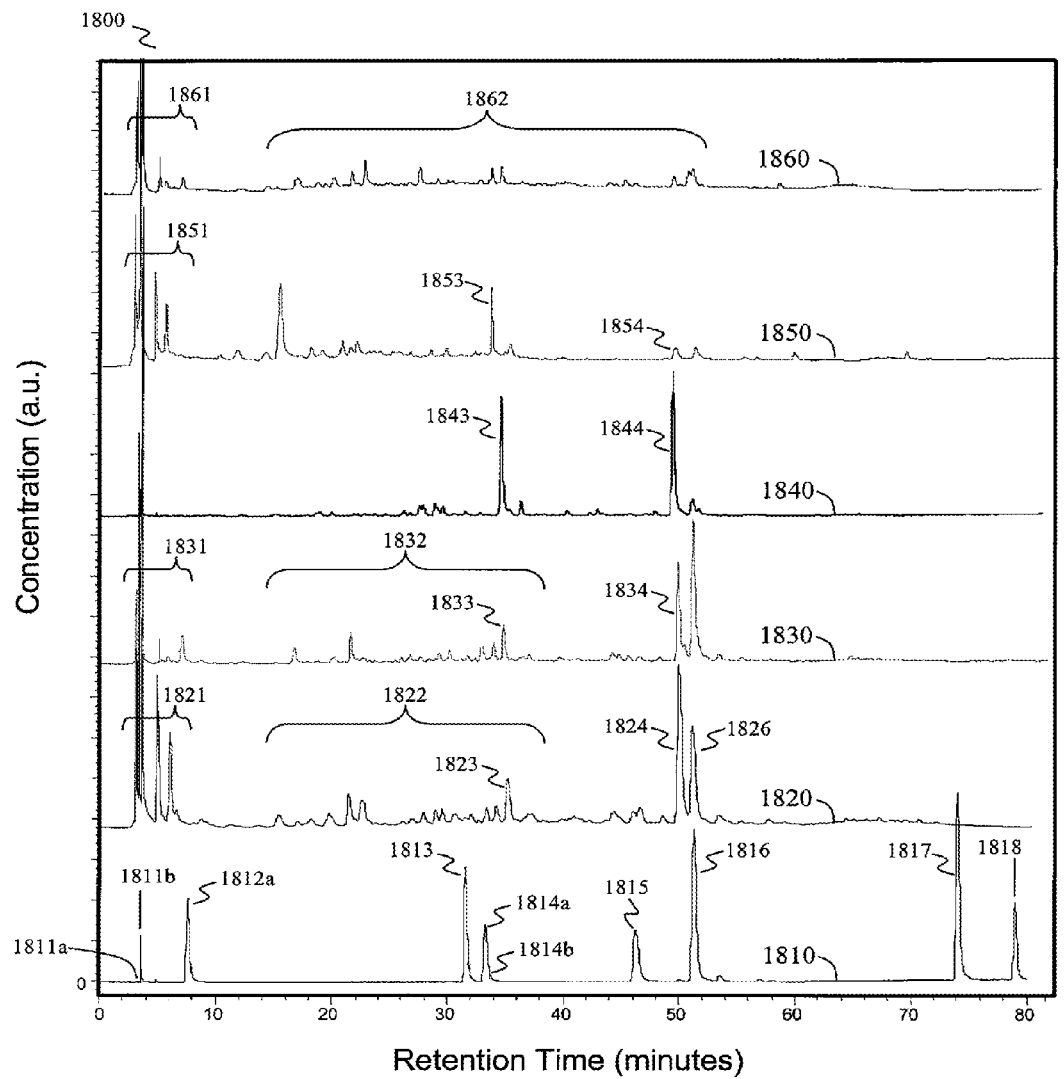

FIG. 18 provides a comparison of the HPLC chromatograph of the reference solution with several additional process products of the present invention. Referring to FIG. 18, a chart, 1800, is provided that includes plot 1810, the chromatograph of the reference solution (absorbance at 254 nm vs. retention time; also displayed in FIG. 17 as plot 1710). Peaks in the chromatograph, 1810, corresponding to substances having an absorption at 254 nm were observed for quinic acid (1811*a*); shikimic acid (1811*b*); fumaric acid (1812); syringin (1813); chlorogenic acid (1814*a*); catechin (1814*b*); coumaric acid (1815); rutin (1816); psoralen (1817); and bergapten (1818); respectively.

Referring to FIG. 18, plot 1820 is a chromatograph of the organic eluate fraction ($F_{aq\text{-}95}$) isolated from *Ficus carica* L., variety kadota (as described in Example 1). Plot 1820 displayed a series of peaks, 1821, having retention times of about 2-8 minutes, a series of peaks, 1822, having retention times of about 15-40 minutes, as well as peak 1826, which corresponds to rutin. Also observed were peaks 1823 and 1824, which do not correspond to any peaks in the chromatograph of the reference solution, 1810.

Referring to FIG. 18, plot 1830 is a chromatograph of the organic eluate fraction ($F_{aq\text{-}95}$) isolated from *Ficus carica* L., variety magnolia (as described in Example 3). Chromatograph 1830 displayed peaks similar to those observed for in the chromatograph of the organic eluate fraction isolated from fruit of the *Ficus carica* L., kadota variety, plot 1820. Specifically also observed in plot 1830 were a series of peaks, 1831, having retention times of about 2-8 minutes, a series of peaks, 1832, having retention times of about 15-40 minutes, and peak 1836, corresponding to rutin. Also observed in plot 1830 were peaks 1833 and 1834, which do not correspond to any peaks in the chromatograph of the reference solution, 1810.

EXAMPLE 15

The water-soluble portion of latex from *Ficus carica* L. (37% by weight of the raw fruit) was isolated by the procedure of Example 1 to provide a water-soluble fraction ($F_{aq}$). The aqueous fraction, $F_{aq}$, was screened for angiogenesis inhibiting activity by the procedure described in Example 5. The aqueous fraction, $F_{aq}$, was a moderate inhibitor of angiogenesis.

The aqueous fraction, $F_{aq}$, was also characterized by HPLC using the procedure described in Example 9. Referring to FIG. 18, plot 1840 is a chromatograph of the water-soluble fraction $F_w$, which displays peaks 1843 (having a retention time of about 34.0 minutes) and 1844 (having a retention time of about 49.6 minutes). Peaks having similar retention times were also observed in plots 1820 and 1830, while these peaks were not observed in the chromatograph of the reference solution. The compounds corresponding to peaks 1843 and 1844 therefore likely contribute to the angiogenesis inhibiting activity of the latex extract.

EXAMPLE 16

The organic eluate fraction, $F_{aq-95}$, isolated from the fruit of *Ficus carica* L., variety kadota, as described in Example 1 (i.e., fraction 132 in FIG. 1) was further purified by precipitation in ethanol. The solid extract (about 1 g) was added to ethanol (95% ethanol, industrial grade, 20 mL), the suspension was sonicated for 30 minutes at room temperature. The resulting supernatant was filtered using Whatman #4 paper (having a pore size of about 20 μm). The liquid was then dried using a rotary evaporator, and freeze-dried. The resulting solid was dark green in color. This procedure removed approximately 18% by weight of the material present in $F_{aq-95}$, the resulting fraction, $F_{aq-95P}$, having a purity about 1.2 times higher than the starting material.

The precipitate fraction, $F_{aq-95P}$, was characterized by HPLC using the procedure described in Example 9. Referring to FIG. 18, plot 1850 is a chromatograph of $F_{aq-95P}$, which displays peaks 1851 having retention times of about 2-8 minutes, and peaks 1853 and 1854, which are also present in other fractions that exhibited angiogenesis inhibiting activity.

EXAMPLE 17

The precipitate fraction, $F_{aq-95P}$, isolated in Example 16 was further purified by treating the *Ficus* extract with activated carbon. The extract (5 g) was dissolved in ethanol (95% ethanol, industrial grade, 100 mL) and mixed with active carbon (5 g, Sigma Chemical, St. Louis, Mo.). The resulting mixture was sonicated for 30 minutes at room temperature, then filtered using Whatman #4 paper. The resulting solution was dried using a rotary evaporator and then freeze-dried to yield a solid extract, $F_{aq-95C}$, having a mass that was about 47% of the mass of the starting material. Thus, the treating with activated carbon removed about 53% by weight of the extract material. The purified extract was light-green in color.

The activated carbon fraction, $F_{aq-95C}$, was characterized by HPLC using the procedure described in Example 9. Referring to FIG. 18, plot 1860 is a chromatograph of $F_{aq-95C}$, which displays peaks 1861 having retention times of about 2-8 minutes, as well as numerous low-intensity peaks 1862, having retention times of about 15-50 minutes, which are also present in other fractions that exhibited angiogenesis inhibiting activity.

The HPLC characterization of the angiogenesis inhibiting fractions indicates that about eight out of the ten compounds present in the reference solution are not present in an angiogenesis inhibiting extract of the present invention. Two compounds that were present in several of the extracts isolated by the procedures described herein contained fumaric acid and rutin. Fumaric acid was present in the crude solid fraction ($F_S$, Example 11), the organic fraction ($F_{org}$), the aqueous fraction ($F_{aq}$), and the aqueous eluate fraction ($F_{aq-0}$), but not the organic eluate fraction ($F_{aq-95}$) that exhibited angiogenesis inhibiting activity. Thus, the active fraction did not contain fumaric acid, and this compound is therefore not responsible for the angiogenesis inhibiting activity of the extract of the present invention. Rutin was present in the crude solid fraction ($F_S$, Example 11), the organic fraction ($F_{org}$), the aqueous fraction ($F_{aq}$), and the organic eluate fraction ($F_{aq-95}$) that exhibited angiogenesis inhibiting activity, but not the aqueous eluate fraction ($F_{aq-0}$). Therefore, in addition to the angiogenesis inhibiting fraction, rutin is also present in several other fractions that did not exhibit angiogenesis inhibiting activity.

Figure 19:
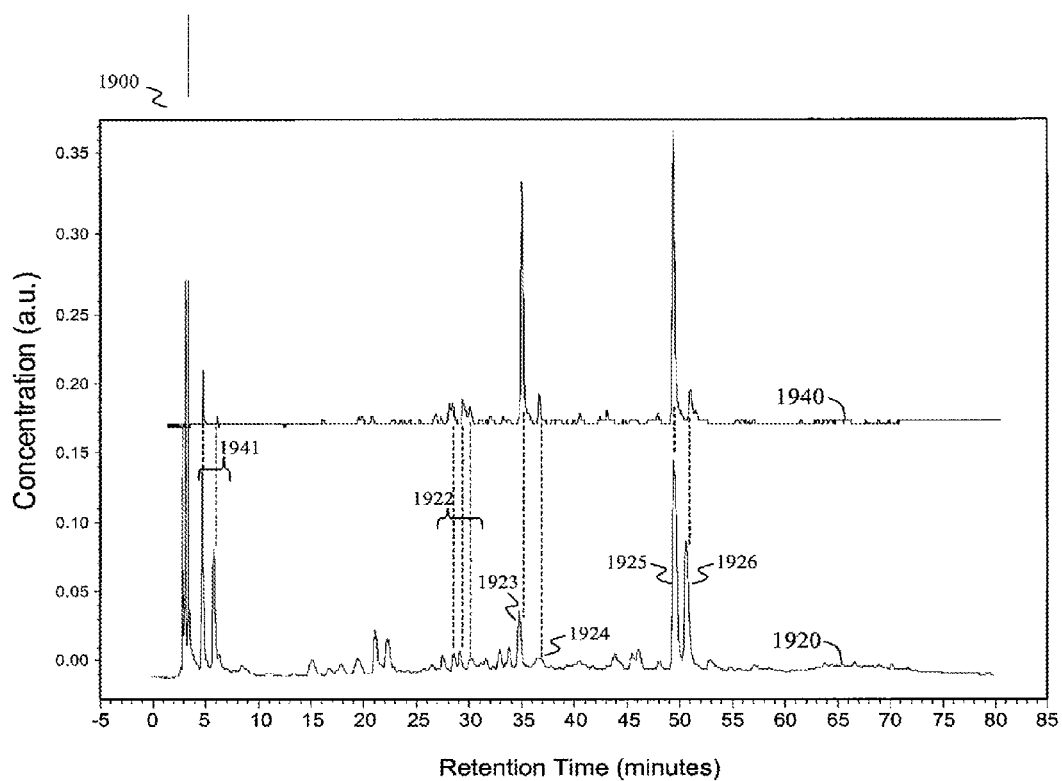

FIG. 19 provides a chart, 1900, comparing plots 1920 and 1940, which are HPLC chromatographs of the organic eluate fraction ($F_{aq-95}$) isolated from *Ficus carica* L., variety kadota (as described in Example 1) and the water-soluble fraction, $F_{aq}$, respectively. (Also shown in FIG. 18 as chromatographs 1820 and 1840, respectively.) As discussed above, both of these extracts exhibited angiogenesis inhibiting activity. Peaks common to both samples are highlighted by vertical dashed lines ( - - - - - - ). The plots show that peaks 1941, having retention times of about 4-8 minutes; peaks 1922, having retention times of about 30 minutes; peak 1923, having a retention time of about 35 minutes; peak 1924, having a retention time of about 37 minutes; and peaks 1925 and 1926, having retention times of about 50 minutes are present in both samples.

EXAMPLE 18

Figure 20C:
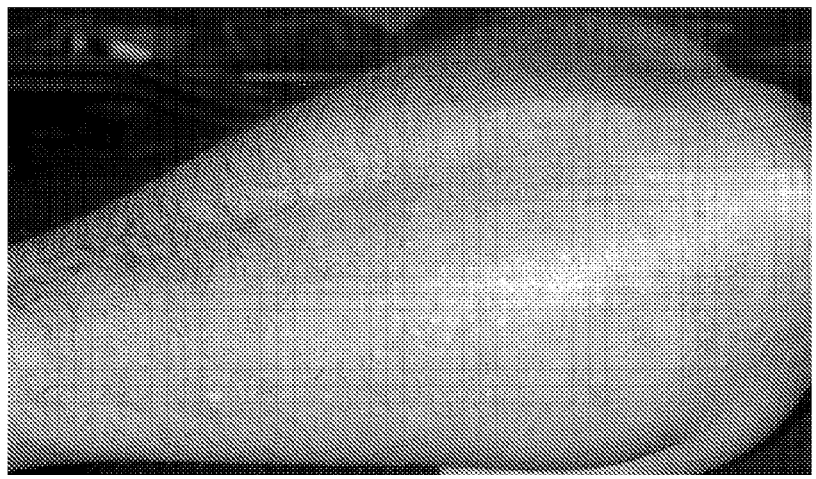
FIGS. 20A, 20B, and 20C show the result of treatment with a *Ficus* extract on psoriasis in a male human subject.
Figure 20B:
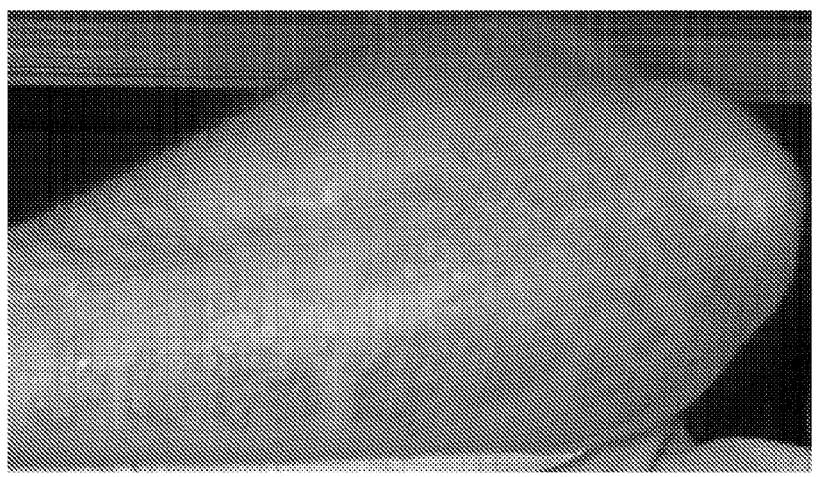
Figure 20A:
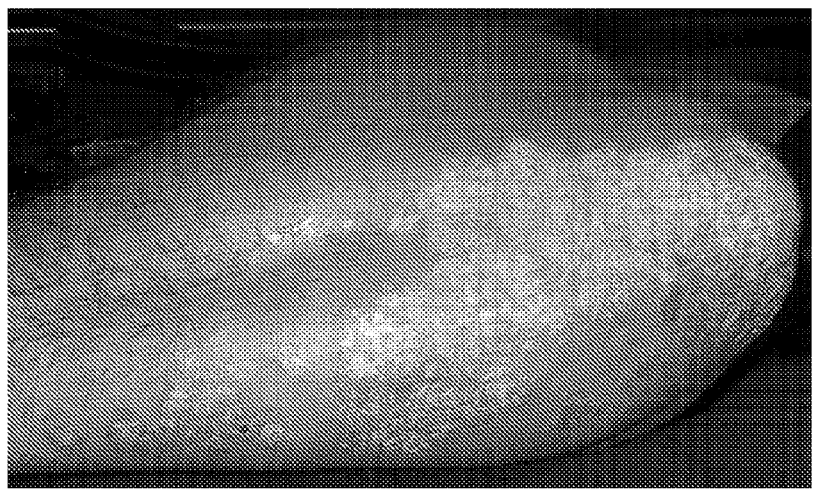

FIGS. 20A, 20B, and 20C illustrate the results obtained from topical application of *Ficus* extract to psoriatic plaques. A 1% *Ficus* extract isolated by the procedures outlined in Example 1 (organic eluate fraction ($F_{aq-95}$) isolated from *Ficus carica* L., variety 'Kadota'—see, e.g., plot 1920 of FIG. 19) was prepared in a sterile cream base for application to affected dermal lesions on a twice-daily basis. FIG. 20A shows the pre-treatment appearance of the psoriatic plaques on the left forearm of a male subject. This subject had been afflicted with psoriasis for many years, and was refractory to treatment with commonly-prescribed antipsoriatic medications. FIG. 20B shows the same forearm 39 days later, following twice-daily application of the *Ficus* extract, which produced marked reduction of psoriatic scales. FIG. 20C shows the same forearm after an additional 37 days (76 days after treatment was initiated), showing dramatic reduction of the psoriatic lesions. After the photograph of FIG. 20C was taken, treatment with *Ficus* extract was discontinued to estimate the time to relapse. Psoriatic lesions did not recur until about 4 months following discontinuation of treatment.

EXAMPLE 19

Fibrin clots were prepared in 96-well plates (Corning Inc., Corning, N.Y.). Each well was preloaded with a human thrombin solution (0.05 IU/mL; in 2.0 μL/well), (Sigma Chemical Company, St Louis, Mo.). A pre-coagulation solution was prepared by dissolving fibrinogen (0.3%; Sigma) and ∈-aminocaproic acid (0.5%; Sigma) in serum-free growth medium consisting of medium 199 (Mediatech, Herndon Va.) supplemented with an antibiotic-antifungal solution (Gibco/Invitrogen, Grand Island, N.Y.; 100 Units/mL of sodium penicillin G, 100 μg/mL of streptomycin sulfate, and 25 μg of amphotericin B) and buffered to a pH of 7.6.

Tumor specimens were placed in chilled serum-containing growth media (medium 199 with 20% fetal bovine serum [FBS], Gibco/Invitrogen) and kept under refrigeration until they were processed. The specimens were processed within 24 hours of surgical harvesting. Minced tumor fragments approximately 2 mm in diameter and 1 mm thick were prepared and rapidly embedded within the fibrin clots. Each tumor fragment was placed in the center of a thrombin-treated well. The pre-coagulation solution (0.1 mL) was layered over the tumor fragments. Clot formation took place within 30 to 60 minutes at 37° C. in a humidified environment using 6% $CO_2$, 94% air. The tumor-containing clot was then supplemented with 100 µL of a nutrient growth medium (medium 199 supplemented with antibiotics, antimycotic, and 20% FBS; control medium) or 100 µL of nutrient growth medium containing a drug. The drugs were present at the concentrations shown in FIGS. 21, 22, and 23. Total well volume was 200 µL. Nutrient or drug treatments were added on day 0 and replenished on day 7. The cultures were maintained for 14 days.

The visual evaluation of all wells was performed using an inverted phase-contrast microscope. Tumor fragments were graded using two criteria: initiation of angiogenic response [percent initiation, (% 1)] and the degree of angiogenic neovessel development, [angiogenic index (AI)]. Initiation of an angiogenic response was defined as the development of three or more sprouts around the periphery of the disk, visible at 10× magnification. Percent initiation (% I) is a ratio calculated from the number of wells that developed an angiogenic response divided by the total number of wells prepared (×100). For the angiogenic index (AI), each well containing a tumor fragment was visually divided into four quadrants and each quadrant was rated on a 0 to 4 scale for the amount (length, density, and percentage of the circumference involved in the angiogenic response) of angiogenic growth. A total score (sum of the four quadrants) of 0 to 16 was created for each well. The angiogenic index of individual wells was then averaged in one of two manners: 1) average of wells that had an AI of 1 or greater (AI growth), 2) average of all wells prepared (AI overall angiogenic response). The first growth-based calculation includes only wells that initiated an angiogenic response and excludes wells that did not sprout neovessels; it is considered a quantification of pure neovessel growth. The second calculation averages all wells regardless of whether or not an angiogenic response was observed. Because this value includes all wells, it incorporates both the degree of new vessel initiation as well as the degree of neovessel growth thus yielding a score that reflects the overall angiogenic response.

Previous experience with culture techniques in a human placental vein-based model and a variety of tumor-based models showed an excellent correlation between observer scores and more objective ratings, such as vessel length (mm) or a total vessel surface area ($mm^2$) determined by digital image analysis. In addition, comparisons of observer scores generated by multiple graders have a high degree of correlation. The visual rating system was utilized because neovessel growth could be more rapidly evaluated by visual inspection by a trained grader than with digital image analysis.

Figure 21:
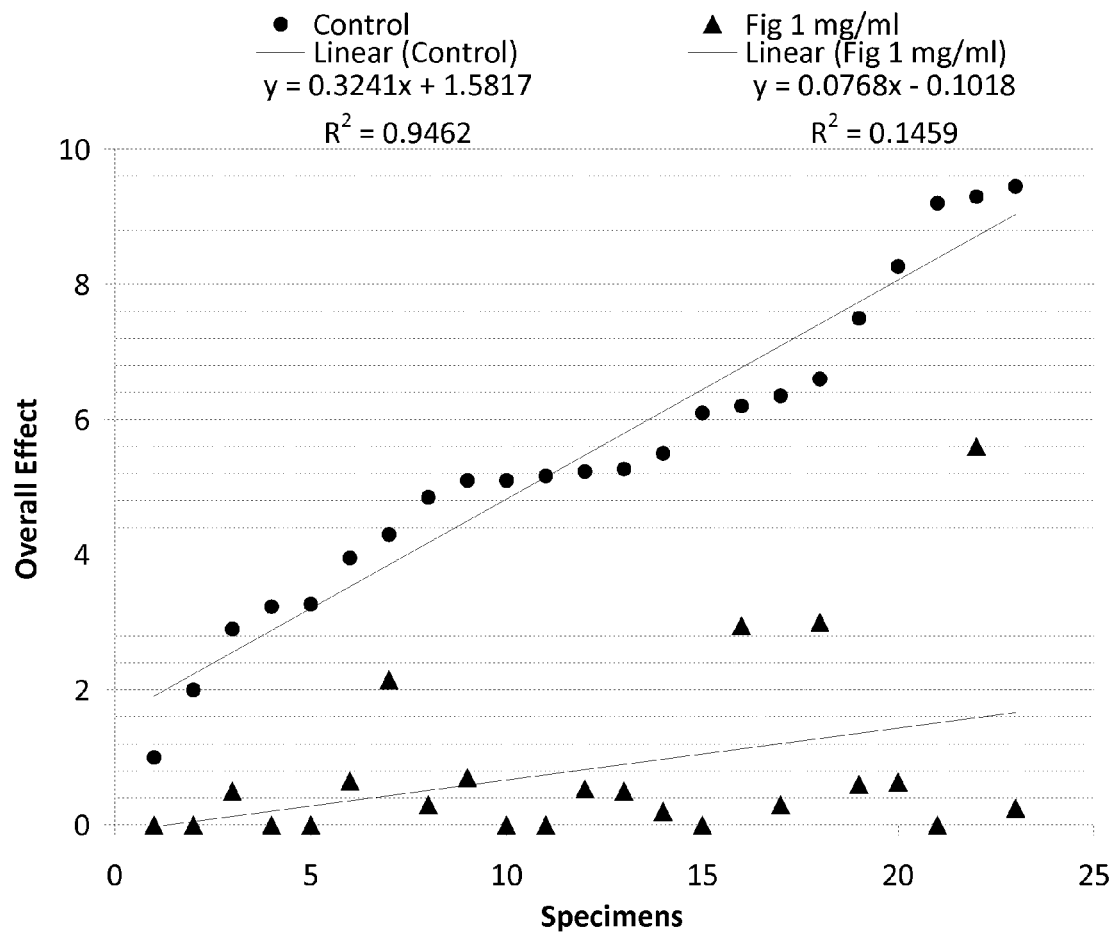
FIG. 21 shows the result of treatment with a *Ficus* extract on angiogenesis in carcinoid tumors.

FIG. 21 shows the overall effect of treatment with *Ficus* extract on angiogenesis in carcinoid tumors. The data reflect the effect on both initiation and neovessel growth (overall effect; all wells plated were included in the analysis) in individual specimens. Data were sorted in ascending order based on the control response value (filled circles) and the corresponding drug-treated value is indicated (filled triangles). As FIG. 21 shows, *Ficus* extract at 1 mg/mL is a highly effective inhibitor of angiogenesis in human carcinoid tumors compared to responses obtained in untreated control samples from the same specimen. In FIG. 21, a theoretical efficacy was estimated using the slopes of the control and drug-treated specimens; trendlines and their associated equations are shown. Values on the x-axis (individual tumor specimens) were ordered from the lowest to highest control response for each angiogenic parameter; the drug-treated values were then paired with the control value. The slopes, obtained from the trendline equations, provide a numerical estimate of angiogenic potential (control) or response (drug-treated) for the tumor sample population evaluated in this series. The slope ratio (drug/control) relates the drug effect, be it stimulation or inhibition, to the normal control angiogenic response for this tumor sample. The theoretic efficacy was calculated as [(1−[drug slope/control slope])×100]. A higher value suggests greater antiangiogenic efficacy.

Figure 22:
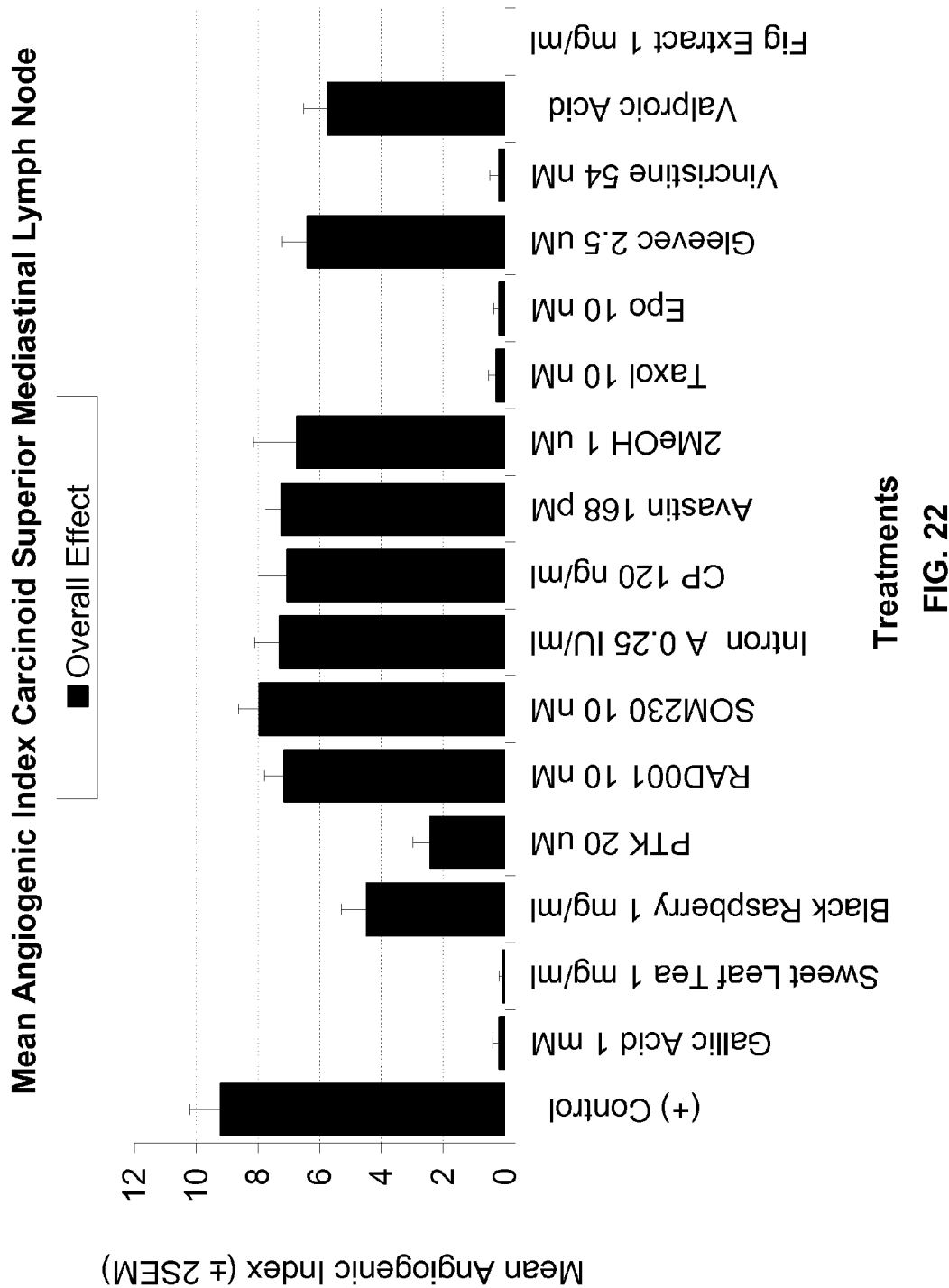
FIG. 22 shows the results of treatment with various compounds, including a *Ficus* extract, on angiogenesis in fragments from a neuroendocrine lymph node.

FIG. 22 shows the effects of various drugs on neuroendocrine lymph node metastasis. Fragments from a neuroendocrine lymph node metastasis were embedded in fibrin clots. The fragments were treated with various drugs, 30 wells per treatment group. On day 14, fragments were examined microscopically and scored for an angiogenic response (angiogenic index=0-16). Data presented are the Mean angiogenic response±2 S.E.M. for each drug treatment (n=30). Treatments included PTK787 20 µM, Gleevec 2.5 µM, SOM 230 10 nM, Interferon α 0.25 IU/mL, CP 673451, Avastin 168 µM, Epothilone B (Epo) 10 nM, RAD001 10 nM, 2 Methoxyestradiol 1 µM, Taxol 10 nM, Colchicine 100 µM, Vincristine 54 nM, Valproic Acid 1 mM, Sweet Leaf Tea 0.5 mg/mL, Black Raspberry 1 mg/mL, and Fig (*Ficus*) extract 1 mg/mL. Controls included media alone (Control), and Gallic Acid (1 mM; total inhibition). In this specimen, the angiogenic response of the control (untreated) was significant (angiogenic index of 9.2) while the angiogenic response with drug treatment varied. Fig extract completely inhibited angiogenesis in this specimen.

Figure 23:
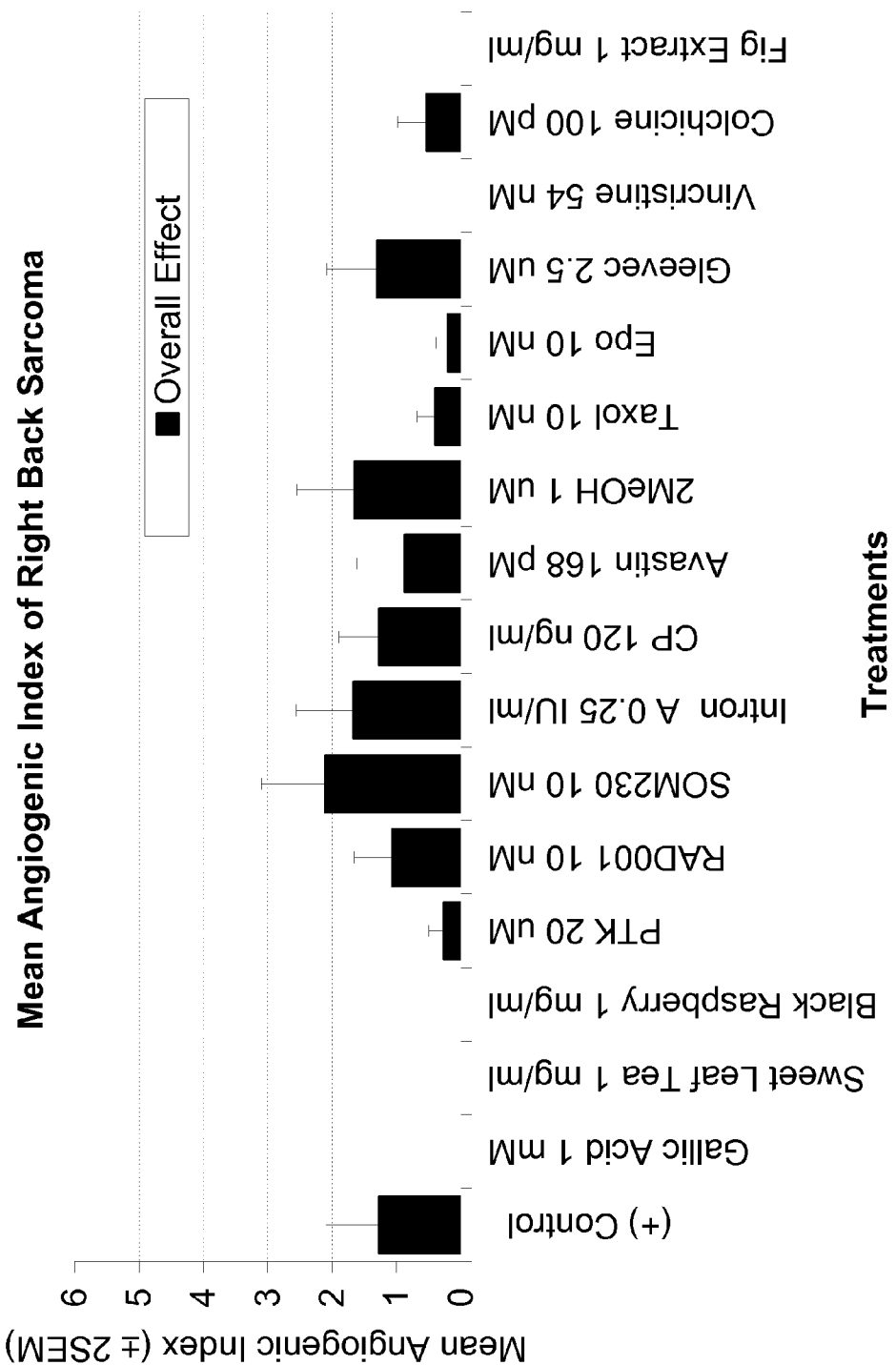
FIG. 23 shows the results of treatment with various compounds, including a *Ficus* extract, on angiogenesis in fragments from a sarcoma.

FIG. 23 shows the effects of various drugs on sarcoma. Fragments from a sarcoma were embedded in fibrin clots. The fragments were treated with various drugs, 30 wells per treatment group. On day 14, fragments were examined microscopically and scored for an angiogenic response (angiogenic index=0-16). Data presented are the Mean angiogenic response±2 S.E.M. for each drug treatment (n=30). Treatments included PTK787 20 µM, Gleevec 2.5 µM, SOM 230 10 nM, Interferon α 0.25 IU/mL, CP 673451, Avastin 168 µM, pothilone B (Epo) 10 nM, RAD001 10 nM, 2 Methoxyestradiol 1 µM, Taxol 10 nM, Colchicine 100 µM, Vincristine 54 nM, Valproic Acid 1 mM, Sweet Leaf Tea 0.5 mg/mL, Black Raspberry 1 mg/mL, and Fig (*Ficus*) extract 1 mg/mL. Controls included media alone (Control), and Gallic Acid (1 mM; total inhibition). In this specimen, the angiogenic response of the control (untreated) was low (angiogenic index of 1.3) and the angiogenic response with drug treatment varied. Fig extract completely inhibited angiogenesis in this specimen.

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All the various embodiments or options described herein can be combined in any and all variations.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

What is claimed is:

1. A process for isolating a *Ficus* extract having angiogenesis inhibiting activity, the process comprising:
   a) mixing a latex-containing portion of a *Ficus* variant with a polar solvent to provide a liquid extract;
   b) washing the liquid extract with an organic solvent to provide an aqueous extract; and
   c) fractionating the aqueous extract to provide a *Ficus* extract having angiogenesis inhibiting activity.

2. The process of claim 1, wherein the latex-containing portion of the *Ficus* variant comprises at least a portion of a fruit of the *Ficus* variant.

3. The process of claim 1, further comprising macerating the latex-containing portion of the *Ficus* variant.

4. The process of claim 1, wherein the fractionating comprises applying the aqueous extract to an adsorbent, and eluting the *Ficus* extract having angiogenesis inhibiting activity from the adsorbent with an eluting solvent.

5. The process of claim 4, wherein the adsorbent is porous and has an average pore size of about 20 nm or less.

6. The process of claim 4, wherein the eluting solvent comprises an organic.

7. The process of claim 4, wherein the eluting solvent comprises about 95% ethanol and about 5% water.

8. The process of claim 1, further comprising adding the *Ficus* extract having angiogenesis inhibiting activity to an alcoholic solution to provide a precipitate having angiogenesis inhibiting activity.

9. The process of claim 1, further comprising treating the *Ficus* extract having angiogenesis inhibiting activity with activated carbon.

10. The process of claim 1, wherein the latex-containing portion of the *Ficus* variant comprises a *Ficus carica* fruit.

11. The process of claim 1, wherein the polar solvent is a $C_1$-$C_{10}$ compound comprising a heteroatom selected from: N, O, P, S, and combinations thereof.

12. The process of claim 1, wherein the polar solvent is a solvent selected from: a $C_1$-$C_{10}$ alcohol, a $C_4$-$C_{10}$ ether, $C_3$-$C_{10}$ aldehyde, a $C_3$-$C_{10}$ ketone, a $C_2$-$C_{10}$ carboxylic acid, a $C_2$-$C_{10}$ ester, a $C_3$-$C_{10}$ amine, a $C_1$-$C_5$ amide, and combinations thereof.

13. The process of claim 1, wherein the polar solvent has a boiling point of about 200° C. or less.

14. The process of claim 1, further comprising filtering the liquid extract.

15. The process of claim 1, further comprising removing at least a portion of the polar solvent from the liquid extract.

16. The process of claim 1, wherein the washing further comprises dissolving the liquid extract in water.

17. The process of claim 1, further comprising freeze-drying one or more of the extracts.

18. A *Ficus* extract prepared by the process of claim 1, wherein the *Ficus* extract is substantially lacking cytotoxic activity.

19. A *Ficus* extract prepared by the process of claim 1, wherein the *Ficus* extract is substantially free from one or more of: shikimic acid, fumaric acid, syringin, chlorogenic acid, catechin, coumaric acid, psoralen, and bergapten.

20. A *Ficus* extract prepared by the process of claim 1, having a chromatograph having peaks at about 4.9 minutes, about 6.0 minutes, about 21.3 minutes, about 22.5 minutes, about 35.0 minutes, and about 49.7 minutes, when subjected to HPLC using a $C_{18}$ reverse phase column having an internal diameter of about 4.6 mm and a length of about 250 mm;
   a) wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and
   b) wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

21. The *Ficus* extract of claim 20, wherein the $C_{18}$ reverse phase column comprises a packing material having a particle size of about 3 µm to about 5 µm, a pore size of about 100 Å, and a carbon loading of about 19%.

22. A *Ficus* extract prepared by the process of claim 1, having a chromatograph substantially in accordance with FIG. 16 when subjected to HPLC using a $C_{18}$ reverse phase column having an internal diameter of about 4.6 mm and a length of about 250 mm;
   a) wherein a first eluent is acetonitrile and a second eluent is water containing 0.3% phosphoric acid and 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and
   b) wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

23. The *Ficus* extract of claim 22, wherein the $C_{18}$ reverse phase column comprises a packing material having a particle size of about 3 µm to about 5 µm, a pore size of about 100 Å, and a carbon loading of about 19%.

24. A process for obtaining a *Ficus* extract having angiogenesis inhibiting activity in a human or animal, the process comprising:

a) preparing an aqueous extract from a latex-containing portion of a *Ficus* variant; fractionating the aqueous extract; and b) selecting as the *Ficus* extract having angiogenesis inhibiting activity in a human or animal, a substantially protein-free fraction containing one or more compounds having a molecular weight of about 200 Da to about 2,000 Da, wherein the *Ficus* extract exhibits angiogenesis inhibiting activity.

25. The process of claim 24, wherein the angiogenesis inhibiting activity is exhibited as an inhibition or a reduction of neovessel growth in an in vitro model.

26. The process of claim 24, wherein the angiogenesis inhibiting activity is exhibited as an inhibition or a reduction of neovessel growth in a human or animal subject in need thereof.

27. The process of claim 24, wherein the *Ficus* extract has angiogenesis inhibiting activity in the micromolar range.

28. The process of claim 24, wherein the *Ficus* extract is substantially free from one or more of: shikimic acid, fumaric acid, syringin, chlorogenic acid, catechin, coumaric acid, psoralen, and bergapten.

29. A *Ficus* extract obtained by the process of claim 24, having a chromatograph having peaks at about 4.9 minutes, about 6.0 minutes, about 21.3 minutes, about 22.5 minutes, about 35.0 minutes, and about 49.7 minutes, when subjected to HPLC using a $C_{18}$ reverse phase column having an internal diameter of about 4.6 mm and a length of about 250 mm;

a) wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and b) wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

30. The *Ficus* extract of claim 29, wherein the $C_{18}$ reverse phase column comprises a packing material having a particle size of about 3 µm to about 5 µm, a pore size of about 100 Å, and a carbon loading of about 19%.

31. A *Ficus* extract obtained by the process of claim 24, having a chromatograph substantially in accordance with FIG. 16 when subjected to HPLC using a $C_{18}$ reverse phase column having an internal diameter of about 4.6 mm and a length of about 250 mm;

a) wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and b) wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

32. The *Ficus* extract of claim 31, wherein the $C_{18}$ reverse phase column comprises a packing material having a particle size of about 3 µm to about 5 µm, a pore size of about 100 Å, and a carbon loading of about 19%.

33. A method of reducing or inhibiting neovessel growth in a human or animal in need thereof, said method comprising providing a medicament comprising a *Ficus* extract further comprising rutin to said human or animal, wherein the *Ficus* extract has angiogenesis inhibiting activity.

34. The method of claim 33, wherein the *Ficus* extract is substantially free from one or more of: shikimic acid, fumaric acid, syringin, chlorogenic acid, catechin, coumaric acid, psoralen, and bergapten.

35. The method of claim 33, wherein the medicament is a nutraceutical composition.

36. The method of claim 35, wherein the nutraceutical composition is a food preparation selected from: a food bar, a beverage, a food gel, a food supplement, a powder, and a syrup.

37. The method of claim 35, wherein the nutraceutical composition is formulated into a form selected from: a tablet, a capsule, a softgel, a gelcap, a liquid, a powder, a solution, a suspension, a syrup, and combinations thereof.

38. The method of claim 33, wherein the medicament is a pharmaceutical composition formulated into a pharmaceutical dosage form.

39. The method of claim 38, wherein the pharmaceutical dosage form is a tablet, a caplet, a pellet, a capsule, a gelcap, a troche, a lozenge, a syrup, a gel, an ointment, an emulsion, a patch, a solution, a dispersion, a mist, or an aerosol.

40. The method of claim 33, wherein the neovessel growth is associated with a disease.

41. The method of claim 40, wherein the disease is selected from the group consisting of: cancer; infectious diseases, including mycobacterial infections, infections of the retina, presumed ocular histoplasmosis, and infections causing retinitis or choroiditis; autoimmune disorders; benign tumors, e.g., haemangiomas (including infantile haemangiomas, capillary haemangiomas, and cavernous haemangiomas), functional endocrine tumors, acoustic neuromas, neurofibromas, trachomas, and pyogenic granulomas; atherosclerosis and atherosclerotic plaques; ocular angiogenic diseases, e.g., diabetic retinopathy, retinopathy of prematurity, macular degeneration, corneal graft rejection, neovascular glaucoma, retrolental fibroplasia, rubeosis, retinoblastoma, persistent hyperplastic vitreous syndrome, choroidal or corneal neovascularization, venous occlusion, uveitis, vitritis, Eales disease, Behcet's disease, proliferative vitreoretinopathy, ocular ischemic syndrome, and pterygium; myopia; optic pits; Best disease; Stargardt's macular dystrophy; pars planitis; chronic retinal detachment; hyperviscosity syndrome; rheumatoid arthritis; psoriasis; warts; allergic dermatitis; blistering disease; Karposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; transplant arteriopathy; restenosis; obesity; myocardial angiogenesis; coronary collaterals; cerebral collaterals; arteriovenous malformations; ischemic limb angiogenesis; primary pulmonary hypertension; pulmonary edema; asthma; nasal polyps; inflammatory bowel disease; periodontal disease; ascites; peritoneal adhesions; Osler-Weber-Rendu syndrome (hereditary hemorrhagic telangiectasia); plaque neovascularization; telangiectasia; hemophiliac joints; synovitis; osteomyelitis; osteophyte formation; angiofibroma; fibromuscular dysplasia; wound granulation; Crohn's disease; peptic ulcer; malignant tumor growth beyond 2 mm in diameter; sickle cell anemia; sarcoidosis; syphilis; pseudoxanthoma elasticum; Paget's disease; primary hyperparathyroidism; secondary hyperparathyroidism; tertiary hyperparathyroidism; arterial occlusion; carotid obstructive disease; Lyme disease; systemic lupus erythematosis; toxoplasmosis; trauma; Wegner's granulomatosis; post-laser complications; and combinations thereof.

42. The method of claim 41, wherein the disease is psoriasis.

43. The method of claim 41 wherein the disease is cancer.

44. A method of screening a *Ficus* extract having angiogenesis inhibiting activity, the method comprising:
  a) isolating a *Ficus* extract having angiogenesis inhibiting activity by a process comprising: mixing a latex-containing portion of a *Ficus* variant with a polar solvent to provide a liquid extract;
  b) washing the liquid extract with an organic solvent to provide an aqueous extract; and fractionating the aqueous extract to provide an extract having angiogenesis inhibiting activity;
  c) applying the *Ficus* extract having angiogenesis inhibiting activity to a tumor; and measuring neovessel growth from the tumor.

45. A composition comprising a *Ficus* extract that comprises rutin, wherein the *Ficus* extract exhibits angiogenesis inhibiting activity, and wherein the composition is substantially free from quinic acid.

46. The composition of claim 44, wherein the composition is substantially free from at least one of: shikimic acid, fumaric acid, syringin, chlorogenic acid, catechin, coumaric acid, psoralen, and bergapten.

47. A *Ficus* extract having angiogenesis inhibiting activity and having a chromatograph having peaks at about 4.9 minutes, about 6.0 minutes, about 21.3 minutes, about 22.5 minutes, about 35.0 minutes, and about 49.7 minutes, when subjected to HPLC using a $C_{18}$ reverse phase column having an internal diameter of about 4.6 mm and a length of about 250 mm;
  a) wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and
  b) wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

48. The *Ficus* extract of claim 47, said extract comprising rutin, wherein the rutin appears as a peak in the chromatograph having a retention time of about 51.0 minutes.

49. The *Ficus* extract of claim 47, wherein the $C_{18}$ reverse phase column comprises a packing material having a particle size of about 3 µm to about 5 µm, a pore size of about 100 Å, and a carbon loading of about 19%.

50. The *Ficus* extract of claim 47, wherein the HPLC chromatograph further comprises a chromatograph peak of at least one of: about 3.0 minutes, about 3.2 minutes, about 4.9 minutes, about 6.0 minutes, about 8.6 minutes, about 15.3 minutes, about 19.6 minutes, about 27.7 minutes, about 28.7 minutes, about 29.3 minutes, about 30.4 minutes, about 33.1 minutes, about 34.0 minutes, about 37.0 minutes, about 44.1 minutes, about 45.7 minutes, about 46.3 minutes, about 48.2 minutes, about 53.0 minutes, about 57.3 minutes, and combinations thereof.

51. The *Ficus* extract of claim 47, wherein the HPLC chromatograph is substantially free from a chromatograph peak selected from: about 7.7 minutes, about 31.6 minutes, about 74.1 minutes, about 79.0 minutes, and combinations thereof.

52. A *Ficus* extract having angiogenesis inhibiting activity and having a chromatograph substantially in accordance with FIG. 16 when subjected to HPLC using a $C_{18}$ reverse phase column having an internal diameter of about 4.6 mm and a length of about 250 mm;
  a) wherein a first eluent is acetonitrile and a second eluent is water containing about 0.3% phosphoric acid and about 2.5% acetonitrile, the concentration of the first eluent and second eluent is 100% by volume, and from 0 minutes to about 20 minutes the first eluent increases linearly from 0% to about 10% by volume, from about 20 minutes to about 50 minutes the first eluent increases linearly from about 10% to about 20% by volume, from about 50 minutes to about 65 minutes the first eluent increases linearly from about 20% to about 40% by volume, and from about 65 minutes to about 80 minutes the first eluent increases linearly from about 40% to about 60% by volume; and
  b) wherein the column temperature is about 25° C.; the injection volume is about 10 µL; the flow rate is about 1 mL/minute; from 0 minutes to about 80 minutes the pressure increases linearly from about 1,000 psi to about 3,000 psi; and detection is at about 254 nm.

53. The *Ficus* extract of claim 52, wherein the $C_{18}$ reverse phase column comprises a packing material having a particle size of about 3 µm to about 5 µm, a pore size of about 100 Å, and a carbon loading of about 19%.

* * * * *